US012447032B2

(12) United States Patent
Martin et al.

(10) Patent No.: US 12,447,032 B2
(45) Date of Patent: Oct. 21, 2025

(54) SINGLE-UPRIGHT OSTEOARTHRITIS BRACES AND RELATED METHODS

(71) Applicant: DJO, LLC, Carlsbad, CA (US)

(72) Inventors: Trent Martin, Winchester, CA (US); Seth Sarabian, Fresno, CA (US); Jeremy Nathanson, Vista, CA (US); Jonathan Nuñez, San Marcos, CA (US); Hayley Meier, San Diego, CA (US)

(73) Assignee: DJO, LLC, Carlsbad, CA (US)

(*) Notice: Subject to any disclaimer, the term of this patent is extended or adjusted under 35 U.S.C. 154(b) by 360 days.

(21) Appl. No.: 18/103,013

(22) Filed: Jan. 30, 2023

(65) Prior Publication Data

US 2023/0240874 A1 Aug. 3, 2023

Related U.S. Application Data

(60) Provisional application No. 63/305,991, filed on Feb. 2, 2022.

(51) Int. Cl.
*A61F 5/01* (2006.01)

(52) U.S. Cl.
CPC .... *A61F 5/0106* (2013.01); *A61F 2005/0197* (2013.01)

(58) Field of Classification Search
CPC .................. A61F 5/0106; A61F 5/0123; A61F 2005/0197
See application file for complete search history.

(56) References Cited

U.S. PATENT DOCUMENTS

| | | |
|---|---|---|
| 3,350,719 A | 11/1967 | Mcclure |
| 3,528,412 A | 9/1970 | Mcdavid |

(Continued)

FOREIGN PATENT DOCUMENTS

| | | |
|---|---|---|
| EP | 1647246 A1 | 4/2006 |
| EP | 1588678 B1 | 6/2007 |

(Continued)

OTHER PUBLICATIONS

Adam, Chris, et al.; Implication of Unloader Braces in guideline recommended knee OA management. 2005.

(Continued)

*Primary Examiner* — Keri J Nelson
(74) *Attorney, Agent, or Firm* — Veros Legal Solutions, LLP

(57) ABSTRACT

A brace is provided, including a single upright assembly. The assembly includes an upper rigid support, lower rigid support, a hinge coupling the upper rigid support to the lower rigid support, an upper cuff coupled to the upper rigid support, and a lower cuff coupled to the lower rigid support. The brace includes a plurality of upper straps configured for coupling to the upper cuff such that the plurality of upper straps do not cross when the brace is properly attached to the subject. The brace includes a plurality of lower straps configured for coupling to the lower cuff such that the plurality of lower straps do not cross when the brace is properly attached to the subject. The brace includes a tensioning mechanism configured to adjust a tension in at least one of the plurality of upper and lower straps. Other braces and related methods are also provided.

28 Claims, 33 Drawing Sheets

(56) References Cited

U.S. PATENT DOCUMENTS

| | | | |
|---|---|---|---|
| 3,817,244 | A | 6/1974 | Taylor |
| 4,256,097 | A | 3/1981 | Willis |
| 4,366,813 | A | 1/1983 | Nelson |
| 4,381,768 | A | 5/1983 | Erichsen et al. |
| 4,572,170 | A | 2/1986 | Cronk et al. |
| 4,632,098 | A | 12/1986 | Grundei et al. |
| 4,691,697 | A | 9/1987 | Arensdorf et al. |
| 4,726,362 | A | 2/1988 | Nelson |
| 4,751,920 | A | 6/1988 | Mauldin et al. |
| 4,768,500 | A | 9/1988 | Mason et al. |
| 5,000,169 | A | 3/1991 | Swicegood et al. |
| 5,007,415 | A | 4/1991 | Marion |
| 5,277,698 | A | 1/1994 | Taylor |
| 5,302,169 | A | 4/1994 | Taylor |
| 5,356,370 | A | 10/1994 | Fleming |
| 5,419,754 | A | 5/1995 | Hutchins |
| 5,458,565 | A | 10/1995 | Tillinghast, III et al. |
| 5,554,104 | A | 9/1996 | Grim |
| 5,672,152 | A | 9/1997 | Mason et al. |
| 6,110,137 | A | 8/2000 | Bastyr et al. |
| 6,540,709 | B1 | 4/2003 | Smits |
| 6,565,523 | B1 | 5/2003 | Gabourie |
| 6,656,144 | B1 | 12/2003 | Coligado |
| 6,666,837 | B2 | 12/2003 | Weihermüller |
| 6,752,774 | B2 | 6/2004 | Townsend et al. |
| 6,971,996 | B2 | 12/2005 | Houser |
| 6,994,682 | B2 | 2/2006 | Bauerfeind et al. |
| 7,011,640 | B2 | 3/2006 | Patterson et al. |
| 7,147,612 | B2 | 12/2006 | Molino et al. |
| 7,150,721 | B2 | 12/2006 | Houser |
| 7,198,610 | B2 | 4/2007 | Ingimundarson et al. |
| 7,235,059 | B2 | 6/2007 | Mason et al. |
| 7,320,672 | B2 | 1/2008 | Turrini et al. |
| 7,481,785 | B2 | 1/2009 | Turrini et al. |
| 7,488,300 | B2 | 2/2009 | Houser |
| 7,500,957 | B2 | 3/2009 | Bledsoe |
| 7,578,799 | B2 | 8/2009 | Thorsteinsson et al. |
| 7,597,675 | B2 | 10/2009 | Ingimundarson et al. |
| 7,615,025 | B2 | 11/2009 | Nathanson |
| 7,662,122 | B2 | 2/2010 | Sterling |
| 7,699,798 | B2 | 4/2010 | Coligado |
| 7,704,218 | B2 | 4/2010 | Einarsson et al. |
| 7,713,225 | B2 | 5/2010 | Ingimundarson et al. |
| 7,762,973 | B2 | 7/2010 | Einarsson et al. |
| 7,794,418 | B2 | 9/2010 | Ingimundarson et al. |
| 7,837,642 | B2 | 11/2010 | Herzberg |
| 7,841,999 | B2 | 11/2010 | Napholz |
| 7,896,827 | B2 | 3/2011 | Ingimundarson et al. |
| 7,984,531 | B2 | 7/2011 | Moore |
| 7,993,292 | B2 | 8/2011 | Sterling et al. |
| 8,016,781 | B2 | 9/2011 | Ingimundarson et al. |
| 8,043,244 | B2 | 10/2011 | Einarsson et al. |
| 8,066,653 | B2 | 11/2011 | Seon |
| 8,167,829 | B2 | 5/2012 | Sterling et al. |
| 8,216,170 | B2 | 7/2012 | Ingimundarson et al. |
| 8,231,560 | B2 | 7/2012 | Ingimundarson et al. |
| 8,241,234 | B2 | 8/2012 | Ingimundarson et al. |
| 8,257,293 | B2 | 9/2012 | Ingimundarson et al. |
| 8,267,879 | B2 | 9/2012 | Ingimundarson et al. |
| 8,282,588 | B2 | 10/2012 | Ingimundarson et al. |
| 8,292,838 | B2 | 10/2012 | Ingimundarson et al. |
| 8,328,745 | B2 | 12/2012 | Einarsson et al. |
| 8,328,746 | B2 | 12/2012 | Ingimundarson et al. |
| 8,425,441 | B2 | 4/2013 | Ingimundarson |
| 8,512,268 | B2 | 8/2013 | Weihermueller |
| 8,585,623 | B2 | 11/2013 | Ingimundarson |
| 8,764,692 | B2 | 7/2014 | Ferrigolo et al. |
| 8,805,521 | B2 | 8/2014 | Carroll |
| 8,808,211 | B2 | 8/2014 | Paulos et al. |
| 8,852,133 | B2 | 10/2014 | Paulos et al. |
| 8,864,692 | B2 | 10/2014 | Ingimundarson et al. |
| 8,894,595 | B2 | 11/2014 | Hennessy |
| 8,920,350 | B2 | 12/2014 | Merkley et al. |
| 8,979,782 | B2 | 3/2015 | Romo et al. |
| 9,022,965 | B2 | 5/2015 | Auberger et al. |
| 9,066,788 | B2 | 6/2015 | Price et al. |
| 9,095,417 | B2 | 8/2015 | Dar et al. |
| 9,198,792 | B2 | 12/2015 | Skahan et al. |
| 9,220,622 | B2 | 12/2015 | Ingimundarson et al. |
| 9,265,644 | B2 | 2/2016 | Einarsson et al. |
| 9,265,645 | B2 | 2/2016 | Ingimundarson et al. |
| 9,320,634 | B2 | 4/2016 | Paulos |
| 9,358,146 | B2 | 6/2016 | Thorsteinsdottir et al. |
| 9,370,439 | B2 | 6/2016 | Bédard et al. |
| 9,387,114 | B2 | 7/2016 | Kandt |
| 9,439,800 | B2 | 9/2016 | Ingimundarson et al. |
| 9,554,933 | B2 | 1/2017 | Ingimundarson et al. |
| 9,554,934 | B2 | 1/2017 | Paulos et al. |
| 9,668,903 | B2 | 6/2017 | Hsu et al. |
| 9,775,662 | B2 | 10/2017 | Ingvarsson et al. |
| 9,788,988 | B2 | 10/2017 | Kompa |
| 9,814,615 | B2 | 11/2017 | Ingimundarson |
| 9,820,870 | B2 | 11/2017 | Franke et al. |
| 9,895,250 | B2 | 2/2018 | Thorsteinsdottir et al. |
| 9,931,233 | B2 | 4/2018 | Oaks et al. |
| 10,034,789 | B2 | 7/2018 | Knecht |
| 10,052,221 | B2 | 8/2018 | Albertsson et al. |
| 10,070,983 | B2 | 9/2018 | Garrish |
| 10,098,774 | B2 | 10/2018 | Modglin |
| 10,182,935 | B2 | 1/2019 | Sigurdsson et al. |
| 10,271,982 | B2 | 4/2019 | Volker |
| 10,369,037 | B2 | 8/2019 | Siddiqui et al. |
| 10,675,166 | B2 | 6/2020 | Paulos et al. |
| 10,744,019 | B2 | 8/2020 | Omarsson et al. |
| 10,753,129 | B2 | 8/2020 | Gunnsteinsson et al. |
| 10,758,393 | B2 | 9/2020 | Ingimundarson et al. |
| 10,765,180 | B2 | 9/2020 | Ingimundarson et al. |
| 10,786,381 | B2 | 9/2020 | Paulos et al. |
| 10,952,886 | B2 | 3/2021 | Thorsteinsdottir et al. |
| 10,966,851 | B2 | 4/2021 | Ingimundarson et al. |
| 11,129,740 | B2 | 9/2021 | Ingimundarson |
| 2003/0109818 | A1 | 6/2003 | Evans et al. |
| 2004/0068215 | A1 | 4/2004 | Adelson et al. |
| 2007/0038168 | A1 | 2/2007 | Turrini et al. |
| 2007/0130665 | A1 | 6/2007 | Wang |
| 2007/0232972 | A1 | 10/2007 | Martinez |
| 2011/0105969 | A1 | 5/2011 | Nace |
| 2013/0267878 | A1 | 10/2013 | Franke et al. |
| 2014/0221891 | A1 | 8/2014 | Sreeramagiri et al. |
| 2014/0316317 | A1 | 10/2014 | Nace et al. |
| 2015/0148726 | A1 | 5/2015 | Bonin |
| 2015/0164660 | A1 | 6/2015 | Will et al. |
| 2015/0305909 | A1* | 10/2015 | Kausek ................. A61F 5/0109 602/16 |
| 2016/0128860 | A1 | 5/2016 | Leatt et al. |
| 2016/0346112 | A1 | 12/2016 | Ingimundarson et al. |
| 2016/0367391 | A1 | 12/2016 | Paulos et al. |
| 2017/0086671 | A1 | 3/2017 | Sessler |
| 2017/0105865 | A1 | 4/2017 | Gildersleeve et al. |
| 2017/0119568 | A1 | 5/2017 | Chiang et al. |
| 2017/0196312 | A1* | 7/2017 | Xanthos ............... A43C 11/008 |
| 2017/0224519 | A1 | 8/2017 | Knecht |
| 2017/0252200 | A1 | 9/2017 | Taylor |
| 2017/0298981 | A1 | 10/2017 | Ásgeirsson |
| 2017/0348130 | A1 | 12/2017 | Petursson |
| 2017/0348131 | A1 | 12/2017 | Petursson et al. |
| 2017/0360586 | A1 | 12/2017 | Dempers et al. |
| 2017/0367867 | A1 | 12/2017 | Nathanson et al. |
| 2018/0033285 | A1 | 2/2018 | Hyde et al. |
| 2018/0042749 | A1 | 2/2018 | Ingimundarson |
| 2018/0078398 | A1 | 3/2018 | Ingimundarson et al. |
| 2018/0116828 | A1 | 5/2018 | Quinn et al. |
| 2018/0116852 | A1 | 5/2018 | Petursson et al. |
| 2018/0338836 | A1 | 11/2018 | Fujisawa et al. |
| 2019/0105188 | A1 | 4/2019 | Petursson et al. |
| 2019/0105189 | A1 | 4/2019 | Petursson et al. |
| 2019/0142620 | A1 | 5/2019 | Omarsson et al. |
| 2019/0151133 | A1 | 5/2019 | Lee et al. |
| 2019/0216627 | A1 | 7/2019 | Requa |
| 2019/0240054 | A1 | 8/2019 | Paulos et al. |
| 2019/0240056 | A1 | 8/2019 | Thor |
| 2019/0343671 | A1 | 11/2019 | Siddiqui et al. |
| 2019/0350735 | A1 | 11/2019 | Ingimundarson et al. |

(56) References Cited

U.S. PATENT DOCUMENTS

| | | | |
|---|---|---|---|
| 2020/0015991 | A1 | 1/2020 | Jonsson |
| 2020/0246171 | A1 | 8/2020 | Romo et al. |
| 2020/0397099 | A1 | 12/2020 | Ingimundarson et al. |

FOREIGN PATENT DOCUMENTS

| | | | |
|---|---|---|---|
| EP | 1462072 | B1 | 11/2007 |
| EP | 2921145 | A1 | 9/2015 |
| EP | 3123986 | B1 | 3/2018 |
| EP | 3651703 | A1 | 3/2022 |
| WO | 2001021114 | A1 | 3/2001 |
| WO | 2005087150 | A1 | 9/2005 |
| WO | 2007146320 | A2 | 9/2008 |
| WO | 2010087602 | A4 | 3/2011 |
| WO | 2011123951 | A1 | 10/2011 |
| WO | 2019101910 | A1 | 5/2019 |
| WO | 2020126781 | A1 | 6/2020 |

OTHER PUBLICATIONS

Breg, Breg Live, work, play with osteoarthritis. 2018.
Breg, Breg OA Brace Guide. 2018.
Breg, Breg Quantum OA, Launch Packet. 2018, pp. 1-38.
Breg, Breg Quantum OA, Q & A Quantum Launch. 2019.
Breg, Breg Quantum OA, Quantum Definition of Terms. 2018.
Breg, Breg Quantum OA, Quantum Fitting Tips and Techniques. 2018.
Breg, Breg Quantum OA, The Best of Both Worlds. 2018, pp. 1-4.
Briggs, Karen, et al.; Improvement in Quality of Life with Use of an Unloader Knee Brace in Active Patients with OA: A Prospective Cohort Study. J Knee Surg 2012; 25(05): 417-422, DOI: 10.1055/s-0032-1313748. https://adfarm1.adition.com/redi?id=6857929033493251279&gdpr=0&gdpr_consent=&gdpr_pd=0&userid=6642399852235719632&sid=3412883&kid=3003170&bid=9408950&c=4410&keyword=&clickurl=.
Deiel, Masataka, et al.; The Effects of an Unloading Knee Brace and Insole with Subtalar Strapping for Medial Osteoarthritis of the Knee. International Journal of Clinical Medicine, 2013, 4, 6-12. Published Online Dec. 2013 (http://www.scirp.org/journal/ijcm)http://dx.doi.org/10.4236/ijcm.2013.412A2002.
Lee, Paul YF, et al.; Unloading knee brace is a cost-effective method to bridge and delay surgery in unicompartmental knee arthritis. British Association of Sport and Exercise Medicine, vol. 2, Issue 1, 2020, pp. 1-12, https://bmjopensem.bmj.com/content/2/1/e000195.
Moyer, Rebecca, et al.; Combined Effects of a Valgus Knee Brace and Lateral Wedge Foot Orthotic on the External Knee Adduction Moment inPatients With Varus Gonarthrosis. Archives of Physical Medicine and Rehabilitation 2013;94:103-12. www.archives-pmr.org.
Ossur, Expert Consensus—Knee Osteoarthritis—WS: 1 Preserve Cartilage—Maintain High Activity Level. 2019, pp. 1-6.
Ossur, Expert Consensus—Knee Osteoarthritis—WS: 1 Preserve Cartilage—Maintain High Activity Level. 2019, pp. 1-2.
Ossur, Expert Consensus—Knee Osteoarthritis—WS: 2 Reduce Pain, Maintain Cartilage, Improve Activity Level. 2019, pp. 1-2.
Ossur, OA Solutions Unloader One X, Catalog p. www.ossur.com, pp. 1-3.
Ossur, Unloader One Lite, Instructions for Use. 2017, pp. 1-44, Rev. 5, Reykjavik, Iceland.
Ossur, Unloader One Lite, Knee Solutions. pp. 8-9.
Ossur, Unloader One X, Clinically proven osteoarthritis pain relief, 2019, pp. 1-2.
Ossur, Unloader One X, Instructions for Use, 2020, pp. 1-54, rev 3, Reykjavik, Iceland.
Ossur, Unloader One X, Smart Dosing Kit, Quick Reference Card, 2020, rev 3, Reykjavik, Iceland.
Ossur, Unloader One X, User Guide, 2019, pp. 1-6.
Ossur, Unloader One X, User Guide, pp. 1-2.
Ossur, Unloader One, Getting Started. 2017, pp. 1-2.
Ossur, Unloader One, Knee Solutions. pp. 10-12.
Toriyama, Minoru, et al.; Effects of unloading bracing on knee and hip joints for patients with medial compartment knee osteoarthritis. vol. 26, ISSUE 5, p. 497-503, Jun. 01, . DOI: https://doi.org/10.1016/j.clinbiomech.2011.01.003.
International Search Report and Written Opinion for Corresponding PCT/US2023/011882, mailed Aug. 9, 2023.

* cited by examiner

SINGLE-UPRIGHT OSTEOARTHRITIS BRACES AND RELATED METHODS

CROSS-REFERENCE TO RELATED APPLICATIONS

This application is related to, and claims priority to U.S. Provisional Patent Application Ser. No. 63/305,991, filed on Feb. 2, 2022, and entitled SINGLE-UPRIGHT OSTEOARTHRITIS BRACES AND RELATED METHODS, the contents of which is hereby incorporated by reference in its entirety.

BACKGROUND

Field of the Disclosure

The present disclosure relates generally to single-upright osteoarthritis braces and related methods.

Description of the Related Technology

Osteoarthritis (OA), commonly known as wear-and-tear arthritis, is a condition in which the natural cushioning between joints wears away. Osteoarthritis is one of the most frequent causes of physical disability among adults, with over 20 million people in the United States having the disease. By 2030, it is estimated that 20% of all Americans, approximately 70 million people, will be at risk for osteoarthritis. A degenerative joint disease, osteoarthritis causes chronic pain in the affected joint when the joint is statically or dynamically loaded.

Primary osteoarthritis often affects weight bearing joints, such as the knee. Repetitive use of a joint, such as the knee, over time can irritate and inflame the cartilage, causing joint pain and swelling. Eventually, cartilage begins to degenerate and as cartilage is diminished, the bones of the knee joints rub more closely against one another with less of the shock-absorbing benefits of cartilage. The rubbing can result in pain, swelling, stiffness, decreased mobility as well as the possibility of bone spur formation. The most common cause of osteoarthritis of the knee is age. However, several factors increase the risk of developing significant arthritis including age, weight, repetitive stress injuries, and certain athletic endeavors such as soccer, tennis, or long-distance running.

In an affected knee, osteoarthritis pain is often caused by an unbalanced loading on the medial or lateral compartment of the joint. Such unbalanced loading can generate increased pressure and reduce the clearance space between the condyles of the femur and tibial plateau. Increased pressure between the femoral and tibial surfaces in an affected compartment of the knee joint can lead to cartilage degeneration. As the cartilage degenerates, the osteoarthritis sufferer experiences increased pain in the knee.

Orthopedic braces are commonly applied to the leg to treat osteoarthritis of the knee and other painful knee conditions. Such braces typically include an upper support portion, a lower support portion, and one or more hinge assemblies pivotally interconnecting the upper and lower support portions. The upper support portion is secured to the wearer's upper leg, while the lower support portion is secured to the wearer's lower leg. The hinge assembly is located to a side of the wearer's knee and a condyle pad is typically located between each hinge assembly and the adjacent side of the knee. For example, a thickness of the adjacent condyle pad may be increased or the pad may be moved closer to the knee. The applied force generates resultant forces in the medial/lateral plane above and below the knee. The upper and lower support portions of the brace, respectively, apply these resultant forces on the side of the affected compartment. This load realigns the knee. By realigning the orientation of the knee joint, the brace reduces the load in the affected compartment of the knee, thereby lessening the pain and the other negative effects of osteoarthritis.

Osteoarthritis braces are primarily designed to correct the abnormal bending of the knee joint inwards or outwards (i.e., Varus or Valgus correction, respectively) and prevent the "bone-on-bone" contact of the femur and tibia bones in the medial and/or lateral compartment of the knee joint as the patient bears weight during ambulation. This action of lifting the femur, pulling down the tibia or keeping the femur and tibia bones from coming in contact during the straightening of the knee during heel strike of the foot is often called "unloading" of the knee joint. By unloading the knee joint, the constant irritation of the degenerated cartilage in the effected compartment of the knee (medial or lateral) can lead to a reduction in pain and a further reduction in injury to the knee joint.

However, current brace offerings can be either difficult to assemble and wear correctly, with their multiple straps that cross one another, or difficult to adjust with their multiple, cumbersome and disparate tensioning mechanisms. Accordingly, there remains a need for improved osteoarthritis braces to serve the needs of the growing population of osteoarthritis sufferers.

SUMMARY

A brace configured for attachment to a joint of a subject is provided. The brace includes a single upright assembly. The assembly includes an upper rigid support, lower rigid support, a hinge coupling the upper rigid support to the lower rigid support, an upper cuff coupled to the upper rigid support, and a lower cuff coupled to the lower rigid support. The brace includes a plurality of upper straps configured for coupling to the upper cuff such that the plurality of upper straps do not cross when the brace is properly attached to the subject. The brace includes a plurality of lower straps configured for coupling to the lower cuff such that the plurality of lower straps do not cross when the brace is properly attached to the subject. The brace includes a tensioning mechanism configured to adjust a tension in at least one of the plurality of upper and lower straps. Other braces and related methods are also provided.

Another brace configured for attachment to a joint of a subject is provided. The brace includes a single upright assembly comprising a plurality of rigid supports and a plurality of cuffs, each coupled to one of the plurality of rigid supports. The brace includes a plurality of straps, each fixedly coupled, directly or indirectly, to at least one of the cuffs. The brace includes a magnetic coupler configured to magnetically couple at least a subset of the plurality of straps to one of the cuffs.

Another brace configured for attachment to a joint of a subject is provided. The brace includes a telescopically adjustable upright assembly. The assembly includes at least one rigid support having an end comprising a plurality of locating features configured to interact with a cuff of the brace, and a plurality of apertures, each disposed in a respective one of the locating features. The assembly includes at least one cuff including a recess configured to receive at least a subset of the plurality of locating features of the rigid support in any of a plurality of incrementally overlapped orientations, thereby disposing the cuff in a corresponding one of a plurality of telescopically adjustable configurations with respect to the rigid support. The assembly includes a plurality of locking caps, each configured to be inserted into one of the plurality of apertures and, thereby, secure the cuff in the corresponding telescopically adjustable configuration.

Yet another brace configured for attachment to a joint of a subject is provided. The brace includes a single upright assembly comprising an upper cuff coupled to an upper rigid support, a lower cuff coupled to a lower rigid support; and a hinge coupling the upper rigid support to the lower rigid support. The brace includes a plurality of upper straps configured for coupling to the upper cuff, a plurality of lower straps configured for coupling to the lower cuff, and a central harness configured to directly couple to a first end of at least two of the plurality of straps, thereby ensuring the plurality of straps do not cross when the brace is properly attached to the subject A method of utilizing brace configured for attachment to a joint of a subject is provided. The method includes donning the brace. The method includes coupling one or more straps of the brace to respective fixation features of the brace. The method includes adjusting a tension in at least one strap of the brace to, thereby, obtain a desired fit of the brace on a user.

DETAILED DESCRIPTION

Embodiments of this disclosure relate to orthopedic braces for use in treating a variety of injuries to the knee, or other joint, and surrounding ligaments. More particularly, embodiments of braces disclosed herein may be intended for use with patients with abnormal knee (or other joint) function who suffer from osteoarthritis (OA). As will be described in greater detail below and as illustrated in the FIGs., embodiments of such braces may comprise a single upright assembly comprising an upper rigid member coupled to a lower rigid member by a hinge. An upper cuff is coupled to the upper rigid member and a lower cuff is coupled to the lower rigid member. Each of a plurality of straps is configured to wrap around a portion of a thigh or calf of the subject without intersecting another strap. Straps are coupled to a bracket that is detachably coupled to a quick release buckle of the corresponding upper or lower cuff via a magnetic coupler.

Although the present embodiments are particularly well-suited for use in treating osteoarthritis of the knee, such customizable braces may also be utilized and/or modified for use in treating other joints including, for example, ankle, elbow, neck, back, and/or wrist.

Figure 1:
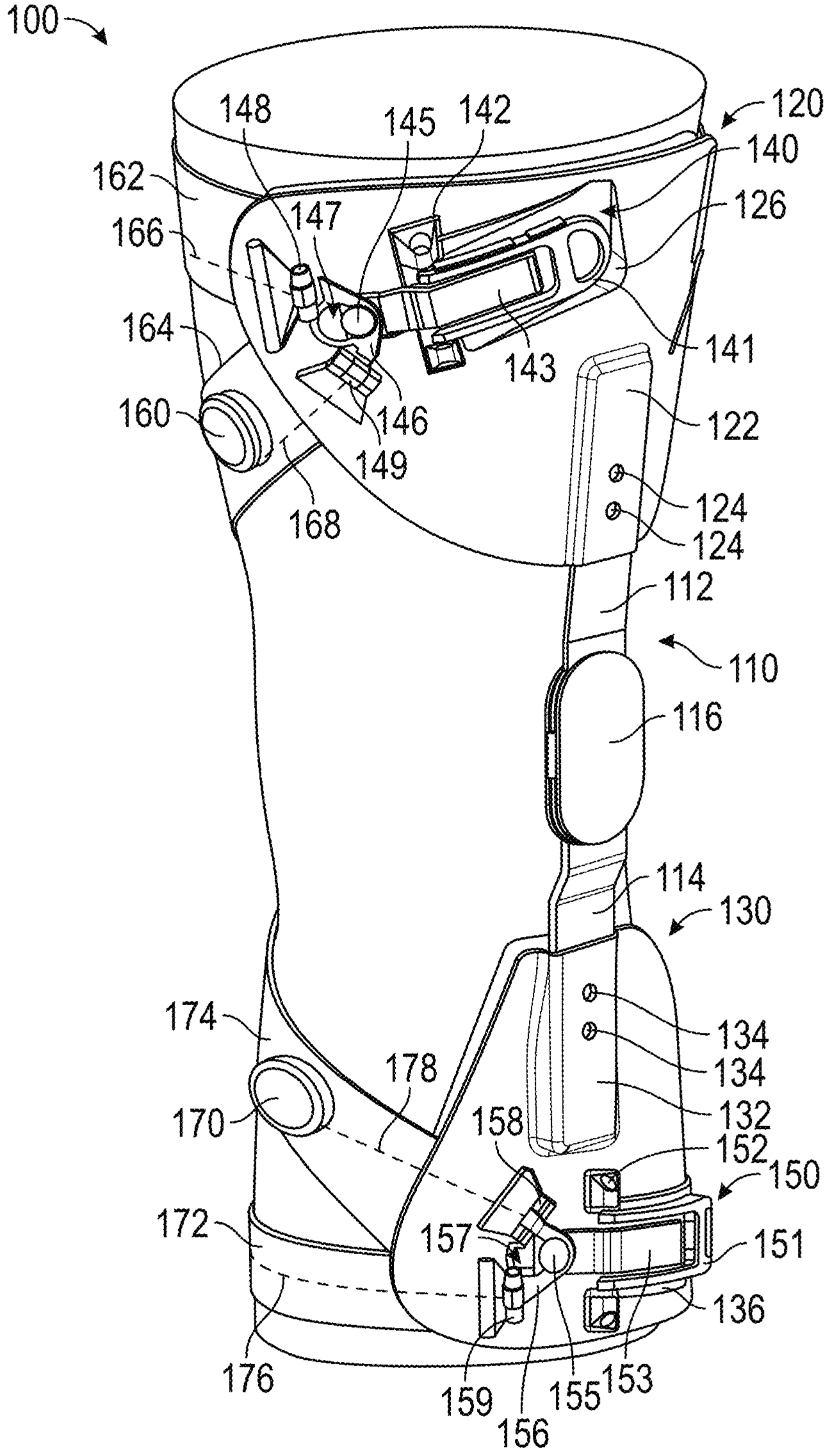
FIG. 1 illustrates a perspective view of a brace for use in the treatment of osteoarthritis, in accordance with some embodiments.
Figure 2:
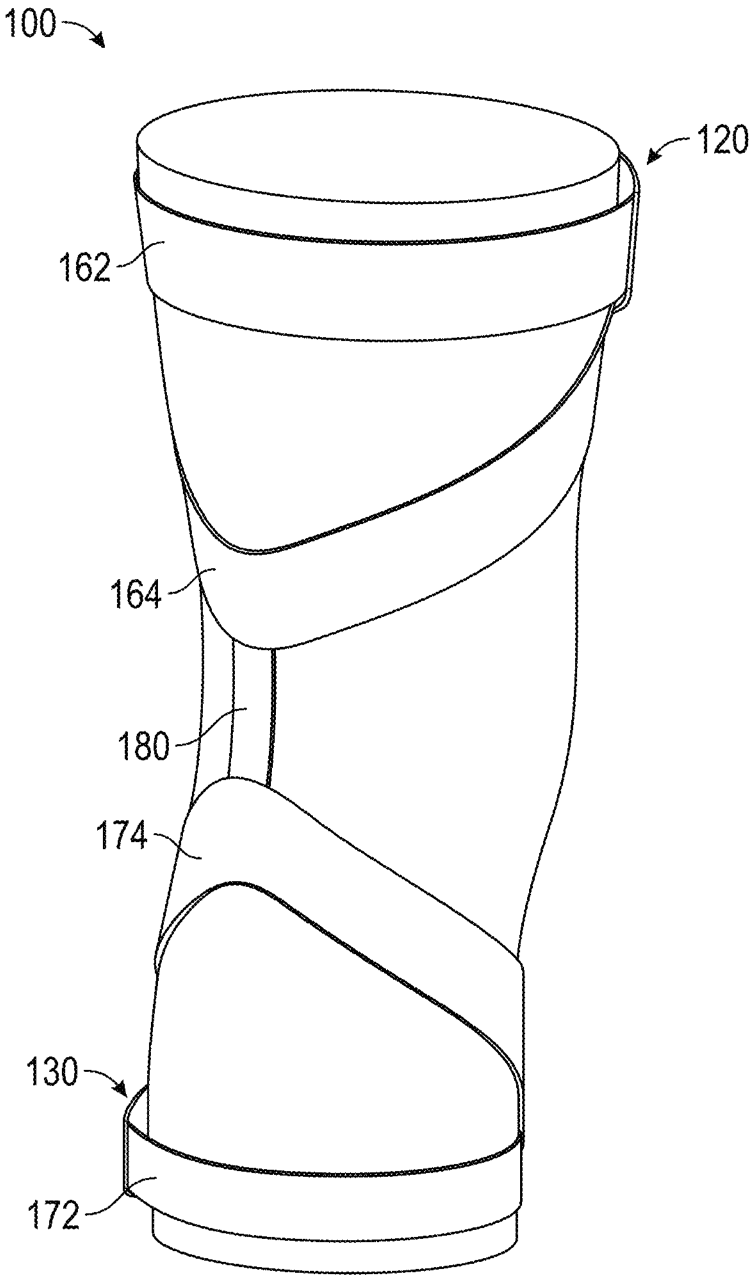
FIG. 2 illustrates a perspective view of the brace of FIG. 1 as viewed from an approximately opposite angle compared to FIG. 1 and omitting elements of the tensioning mechanisms for easy viewing of the straps, in accordance with some embodiments.
Figure 3:
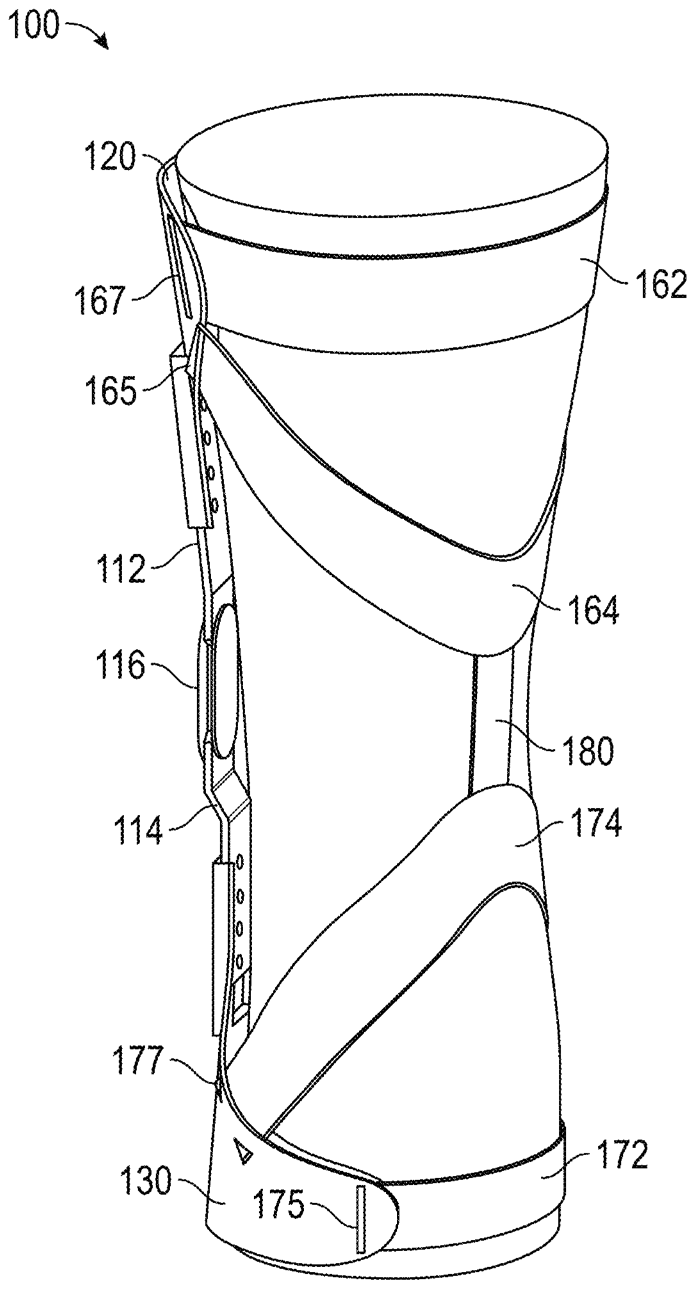
FIG. 3 illustrates a perspective view of the brace of FIG. 2 as viewed from an angle intermediate between those of FIGS. 1 and 2, in accordance with some embodiments.

FIG. 1 illustrates a perspective view of a brace 100 for use in the treatment of osteoarthritis, in accordance with some embodiments. FIGS. 2-5 illustrate different views of the brace of FIG. 1 but omit elements of the tensioning mechanisms 140, 150 for easy viewing of the straps, in accordance with some embodiments. Brace 100 is illustrated in FIG. 1 as fitted to a patient's knee. However, embodiments disclosed herein are not limited to knee braces and may be extended to braces for any suitable joint(s) of the human body.

Brace 100 comprises an upright assembly 110, which comprises an upper rigid support 112, a lower rigid support 114, and a hinge 116 physically coupling upper rigid support 112 and lower rigid support 114. In some embodiments, hinge 116 may be a unicentric joint (e.g., having a single axis of rotation or freedom of movement). In some other embodiments, for example, as illustrated in FIG. 1) hinge 116 may be a polycentric joint (e.g., having more than one axis of rotation or freedom of movement). While not illustrated, in some embodiments, the hinge may further include a condyle pad.

In some embodiments, at least one of upper rigid support 112 and lower rigid support 114 are configured to be adjusted, based on anatomical needs of the patient, so as to redistribute a portion of a load from an affected compartment of the knee of the patient, thereby reducing knee pain. For example, a treating clinician or the patient may bend or form one or both of upper rigid support 112 and lower rigid support 114 such that it forms an ideal or desired offloading angle with respect to the femur, tibia, knee joint, or external surface of the upper and/or lower leg of the patient when the brace 100 is properly worn. Accordingly, in some embodiments, upper rigid support 112 and lower rigid support 114 may be constructed of a material such as heat-formable plastic, metal, carbon fiber, or any other suitably rigid material, currently known or unknown, that is sufficiently rigid to provide the required support to and force against the knee joint and that, in some embodiments, may also be adjusted or bent to a desired angle either through use of an adjusting machine or manually, by hand, and in some embodiments, once sufficiently heated.

In some other embodiments, upper rigid support 112 and lower rigid support 114 may be wholly rigid in that they are constructed of a material that is not configured to be bent in a manner specific to the individual patient (e.g., steel, titanium, aluminum) and, instead, is fabricated to have a substantially static form, for example as shown in FIG. 1, that is designed to fit patients having a particular range of sizes and/or morphologies.

For treatment of medial compartment OA, upright 110 may be disposed along the medial side of the patient's affected leg such that hinge 116 substantially aligns with the medial side of the knee joint and the axis along which the knee bends, upper rigid support 112 is disposed along a medial portion of the patients upper leg (e.g., the thigh), and lower rigid support 114 is disposed along a medial portion of the patients lower leg (e.g., the shin and/or calf). Accordingly, when worn, the upright 110 (e.g., upper rigid support 112, hinge 116, and/or lower rigid support 114) may provide stability while straps pull on a central harness, as will be described in more detail below, to exert a force on the lateral side toward the medial side of the knee joint (i.e., a Varus adjustment), thereby increasing the separation between the femur and tibia in the medial compartment of the knee and, accordingly, providing a redistribution of a portion of the load away from the medial compartment of the knee. In at least this manner, knee pain may be reduced for the patient suffering from medial OA.

In some embodiments, for treatment of lateral compartment OA, upright 110 may instead be a lateral upright, disposed along the lateral side of the patient's affected leg such that hinge 116 substantially aligns with the lateral side of the knee joint and the axis along which the knee bends, upper rigid support 112 is disposed along the lateral portion of the patients upper leg (e.g., the thigh), and lower rigid support 114 is disposed along the lateral portion of the patients lower leg (e.g., the shin and/or calf). Accordingly, when worn, upright 110 (e.g., upper rigid support 112, hinge 116, and/or lower rigid support 114) may provide stability while straps pull on a central harness, as will be described in more detail below, to exert a force on the medial side toward the lateral side of the knee joint (i.e., a Valgus adjustment), thereby increasing the separation between the femur and tibia in the lateral compartment of the knee and, accordingly, providing a redistribution of a portion of the load away from the lateral compartment of the knee. In at least this manner, knee pain may be reduced for the patient suffering from lateral OA. In such embodiments, the construction and form of the brace may have a substantially mirror form and construction compared to that of braces configured for placement on the other side of the affected joint and treatment of medial compartment OA.

Brace 100 further comprises a upper cuff 120 coupled to upper rigid support 112. Upper cuff 120 may comprise a pocket 122 (or a raised portion or recessed portion having a similar form factor to that illustrated for pocket 122) configured to receive at least an upper end of upper rigid support 112. Upper cuff 120 may be coupled to upper rigid support 112 utilizing one or more fasteners 124 (e.g., screws or rivets secured through pocket 122 and the upper end of upper rigid support 112). In some embodiments, a thigh-facing surface of upper cuff 120 is shaped to conform to at least a lateral or medial portion of the patient's thigh. For example, as illustrated in FIG. 1, upper cuff 120 is shaped to rest against portions of the user's thigh extending between an anterior portion of the thigh and a posterior portion of the thigh along the lateral or medial side of the thigh. In some embodiments, upper cuff 120 may be constructed of heat-formable material allowing it to be adjusted, bent and/or shaped to conform at least as described above by applying modest heat and, thereby, improving the fit to the patient. In some embodiments, this heat-formable material may be substantially rigid at temperatures it would be expected to endure while being worn by the patient (e.g., temperature ranges below 120 degrees Fahrenheit). In some other embodiments, upper cuff 120 may comprise a formable metal. In this way, upper cuff 120 may be thermoformable, adjustable, and/or in some cases reformable such that a clinician and/or the patient may mold the brace directly to the patient for an improved fit, comfort, and joint stabilization in a desired orientation. Upper cuff 120 may have the additional benefit of providing some measure of local tissue compression as well as promoting general knee joint alignment, which may provide reduced inflammation and/or pain in the knee joint. In addition, in some embodiments, upper cuff 120 may also be light weight, easy to clean, and/or waterproof. In some embodiments, upper cuff 120 comprises a recess 126 configured to receive at least a portion of a tensioning mechanism 140, thereby reducing a profile of brace 100 when properly worn by the user and at least a portion of tensioning mechanism 140 is seated within recess 126.

Brace 100 further comprises a lower cuff 130 coupled to lower rigid support 114. Lower cuff 130 may comprise a pocket 132 (or a raised portion or recessed portion having a similar form factor to that illustrated for pocket 132) configured to receive at least a lower end of lower rigid support 114. Lower cuff 130 may be coupled to lower rigid support 114 utilizing one or more fasteners 134 (e.g., screws or rivets secured through pocket 132 and the lower end of lower rigid support 114). In some embodiments, a calf-facing surface of lower cuff 130 is shaped to conform to at least a lateral or medial portion of the patient's calf. For example, as illustrated in FIG. 1, lower cuff 130 is shaped to rest against portions of the user's calf extending between an anterior portion of the lower leg (the shin) and a posterior portion of the calf along the lateral or medial side of the lower leg. In some embodiments, lower cuff 130 may be constructed of the same heat-formable material as upper cuff 120. In this way, lower cuff 130 may be thermoformable, adjustable, and/or in some cases reformable such that a clinician and/or the patient may mold the brace directly to the patient for an improved fit, comfort, and joint stabilization in a desired orientation. Lower cuff 130 may have the additional benefit of providing some measure of local tissue compression as well as promoting general knee joint alignment, which may provide reduced inflammation and/or pain in the knee joint. In addition, in some embodiments, lower cuff 130 may also be light weight, easy to clean, and/or waterproof. In some embodiments, lower cuff 130 comprises a recess 136 configured to receive at least a portion of a tensioning mechanism 150, thereby reducing a profile of brace 100 when properly worn by the user and at least a portion of tensioning mechanism 150 is seated within recess 136.

Brace 100 further comprises straps 162, 164, 172, 174, each coupled to at least one of upper cuff 120 and lower cuff 130. Straps 162 and 172 act as stability straps and straps 164 and 174 act as force straps. Discussion will include several straps, slits and pads, which may not be visible in FIG. 1 but are illustrated in at least one of FIGS. 3-5 for easy reference.

A first end of strap 162 is coupled to a bracket 146 (see, e.g., FIG. 1). A second end of first upper strap 162 is coupled to a slit 167 in a posterior portion of upper cuff 120 (see, e.g., FIG. 5). In some embodiments, slit 167 may comprise a B-ring or other suitable fastening means. Strap 162 is configured to extend substantially horizontally between its first and second ends around a side of the user's thigh when brace 100 is properly worn by the user and the user is standing. Strap 162 may be considered a proximal strap of upper cuff 120.

A first end of strap 172 is coupled to bracket 156 (see, e.g., FIG. 1). A second end of first strap 172 is coupled to a slit 177 in a posterior portion of lower cuff 130 (see, e.g., FIG. 5). In some embodiments, slit 177 may comprise a d-ring or other suitable fastening means. Strap 172 is configured to extend substantially horizontally between its first and second ends around a side of the user's lower leg when brace 100 is properly worn by the user and the user is standing. Strap 172 may be considered a proximal strap of lower cuff 130.

A first end of strap 164 is coupled to bracket 146 and a first end of strap 174 is coupled to bracket 156 (see, e.g., FIG. 1). In some embodiments, a second end of strap 164 is coupled to a slit 165 in a posterior portion of upper cuff 120 (see, e.g., FIG. 5). In some such embodiments, a second end of strap 174 is also coupled to a slit 175 in a posterior portion of upper cuff 120 (see, e.g., FIG. 5). In some such embodiments, a coupling strap 180 adjustably and/or permanently couples straps 164, 174 to one another at respective points between their respective first and second ends such that, when brace 100 is properly worn by a subject, strap 164 extends diagonally from each of its first and second ends toward coupling strap 180, strap 174 extends diagonally from each of its first and second ends toward coupling strap 180, and coupling strap 180 is disposed substantially vertically and centrally against a side of the subject's joint opposite hinge 116 when the subject is standing, straight-appendaged. Notably, the straps, while connected, do not intersect. In preferred embodiments, the stability straps and force straps are constructed from an inelastic material such as woven nylon fabric.

In some other embodiments, one or both of straps 164 and 174 may not be configured to extend continuously from one end of their respective cuffs 120, 130, but may couple to one or more intermediate harnesses or straps. For example, in some such embodiments, the first end of each of straps 164, 174 may be coupled and/or coupleable as described above. However, a second end of each of straps 164, 174 may be coupled and/or adjustably coupleable to a central harness (see, e.g., central harness 880 in FIG. 8). For example, second ends of each of straps 164, 174 may be configured to removably fixate to and/or with such a central harness and/or other straps utilizing slots, d-rings, hook-and-loop fasteners similar to that described elsewhere herein, and/or utilizing any other suitable strap fixation and/or adjusting means described herein or otherwise known. In such embodiments, straps 164, 174 may be arranged and/or function substantially similarly to straps 864, 874 as described in connection with FIGS. 8 and 9. Accordingly, in such embodiments, brace 100 may also comprise the central harness described above and additional straps that are the same as or substantially similar to straps 863, 873 in form and/or function.

Discussion of tensioning mechanisms 140 and 150 follow. Tensioning mechanism 140 comprises a quick-release buckle 141 having a first end pivotally coupled to an anchor point 142. In some embodiments, anchor point 142 may be integrally formed as a part of upper cuff 120. In other embodiments, anchor point 142 may be a separate component from upper cuff 120 that is permanently coupled to upper cuff 120.

Quick-release buckle 141 is configured to be disposed in a locked orientation in which a second end of quick-release buckle 141 opposite the first end is disposed maximally to one direction, shown as within recess 126 of upper cuff 120 in FIG. 1. Quick-release buckle 141 is also configured to be disposed in unlocked orientations where the second end of quick-release buckle 141 has been lifted away from recess 126 and quick-release buckle 141 has been or is being pivoted, about anchor point 142, away from the locked orientation.

A first end of a quick-release extension 143 is pivotally coupled to quick-release buckle 141 at a position between the first and second ends of quick-release buckle 141. A second end 145 of quick-release extension 143, opposite the first end, is releasably coupled to bracket 146. For example, in some embodiments, second end 145 of quick-release extension 143 comprises a post having a first diameter or largest diametric dimension and a head having a second diameter or largest diametric dimension that is larger than the first diameter or largest diametric dimension. In some such embodiments, bracket 146 comprises an aperture 147 having a first portion sufficiently large to receive the head of second end 145 of quick-release extension 143 therethrough when quick-release buckle 141 is in at least one unlocked orientation, and a second portion sufficiently small to prevent the head of second end 145 of quick-release extension 143 from decoupling from bracket 146 therethrough when quick-release buckle 141 is in the locked orientation. For example, aperture 147 may have a form factor of two different-sized circles and/or ellipses that partially but do not completely overlap one another, a first of the circles and/or ellipses having a diameter or largest diametric dimension greater than that of the head of second end 145 of quick-release extension 143, and the second of the circles and/or ellipses having a diameter or largest diametric dimension smaller than the diameter or largest diametric dimension of the head of second end 145 of quick-release extension 143 but larger than the diameter or largest diametric dimension of the post of second end 145 of quick-release extension 143. In some embodiments, second end 145 of quick-release extension 143 and/or bracket 146 may alternatively or additionally comprise magnetic materials such that second end 145 of quick-release extension 143 is magnetically coupled to bracket 146 when quick-release buckle 141 is in the locked orientation and such that second end 145 of quick-release extension 143 is decoupled and/or decouplable from bracket 146 when quick-release buckle 141 is in at least one unlocked orientation.

Bracket 146 is coupled to first lace 166 that is disposed on, over or within strap 162. Bracket 146 is also coupled to second lace 168 that is disposed on, over or within strap 164. In some embodiments, straps 162, 164 may be physically coupled to bracket 146 via laces 166, 168. However, the present disclosure is not so limited and, in some other embodiments, one or both of straps 162, 164 are not directly and physically coupled to bracket 146 via cables 166, 168. Instead, in some such embodiments, straps 162, 164 may be tightened by adjusting fixation of the opposite, second end of each strap, for example, at respective slots 167, 165 in upper cuff 120 and/or respective slots, d-rings and/or hook-and-loop fasteners at a central harness similar to or the same as central harness 880 in FIGS. 8 and 9.

In some embodiments, first and second laces 166,168 are different portions of a single lace. In some other embodiments, first and second laces 166,168 are separate laces. In yet other embodiments, only one of laces 166, 168 is utilized in brace 100. Laces 166, 168 may comprise a metal cable, a braided string of polyester or nylon fibers, or any other suitable material. Any such lace may have any suitable thickness (for example approximately 1.2-2.75 millimeters (mm)), any suitable weight (for example approximately 10.6 grams (g)), any suitable length (for example approximately 500 mm) and have any suitable load capacity (for example approximately 200 Newtons (N)). Laces 166, 168 may be attached to bracket 146 utilizing an overhand knot, a figure-eight knot or any other suitable knot or fixation process.

In some embodiments, bracket 146 may comprise multiple pieces coupled to one another in a limited range of motion by a first hinge 148 and by a second hinge 149. While FIG. 1 illustrates hinges 148,149, the present disclosure is not so limited and bracket 146 may be a flexible single, integral, monolithic piece having the same above-described function.

First and/or second laces 166,168 is/are coupled to a ratcheting dial 160 that is disposed on one of straps 162,164. When twisted or otherwise activated, ratcheting dial 160 is configured to increase or decrease a tension in first and second laces 166,168 and, thereby, indirectly increase or decrease a tension in straps 162-164 that is present when brace 100 is worn by the user. Accordingly, at least dial 160 and the one or both of laces 166,168 may form a reel-and-lace tensioning element. Because first and/or second lace(s) 166,168 is/are coupled to bracket 146, when second end 145 of quick-release extension 143 is coupled within aperture 147 of bracket 146, flipping, pivoting or rotating quick-release buckle 141 from an unlocked orientation to the locked orientation causes bracket 146 to be pulled in a same direction in which quick-release extension 143 shifts, which in turn causes tension in first and/or second lace(s) 166,168 (and in strap(s) 162 and/or 164) to increase in their respective directions of extension.

Advantages of this design and operation include but are not limited to tension in first and/or second laces 166,168 (and indirectly in strap(s) 162 and/or 164) being able to be micro-adjusted before or after quick-release buckle 141 is initially moved to the locked orientation, which not only allows adjustment of the offloading of a portion of a load from a desired compartment of the knee of the patient, but also simultaneously improves the fit of strap(s) 162 and/or 164 against the surfaces of the patient's knee and leg. Moreover, once desired tension and support is set, brace 100 can be redonned by the user and quick-release buckle 141 moved to the locked orientation, and the user may instantly enjoy the prior desired level of support without readjusting ratcheting dial 160 or any other tension adjustment of brace 100. Moreover, with this design and operation quick-release buckle 141 may be permanently coupled to brace 100 and/or upper cuff 120, and strap(s) 162 and/or 164 and/or lace(s) 166 and/or 168 may be removably coupled and decouplable from quick-release extension 143 at the connection between aperture 147 of bracket 146 and second end 145 of quick-release extension 143.

Tensioning mechanism 150 has substantially identical construction and function to tensioning mechanism 140. Tensioning mechanism 150 comprises a quick-release buckle 151 having a first end pivotally coupled to an anchor point 152. In some embodiments, anchor point 152 may be integrally formed as a part of lower cuff 130. In some other embodiments, anchor point 152 may be a separate component from lower cuff 130 that is permanently coupled to lower cuff 130.

Quick-release buckle 151 is configured to be disposed in a locked orientation in which a second end of quick-release buckle 151 opposite the first end is disposed within recess 136 of lower cuff 130. Quick-release buckle 151 is also configured to be disposed in unlocked orientations where the second end of quick-release buckle 151 has been lifted away from recess 136 and quick-release buckle 151 has been or is being pivoted about anchor point 152 from the locked orientation.

A first end of a quick-release extension 153 is pivotally coupled to quick-release buckle 151 at a position between the first and second ends of quick-release buckle 151. A second end 155 of quick-release extension 153, opposite the first end, is releasably coupled to a bracket 156. For example, in some embodiments, second end 155 of quick-release extension 153 comprises a post having a first diameter or largest diametric dimension and a head disposed on the post and having a second diameter or largest diametric dimension that is larger than the first diameter or largest diametric dimension. In some such embodiments, bracket 156 comprises an aperture 157 having a first portion sufficiently large to receive the head of second end 155 of quick-release extension 153 therethrough when quick-release buckle 151 is in at least one unlocked orientation, and a second portion sufficiently small to prevent the head of second end 155 of quick-release extension 153 from decoupling from bracket 156 therethrough when quick-release buckle 151 is in the locked orientation, for example as previously described for aperture 147. In some embodiments, second end 155 of quick-release extension 153 and/or bracket 156 may alternatively or additionally comprise magnetic materials as previously described for extension 143 and/or bracket 146.

Bracket 156 is coupled to third lace 176 that is disposed on, over or within strap 172. Bracket 156 is also coupled to fourth lace 178 that is disposed on, over or within strap 174. In some embodiments, straps 172, 174 may be physically coupled to bracket 156 via laces 176, 178. However, the present disclosure is not so limited and, in some other embodiments, one or both of straps 172, 174 are not directly and physically coupled to bracket 156 via cables 176, 178. Instead, in some such embodiments, straps 172, 174 may be tightened by adjusting fixation of the opposite, second end of each strap, for example, at respective slots 177, 175 in lower cuff 130 and/or respective slots, d-rings and/or hook-and-loop fasteners at a central harness similar to or the same as central harness 880 in FIGS. 8 and 9.

In some embodiments, third and fourth laces 176,178 are different portions of a single lace. In some other embodiments, third and fourth laces 176,178 are separate laces. In yet other embodiments, only one of laces 166, 168 is utilized in brace 100. Laces 176, 178 may comprise a metal cable, a braided string of polyester or nylon fibers, or any other suitable material. Any such lace may have any suitable thickness (for example approximately 1.2-2.75 millimeters (mm)), any suitable weight (for example approximately 10.6 grams (g)), any suitable length (for example approximately 500 mm) and have any suitable load capacity (for example approximately 200 Newtons (N)). Laces 176, 178 may be attached to bracket 156 utilizing an overhand knot, a figure-eight knot or any other suitable knot or fixation process.

In some embodiments, bracket 156 may also comprise multiple pieces coupled to one another in a limited range of motion by a first hinge 158 and by a second hinge 159. While FIG. 1 illustrates hinges 158,159, the present disclosure is not so limited and bracket 146 may be a flexible single, integral, monolithic piece having the same function.

Third and/or fourth laces 176,178 is/are coupled to a ratcheting dial 170 that is disposed on one of straps 172,174. When twisted or otherwise activated, ratcheting dial 170 is configured to increase or decrease a tension in third and fourth laces 176,178 and, thereby, indirectly increase or decrease a tension in straps 172, 174 that is present when brace 100 is worn by the user. Accordingly, at least dial 170 and the one or both of laces 176,178 may form a reel-and-lace tensioning element. Because third and/or fourth lace(s) 176 and/or 178 is/are coupled to bracket 156, when second end 155 of quick-release extension 153 is coupled within aperture 157 of bracket 156, flipping, pivoting or rotating quick-release buckle 151 from an unlocked orientation to the locked orientation causes bracket 156 to be pulled in a same direction in which quick-release extension 153 shifts, which in turn causes tension in third and/or fourth lace(s) 176,178 (and in strap(s) 172 and/or 174) to increase in their respective directions of extension.

Advantages of this design and operation include but are not limited to tension in third and/or fourth laces 176,178 (and indirectly in strap(s) 172 and/or 174) being able to be micro-adjusted before or after quick-release buckle 151 is initially moved to the locked orientation, which not only allows adjustment of the offloading of a portion of a load from a desired compartment of the knee of the patient, but also simultaneously improves the fit of strap(s) 172 and/or 174 against the surfaces of the patient's knee and leg. Moreover, once desired tension and support is set, brace 100 can be redonned by the user and quick-release buckle 151 moved to the locked orientation, and the user may instantly enjoy the prior desired level of support without readjusting ratcheting dial 170 or any other tension adjustment of brace 100. Moreover, with this design and operation quick-release buckle 151 may be permanently coupled to brace 100 and/or lower cuff 130, and strap(s) 172 and/or 174 and/or lace(s) 176 and/or 178 may be removably coupled and decouplable from quick-release extension 153 at bracket 156.

Figure 6:
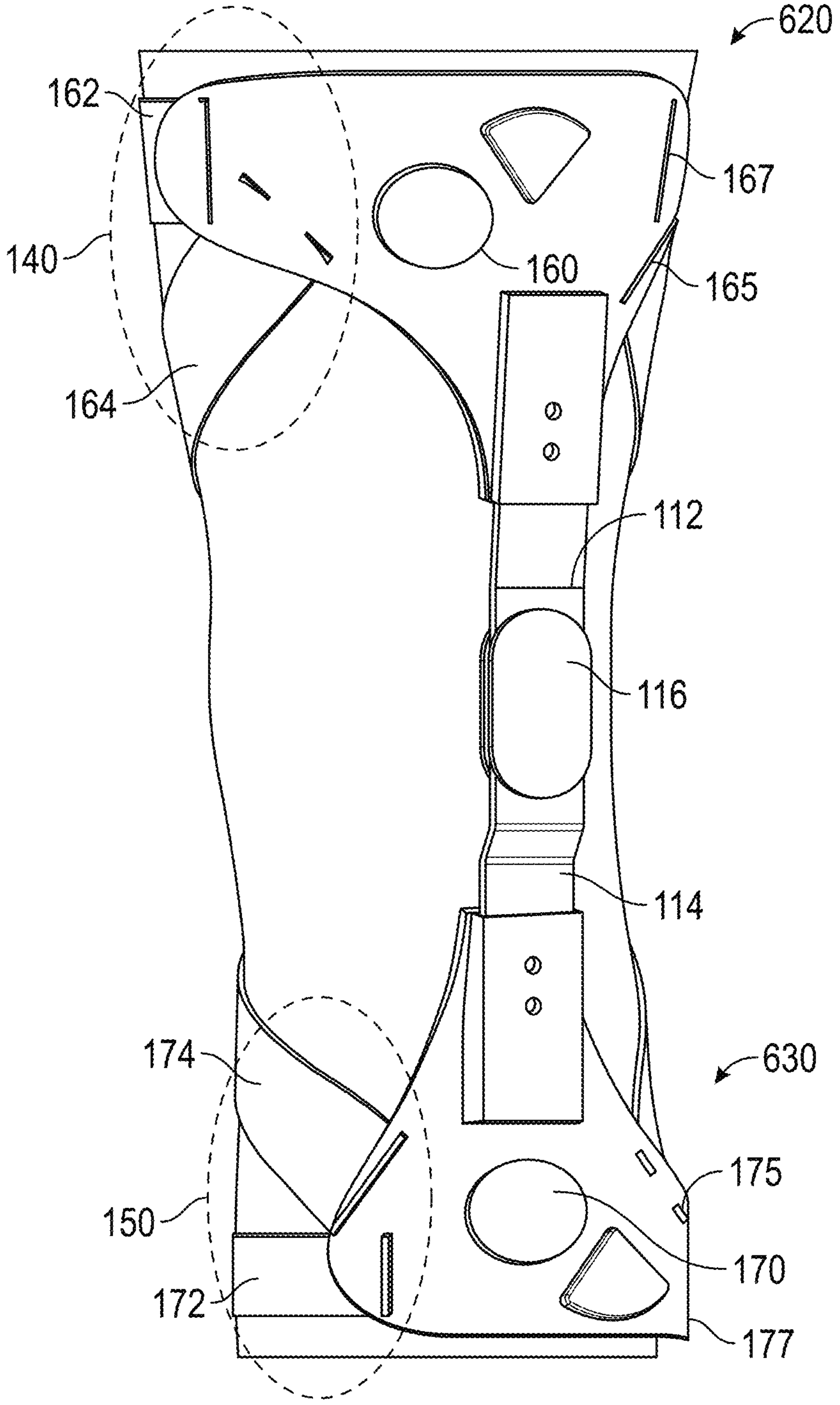
FIG. 6 illustrates a perspective view of another brace for use in the treatment of osteoarthritis, in accordance with some embodiments.

FIG. 6 illustrates a perspective view of another brace 600 for use in the treatment of osteoarthritis, in accordance with some embodiments. Brace 600 comprises upright assembly 110 as previously described in connection with at least FIG. 1. A upper cuff 620 is coupled to upper rigid member 112, a lower cuff 630 is coupled to lower rigid member 114, and hinge 116 couples upper rigid member 112 to lower rigid member 114, similar to that previously described in connection with at least FIG. 1. Brace 600 similarly comprises straps 162, 164, 172, 174, each having one end coupled to a respective slit 167, 165, 177, 175 in a posterior portion of the corresponding upper cuff 620 or lower cuff 630, and straps 164, 174 are coupled to one another via coupling strap 180 as previously described in connection with at least FIGS. 2 and 3.

However, in contrast to brace 100, where ratcheting dials 160, 170 are disposed directly on a respective one of the thigh and lower straps, for brace 600, ratcheting dials 160, 170 are disposed directly on respective upper cuff 620 and lower cuff 630. In some embodiments, quick-release buckle 141 and its related components 142-149 (see at least FIG. 1) may also be permanently or removably coupled to a portion of upper cuff 620 anterior of ratcheting dial 160. In such embodiments, quick-release buckle 151 and its related components 152-159 (see at least FIG. 1) may also be permanently or removably coupled to a portion of lower cuff 630 anterior of ratcheting dial 170. In some other embodiments, quick-release buckle 141 and its related components 142-149 (see at least FIG. 1) may be permanently or removably coupled to one or both of straps 162, 164. In such other embodiments, quick-release buckle 151 and its related components 152-159 (see at least FIG. 1) may be permanently or removably coupled to one or both of straps 172, 174.

Figure 7:
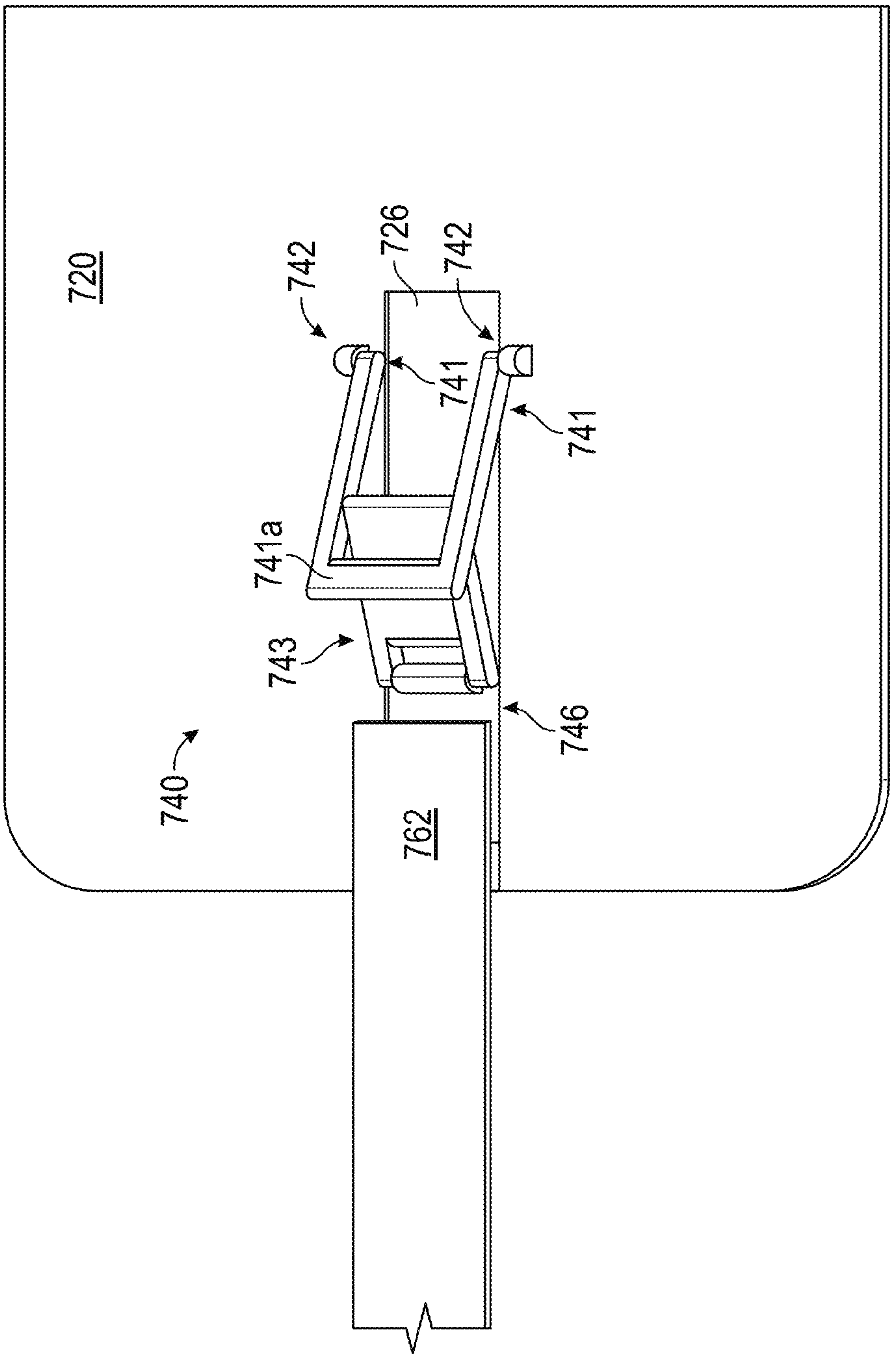
FIG. 7 illustrates an embodiment of a tensioning mechanism for use in any brace described herein, in accordance with some embodiments.

FIG. 7 illustrates an embodiment of a tensioning mechanism 740 similar to at least a portion of tensioning mechanisms 140 and/or 150 as illustrated in at least FIG. 1, in accordance with some embodiments. FIG. 7 illustrates a cuff 720, which may correspond to upper cuff 120 or lower cuff 130 of FIGS. 1-6, and/or any other cuff configured for placement against any suitable portion of a user's body as described anywhere in this disclosure.

Cuff 720 comprises an anchor point 742, which may be either a part of the frame (of which cuff 720 forms at least a portion) or which may be a separate part that is permanently integrated into that frame. In some embodiments, anchor point 742 corresponds anchor point 142 and/or 152 of FIG. 1.

At least one lever arm 741 is pivotably coupled to anchor point 742. For example, as shown in FIG. 7, respective first ends of each of two lever arms 741 may be pivotally coupled to a respective anchor point 742 disposed on either side of a channel or recess 726, and respective second ends of lever arms 741 (opposite the respective first ends) may be coupled to one another via a cross bar **741*a* or similar feature. Such a double lever arm 741 and cross bar 741*a* arrangement provides a void between lever arms 741 in which an extension arm 743 may travel, shift and/or lie, thereby reducing a profile of tensioning mechanism 740, cuff 740, and/or any brace to which it is coupled or of which it is a part. In some embodiments, lever arm(s) 741 and cross bar 714*a* corresponds to quick-release buckle 141 and/or 151 of FIG. 1. In some embodiments, extension arm 743 corresponds to extension arm 143 and/or 153 of FIG. 1**.

A first end of extension arm 743 is pivotally coupled to lever arm(s) 741 at a position between the first and second ends of lever arm(s) 741. For example, as illustrated in FIG. 7, first end of extension arm 743 is pivotally coupled to and between facing sides of lever arm(s) 741. A second end of extension arm 743 (opposite the first end) is pivotally coupled to a strap receiver element 746. In some embodiments, strap receiver element 746 corresponds to bracket 146 and/or 156 of FIG. 1. As illustrated in FIG. 7, in some embodiments, cuff 720 comprises a channel or recess 726 within which at least strap receiver element 746 is retained and configured to slide, shift and/or move within.

Figure 8:
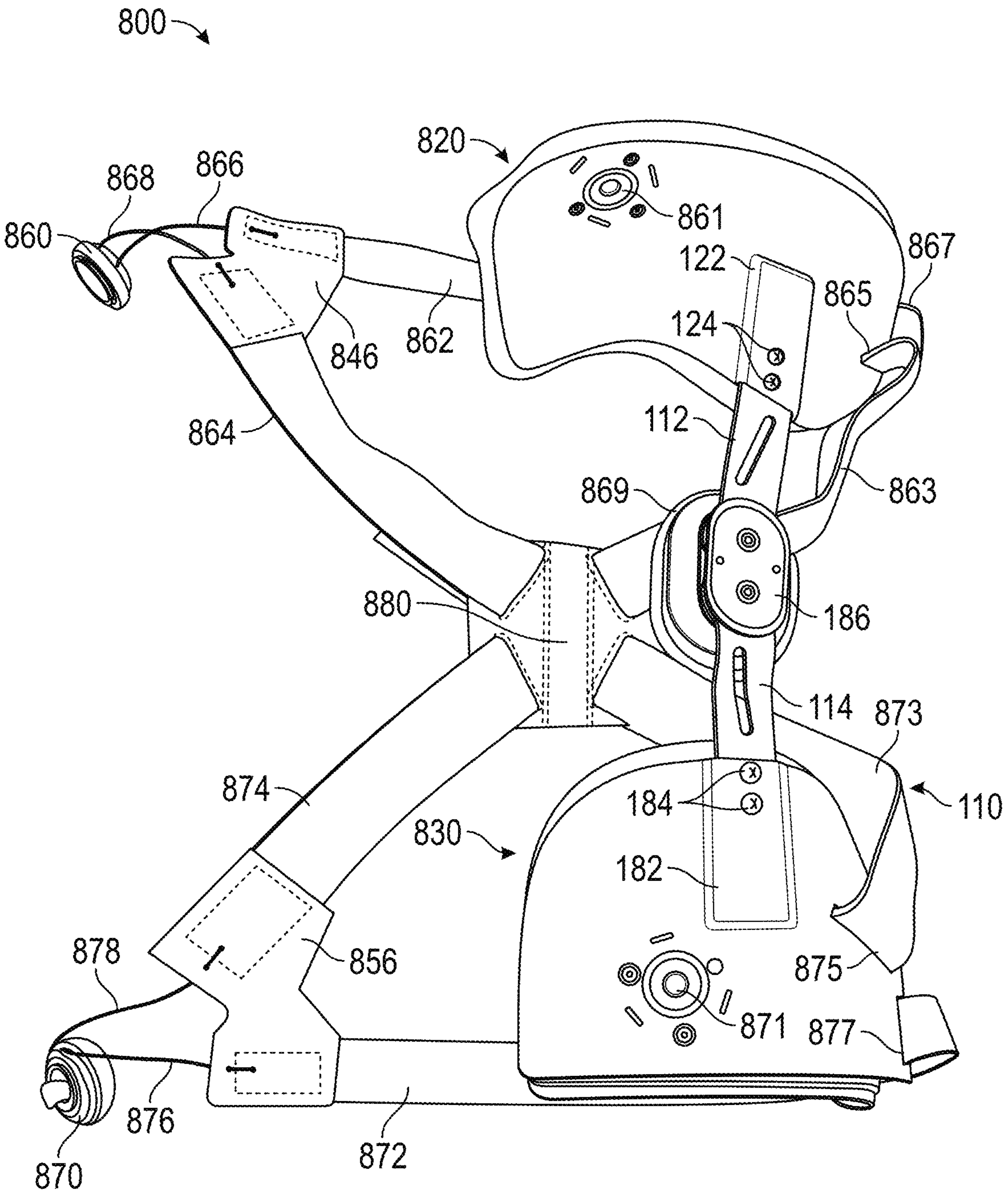
FIG. 8 illustrates a perspective view of another brace for use in the treatment of osteoarthritis in an unfastened orientation, in accordance with some embodiments.
Figure 9:
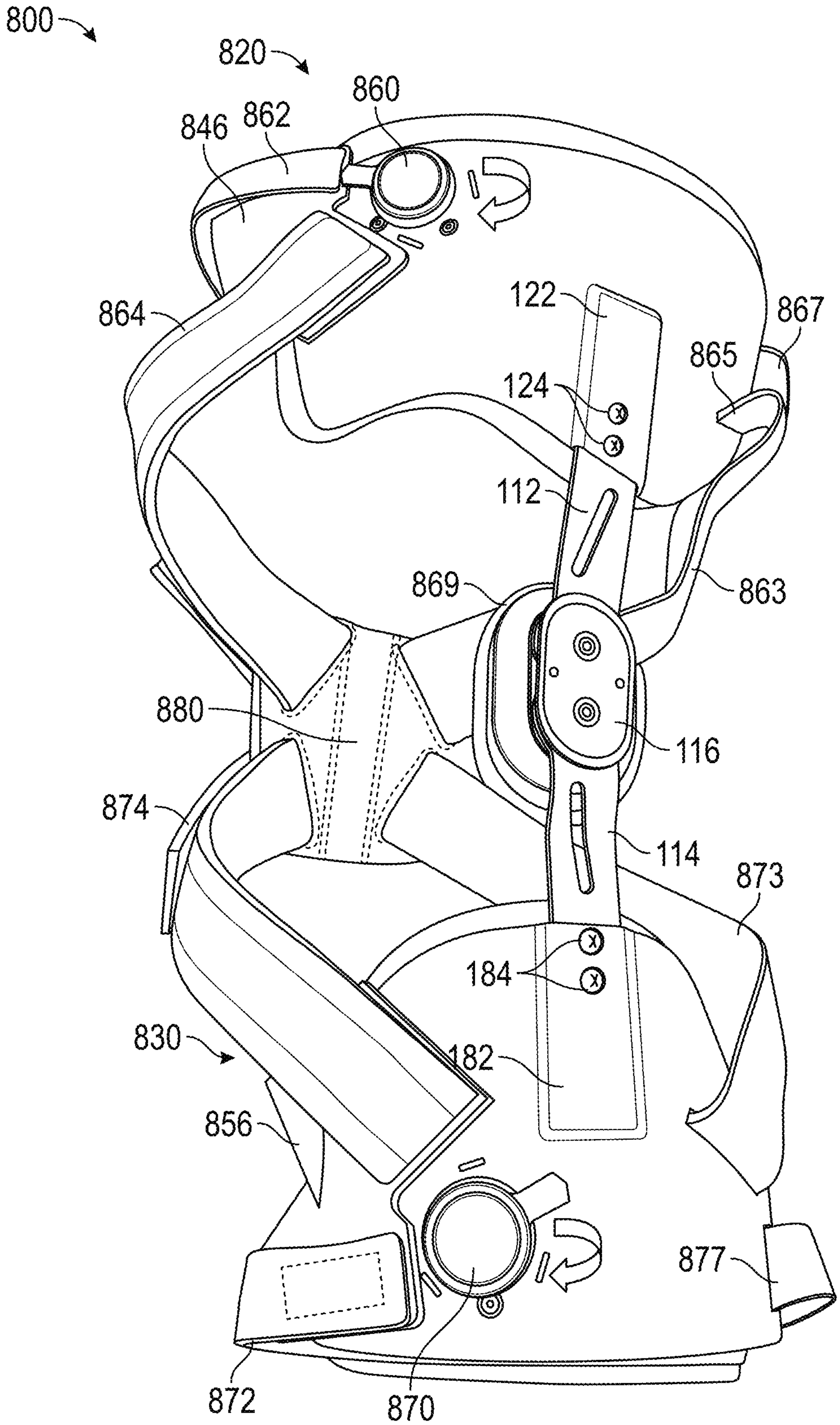
FIG. 9 illustrates the brace of FIG. 8 in a fastened orientation, in accordance with some embodiments.

At least one strap 762 is releasably coupled to strap receiver element 746 via any suitable mechanism described herein, for example utilizing a post/head and aperture arrangement that does or does not utilize magnetic coupling, as described in connection with at least FIG. 1, by coupling receiver strap element 746 with a lace coupled to and/or disposed on, over or within strap 762 (not shown in FIG. 7, but for example as shown and described in connection with FIG. 1), as illustrated in FIGS. 8-9, or any way otherwise known. Another end of strap 762 may be coupled to a portion of cuff 720 (or of a brace of which cuff 720 forms a portion) that is not visible in FIG. 7.

Accordingly, as shown in FIG. 7, strap 762 is releasably couplable to the quick-release buckle (comprising at least portions of one or more of lever arm(s) 741, extension arm 743 and/or strap receiver element 746) while the quick-release buckle itself is permanently and not releasably coupled to the frame of which cuff 720 forms a portion. In operation, a user may releasably couple strap 762 to strap receiver element 746. The user may then pivot lever arm(s) 741 maximally to the right in FIG. 7 about anchor point(s) 742 to a locked orientation, from any other unlocked orientation in which lever arm(s) 741 are not pivoted maximally to the right in FIG. 7. As shown in FIG. 7, transitioning lever arm(s) 741 from any unlocked orientation to the locked orientation causes extension 743 to shift to the right, which pulls strap receiver element 746 to the right, which pulls releasably connected strap 762 to the right, thereby increasing a tension in strap 762 and pulling cuff 720 against a desired portion of the user's body. Contrarily, transitioning lever arm(s) 741 from the locked orientation to any unlocked orientation causes extension 743 to shift to the left, which pushes strap receiver element 746 to the left, which releases strap 762 from strap receiver element 746 and/or decreases tension in strap 762 and releases cuff 720 from the desired portion of the user's body.

FIG. 8 illustrates a perspective view of a brace 800, comprising one or more magnetic winch mechanisms, in accordance with some embodiments. Brace 800 includes upright 110, comprising upper rigid support 112, lower rigid support 114, and hinge 116, which physically couples upper rigid support 112 and lower rigid support 114 as previously described in connection with FIG. 1. In some embodiments according to FIG. 8, upright 110 or brace 800 may further comprise a condyle pad 869 permanently, adjustably and/or removably coupled and/or couplable to a knee-facing side of hinge 116 and/or a case thereof. While not shown in FIG. 1, brace 100 may also include condyle pad 869.

Brace 800 further comprises an upper cuff 820 and a lower cuff 830. Upper and lower cuffs 820, 830 may be substantially similar to respective upper and lower cuffs 120, 130, however, not including respective recesses 126, 136 and also comprising one or more of the features described below. Upper cuff 820 is coupled to upper rigid support 112 utilizing one or more fasteners 124, e.g., screws or rivets secured through pocket 122 and the upper end of upper rigid support 112. Lower cuff 830 is coupled to lower rigid support 114 utilizing one or more fasteners 134, e.g., screws or rivets secured through pocket 132 and the lower end of lower rigid support 114.

Brace 800 further comprises straps 862-864 and 872-874, each coupled to at least one of upper cuff 820 and lower cuff 830. For example, as illustrated in FIG. 8, a first end of strap 862 is disposed toward ratcheting dial 860 and lace 866, which is disposed on, over, and/or within at least a portion of strap 862, extends from the first end of strap 862 and couples to ratcheting dial 860. A second end of first upper strap 862 is coupled to a slit 867 in a posterior portion of upper cuff 820. In some embodiments, slit 867 may comprise a d-ring or other suitable fastening means. Strap 862 is configured to extend substantially horizontally between its first and second ends around a side of the user's thigh when brace 800 is properly worn by the user and the user is standing. Strap 862 may be considered a proximal strap of upper cuff 820.

A first end of strap 864 is disposed toward ratcheting dial 860 and lace 868, which is disposed on, over, and/or within at least a portion of strap 864, extends from the first end of strap 864 and couples to ratcheting dial 860. In some embodiments, first ends of straps 862,864 may be coupled to an intermediate bracket 846. In some embodiments, intermediate bracket 846 comprises fabric, leather, plastic or any other suitable type of material. In some embodiments, laces 866,868 are coupled to and/or terminate at respective locations of intermediate bracket 846. In some such embodiments, laces 866,868 may be attached to the respective strap(s) and/or bracket utilizing an overhand knot, a figure-eight knot or any other suitable knot or fixation process. Strap 864 extends diagonally and a second end of strap 864 is adjustably and/or permanently coupled to a central harness or central harness 880.

In some embodiments, central harness 880 comprises a fabric, leather, or any other suitable material. In some embodiments, central harness 880 comprises a plurality of slits, each configured to receive and adjustably and/or permanently anchor an end of a corresponding one of straps 863, 864, 873, 874. In some embodiments, central harness 880 is configured to be disposed immediately adjacent the user's knee, e.g. directly against the skin and/or clothing of the user, when brace 800 is properly worn by the user.

A first end of strap 863 is coupled to a slit 865 in the posterior portion of upper cuff 820. In some embodiments, slit 865 may comprise a d-ring or other suitable fastening means. Strap 863 is configured to extend diagonally, between its first and second ends, around a posterior portion of the user's thigh toward central harness 880. A second end of strap 863 is adjustably and/or permanently coupled to central harness 880, e.g., via one of the plurality of slits disposed therein. Straps 863,864 may be considered distal straps of upper cuff 820.

A first end of strap 872 is disposed toward ratcheting dial 870 and lace 876, which is disposed on, over, and/or within at least a portion of strap 872, extends from the first end of strap 872 and couples to ratcheting dial 870. A second end of first upper strap 872 is coupled to a slit 877 in a posterior portion of lower cuff 830. In some embodiments, slit 877 may comprise a d-ring or other suitable fastening means. Strap 872 is configured to extend substantially horizontally between its first and second ends around a side of the user's lower leg when brace 800 is properly worn by the user and the user is standing. Strap 872 may be considered a proximal strap of lower cuff 830.

A first end of strap 874 is disposed toward ratcheting dial 870 and lace 878, which is disposed on, over, and/or within at least a portion of strap 874, extends from the first end of strap 874 and couples to ratcheting dial 870. In some embodiments, first ends of straps 872, 874 may be coupled to a bracket 856. In some embodiments, bracket 856 comprises fabric, leather, plastic or any other suitable type of material. In some embodiments, laces 876, 878 are coupled to and/or terminate at respective locations of bracket 856. Strap 874 extends diagonally and a second end of strap 874 is adjustably and/or permanently coupled to central harness 880, e.g., via one of the plurality of slits disposed therein.

A first end of strap 873 is coupled to a slit 875 in the posterior portion of lower cuff 830. In some embodiments, slit 875 may comprise a d-ring or other suitable fastening means. Strap 873 is configured to extend diagonally, between its first and second ends, around a posterior portion of the user's lower leg toward central harness 880. A second end of strap 873 is adjustably and/or permanently coupled to central harness 880, e.g., via one of the plurality of slits disposed therein. Straps 873, 874 may be considered distal straps of lower cuff 830.

Rather than utilizing tensioning mechanism 140, having quick-release buckle 141 and its related components 142, 149 (as with at least brace 100 in FIG. 1), brace 800 comprises one or more Fidlock winch mechanisms. For example, brace 800 comprises ratcheting dials 860, 870 configured to be directly releasably and adjustably coupled to respective magnetic bases 861, 871 on upper cuff 820 and lower cuff 830. In some embodiments, magnetic bases 861, 871 are disposed on a portion of respective upper cuff 820 and lower cuff 830 (or slightly anterior of a midline of the respective cuff). In some embodiments, at least a portion of ratcheting dials 860, 870 and magnetic bases 861, 871 comprises PA6, PA6 GF15, ABS, TPU, NbFeB and/or epoxy.

Magnetic bases 861, 871 may be stitchable, glueable, and/or otherwise attachable to their respective cuffs. For example, in some embodiments, magnetic bases 861, 871 may each be attached to their respective cuffs using a zipper presser foot and a stich length of 2-3 mm at a position immediately adjacent Fidlock portion to maximize stability of the attachment. Magnetic bases 861, 871 may each comprise at least a portion that is magnetic or that is attracted to a magnet. In some embodiments, magnetic bases 861, 871 each comprise a post 1400 (see FIG. 14) configured to mate with respective ratcheting dials 860, 870.

Figure 14:
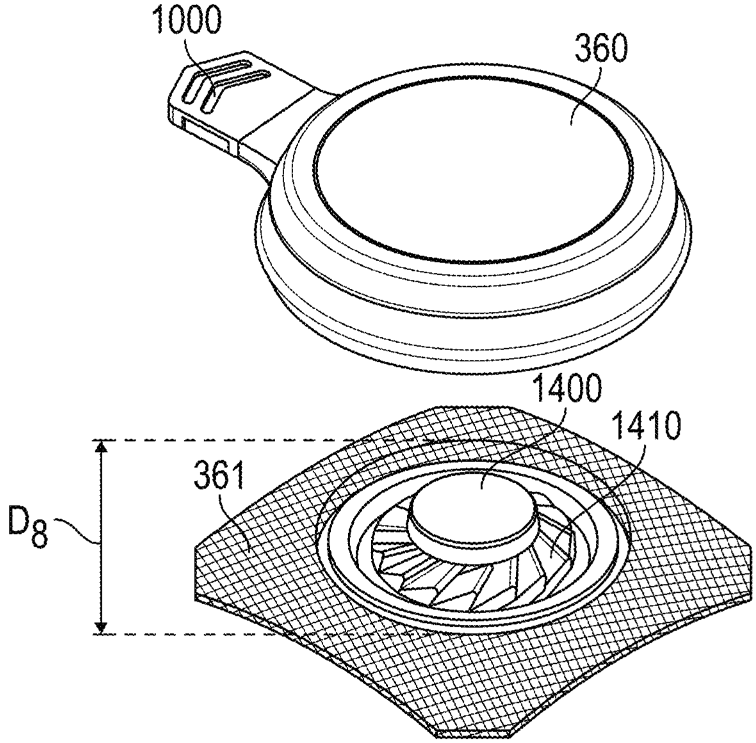
FIG. 14 illustrates an exploded perspective view of the magnetic winch mechanism of FIG. 10, in accordance with some embodiments.

Each of ratcheting dials 860, 870 comprises a winching mechanism coupled to respective laces 866,868 or 876, 878. Each of ratcheting dials 860, 870 also comprises a portion that is magnetic or, where magnetic bases 861,371 are magnetic, that is at least attracted to a magnet. Each of ratcheting dials 860, 870 is configured to mate with the corresponding magnetic base 861, 871 (for example post 1400 as shown in FIG. 14).

In operation, a user may don brace 800 by aligning upright 110 against a side of his or her leg such that hinge 116 is approximately aligned immediately adjacent the knee. The user may grasp ratcheting dial 860 and pull it, straps 862-864, and central harness 880 around a side of the user's leg and attach ratcheting dial 860 to magnetic base 861. When ratcheting dial 860 is brought sufficiently near to magnetic base 861, ratcheting dial 860 and magnetic base 861 will automatically align and snap together by virtue of the alignment between their mutual magnetic portions. To achieve a desired amount of tension, the user may twist ratcheting dial 860, which pulls on and increases a tension in laces 866,868, which increases a tension in one or more of straps 862-864, thereby adjusting support provided by and a fit of upper cuff 820.

Figure 4:
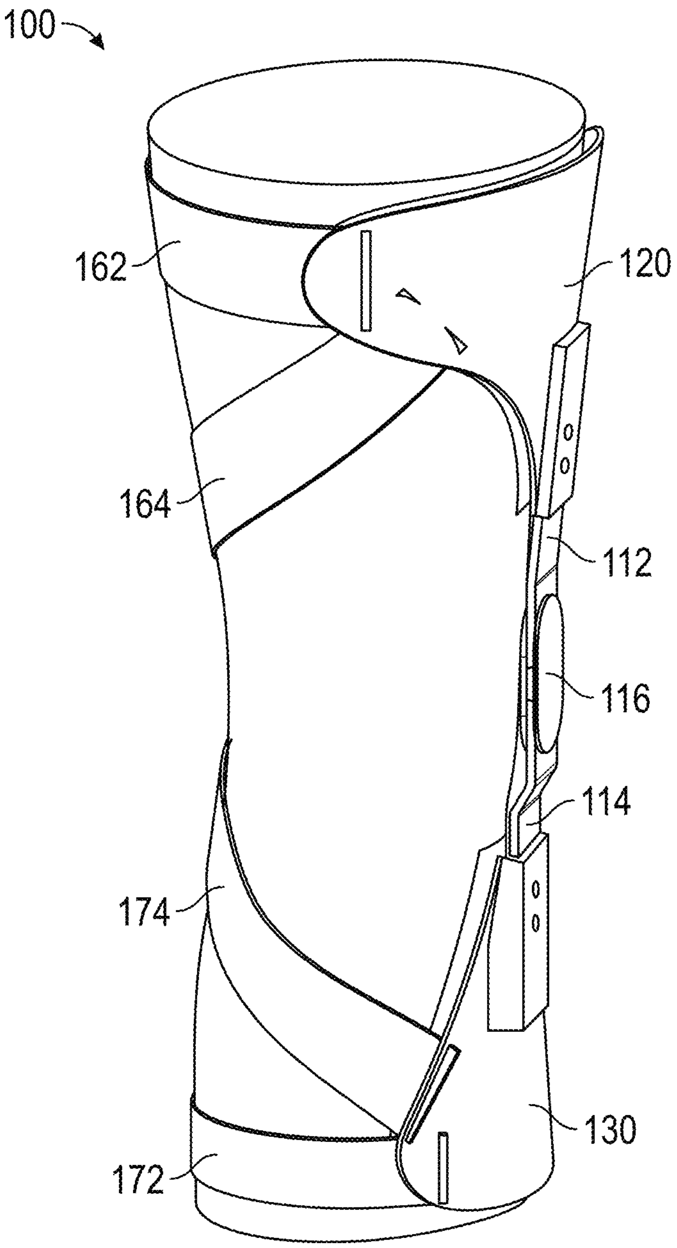
FIG. 4 illustrates a perspective view of the brace of FIGS. 2 and 3 as viewed from yet another angle, in accordance with some embodiments.
Figure 5:
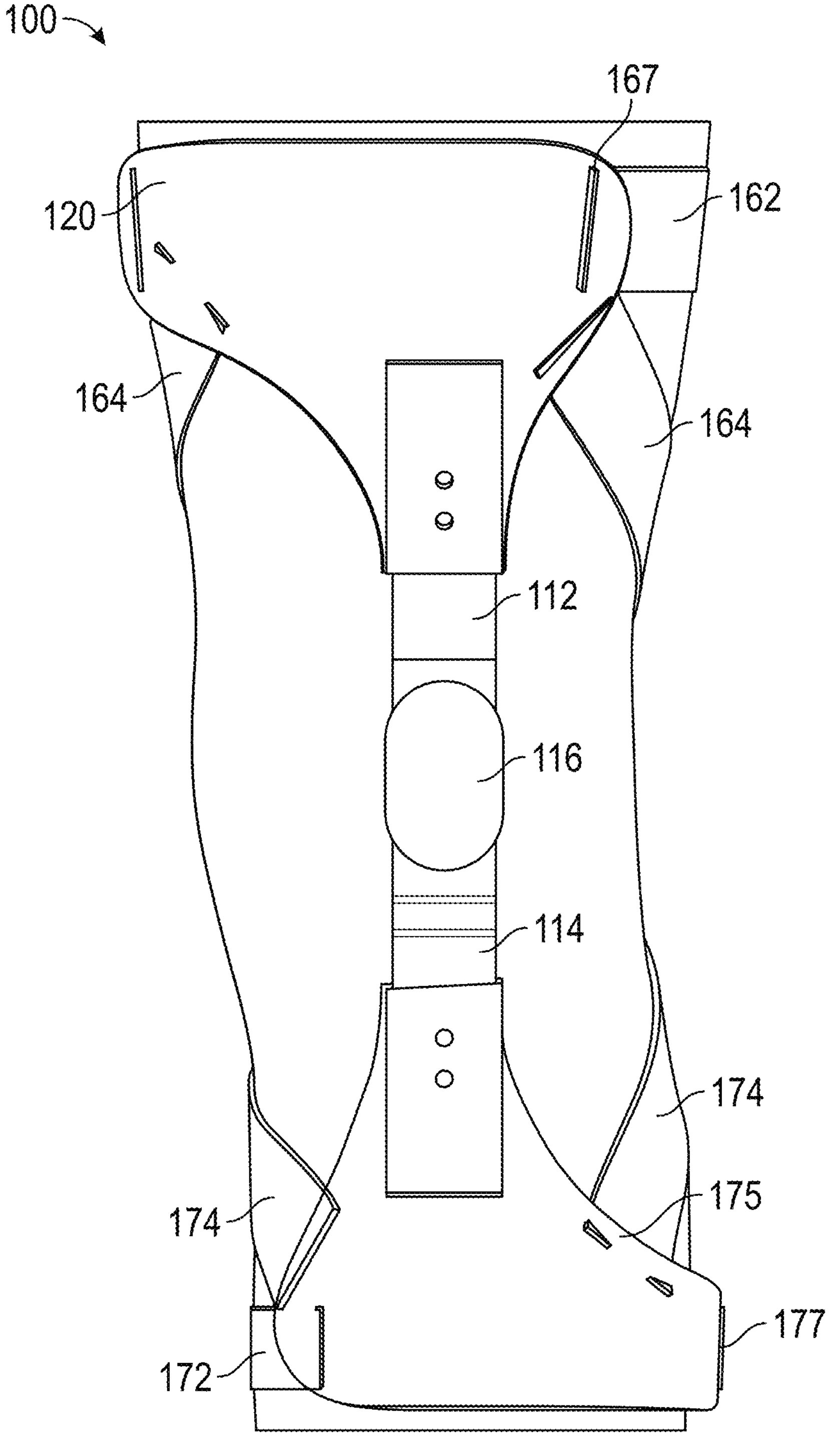
FIG. 5 illustrates a side view of the brace of FIGS. 2-4, in accordance with some embodiments.

The user may grasp ratcheting dial 870 and pull it, straps 872-874, and central harness 880 around a side of the user's leg and attach ratcheting dial 870 to magnetic base 871. When ratcheting dial 870 is brought sufficiently near to magnetic base 871, ratcheting dial 870 and magnetic base 871 will automatically align and snap together by virtue of the alignment between their mutual magnetic portions. To achieve a desired amount of tension, the user may twist ratcheting dial 870, which pulls on and increases a tension in laces 876, 878, which increases a tension in one or more of straps 872-874, thereby adjusting support provided by and a fit of lower cuff 830. FIG. 4 illustrates brace 800 when ratcheting dials 860, 870 are coupled to their respective magnetic bases 861, 871. The arrows in FIG. 4 illustrate an example direction in which each of ratcheting dials 860, 870 may be twisted to increase a tension in one or more of the laces and/or straps. In some embodiments, ratcheting dials 860, 870 may each comprise a locking mechanism (not shown) configured to prevent accidental removal or release of ratcheting dials 860, 870 from their respective magnetic bases 861, 871.

Ratcheting dials 860, 870 comprising the attaching feature and also itself functioning as the tightening feature greatly reduces the complexity of brace 800 over other braces in a novel and inventive way. Moreover, by virtue of this same melding of multiple, previously unrelated functions into a single feature, a user may attach brace 800 and then tighten it without ever taking his or her hand off of ratcheting dials 860, 870. This greatly increases the simplicity of use, which has a strong positive effect on the compliance rate of users, especially for elderly users suffering from OA and who need a brace that's maximally easy to regularly put on, adjust and use.

FIGS. 10-15 illustrate several different views and orientations of an example Fidlock winch mechanism, in accordance with some embodiments. While ratcheting dial 860 and magnetic base 861 are shown in FIGS. 10-15, similar form and/or function are present in ratcheting dial 870 and magnetic base 871 and/or in ratcheting dials 160, 170, of FIG. 1, which may comprise similar features to those of dial 860 and base 861 when integrated into a single part. While example dimensions are provided for different aspects of ratcheting dial 860 and magnetic base 861, the present disclosure is not so limited and contemplates any other suitable dimensions.

Figure 11:
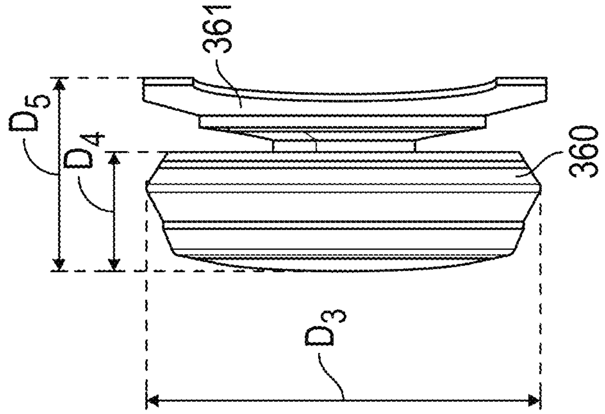
FIG. 11 illustrates a first side view of the magnetic winch mechanism of FIG. 10, in accordance with some embodiments.
Figure 13:
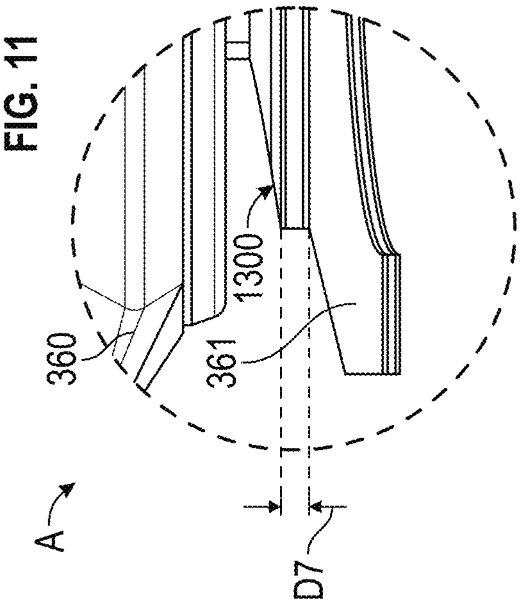
FIG. 13 illustrates a magnified portion A of the magnetic winch mechanism from FIG. 12, in accordance with some embodiments.
Figure 10:
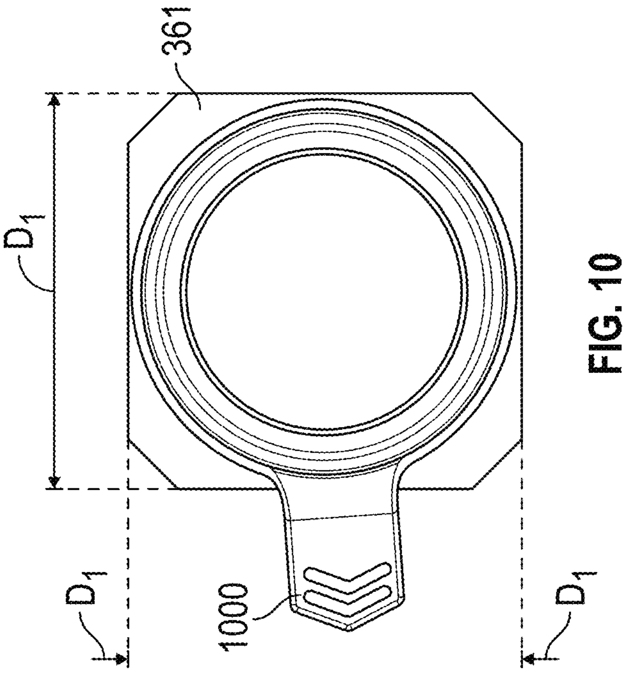
FIG. 10 illustrates a top view of a magnetic winch mechanism for use in any brace for treatment of osteoarthritis, in accordance with some embodiments.
Figure 12:
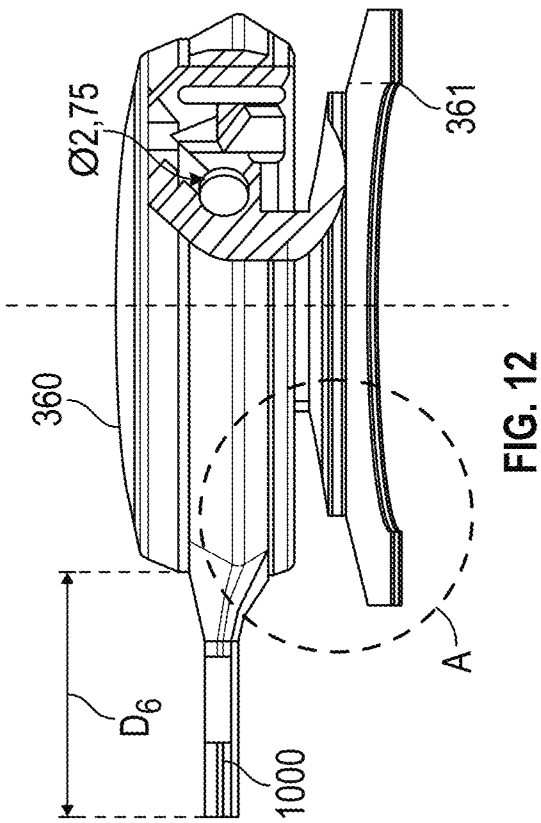
FIG. 12 illustrates a second side view, orthogonal to each of the FIGS. 10 and 11 views, of the magnetic winch mechanism of FIG. 10, in accordance with some embodiments.

As illustrated in FIG. 10, magnetic base 861 may have a first dimension $D_1$ and a second, orthogonal dimension $D_2$. In some embodiments, each of $D_1$ and $D_2$ are 85 millimeters (mm). As illustrated in FIG. 11, ratcheting dial 860 may have a diameter $D_3$ of 84 mm and a height $D_4$ of 10.5 mm. When in the fixed orientation, ratcheting dial 860 and magnetic base 861 may have a combined height $D_5$ of 16.8 mm. In some embodiments, ratcheting dial 860 comprises a pull tab 1000 configured to release ratcheting dial 860 from magnetic base 861 when tension is applied to pull tab 1000. In some embodiments, pull tab 1000 has a length $D_6$ of 14.3 mm. In some embodiments, ratcheting dial 860 comprises an elastomeric o-ring configured to compress while receiving at least a portion of magnetic base 861, thereby retaining magnetic base 861 in the attached orientation. In some embodiments, the o-ring has a thickness of approximately 2.75 mm. In some embodiments, magnetic base 861 comprises a central portion that is raised by an amount $D_7$ compared to a perimeter of magnetic base 861. In some embodiments, as illustrated by FIG. 13, $D_7$ may be approximately 1.3 mm and represents a thickness of material that may be disposed over the perimeter of magnetic base 861, for example before, during or after permanently attaching magnetic base 861 to upper cuff 820, without extending above the top surface of the central portion of magnetic base 861.

Figure 15:
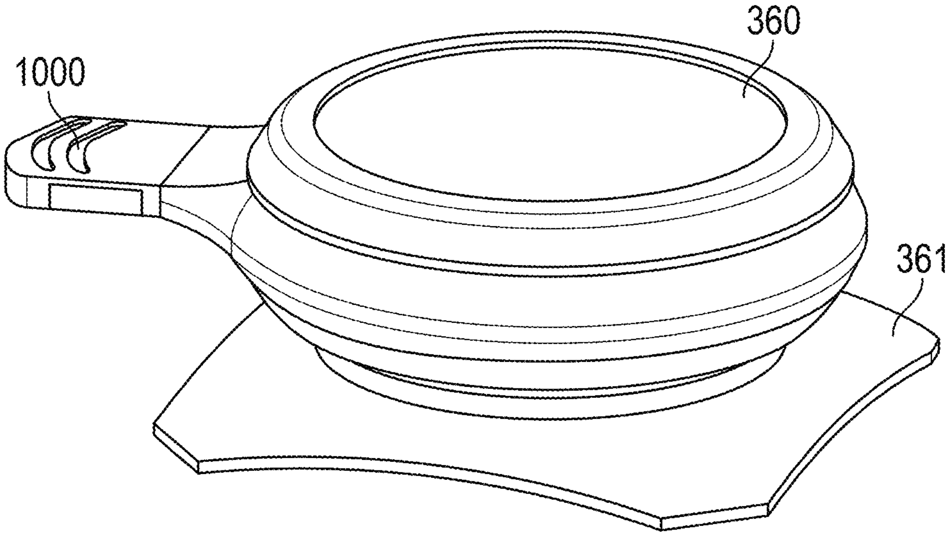
FIG. 15 illustrates a perspective view of the assembled magnetic winch mechanism of FIG. 10 in a fastened orientation, in accordance with some embodiments.

In operation, ratcheting dial 860 may be held by the user and then pressed down onto magnetic base 861, for example down onto post 1400 such that a plurality of fins 1410 are in contact with a mating ratcheting mechanism (not shown) within ratcheting dial 860. As described above, since both are magnetic, when ratcheting dial 860 is placed sufficiently close to magnetic base 861 (for example as shown in FIG. 14), the two will be automatically magnetically attracted to one another and to the correct mutual alignment (for example as shown in FIG. 15). Once fixed together, the mutual magnetic attraction will also help to retain rotating ratcheting dial 860 on magnetic base 861. And rotating ratcheting dial 860 in a particular direction with respect to magnetic base 861 will increase a tension in laces attached thereto. To release the tension in the laces, the user need only apply sufficient tension to tab 1000 to separate ratcheting dial 860 from magnetic base 861.

Figure 16:
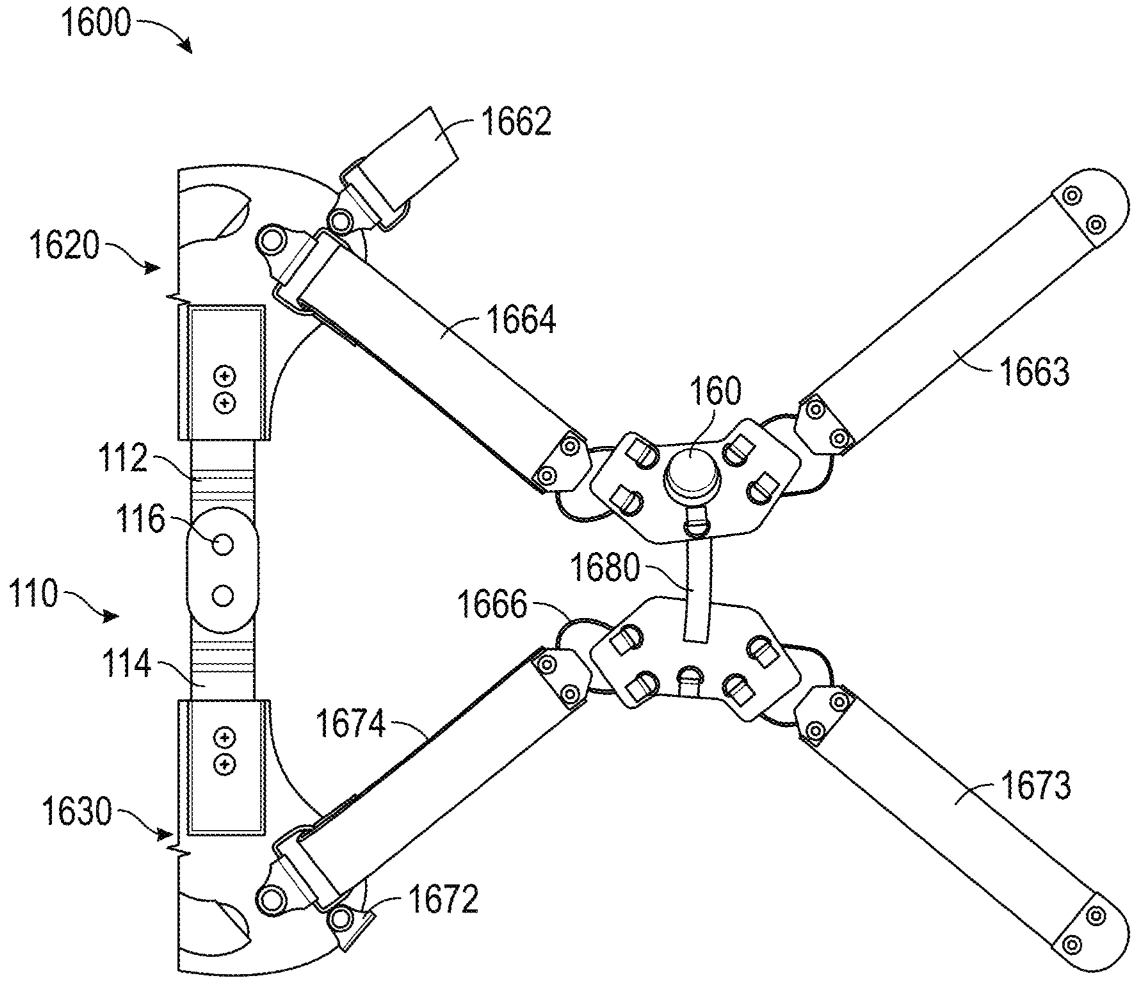
FIG. 16 illustrates a perspective view of another brace for use in the treatment of osteoarthritis in an unfastened orientation, in accordance with some embodiments.
Figure 17:
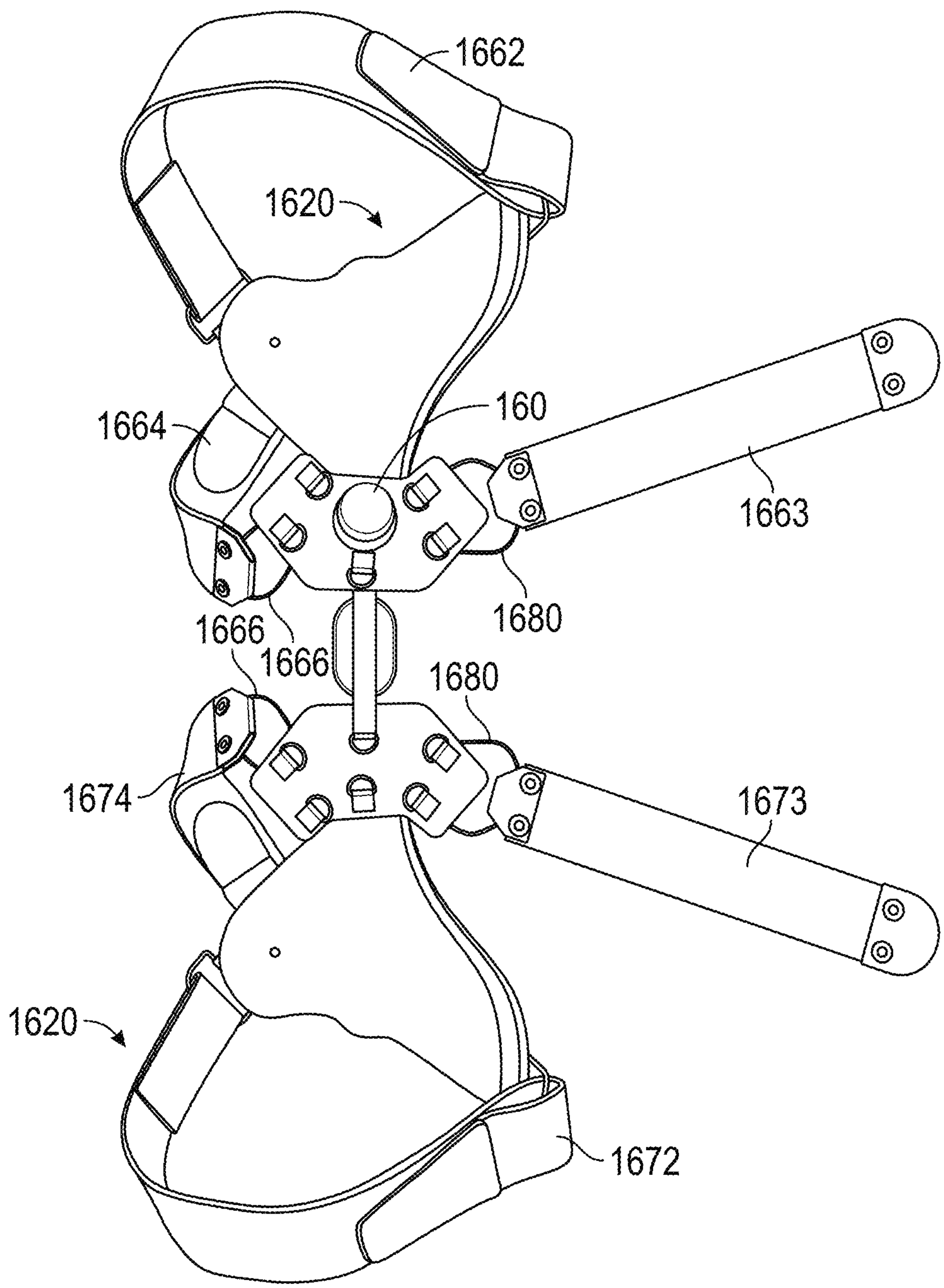
FIG. 17 illustrates another perspective view of the brace of FIG. 16 in an unfastened orientation, in accordance with some embodiments.
Figure 18:
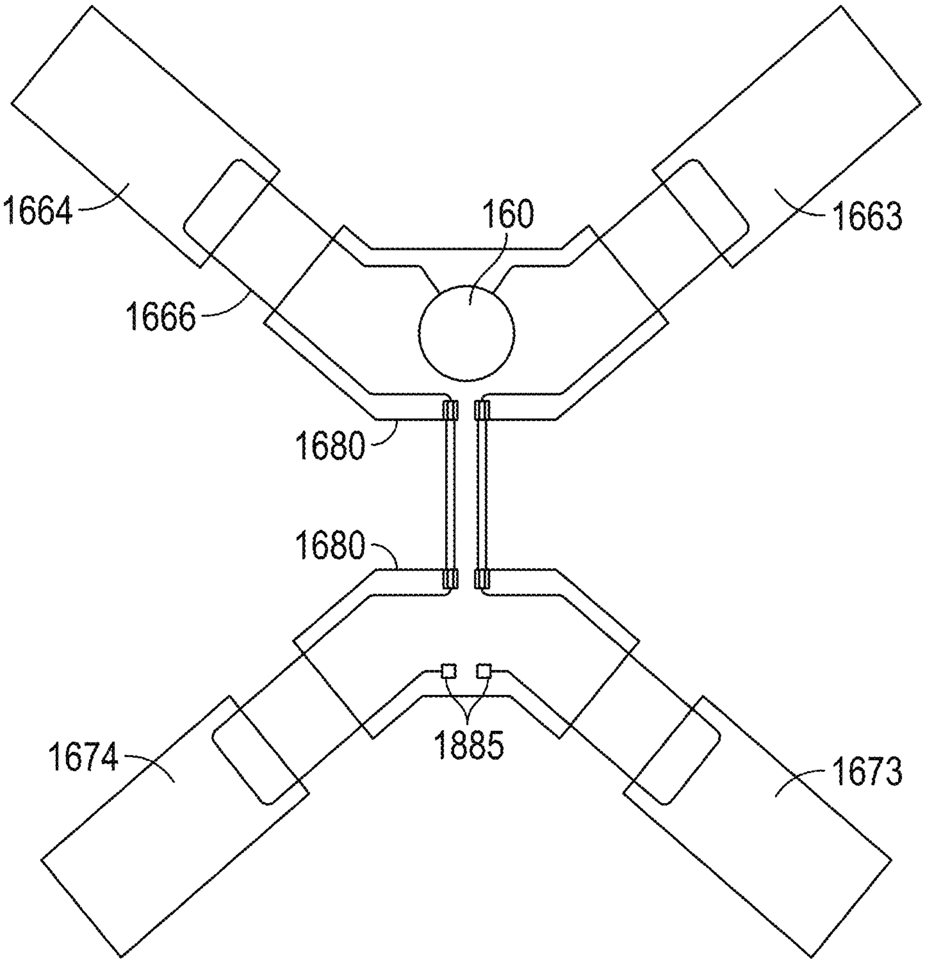
FIG. 18 illustrates a magnified view of the central harness of the brace of FIG. 16, in accordance with some embodiments.

FIG. 16 illustrates a perspective view of a brace 1600, comprising one or more winch mechanisms, in accordance with some embodiments. FIG. 17 illustrates the brace 1600 of FIG. 16 from another view, in accordance with some embodiments. And FIG. 18 illustrates a pathway for a lace 1666 used to adjust a tension in one or more straps of brace 1600. Brace 1600 includes upright 110, comprising upper rigid support 112, lower rigid support 114, and hinge 116, which physically couples upper rigid support 112 and lower rigid support 114 as previously described in connection with at least FIG. 1.

Brace 1600 further comprises a upper cuff 1620 and a lower cuff 1630, which may be substantially similar to respective upper and lower cuffs 820, 830 of FIGS. 8 and 9, however comprising one or more of the features described below. Upper cuff 1620 is coupled to upper rigid support 112 utilizing one or more fasteners, e.g., screws or rivets secured through a pocket and the upper end of upper rigid support 112, while lower cuff 1630 is similarly coupled to lower rigid support 114 utilizing one or more fasteners, e.g., screws or rivets secured through a pocket and the lower end of lower rigid support 114, for example as previously described in connection with at least FIGS. 8 and 9.

Brace 1600 further comprises straps 1662-1664 and 1672-1674, each coupled to at least one of upper cuff 1620 and lower cuff 1630. In FIGS. 16 and 17, one or more straps are coupled and/or couplable to upper cuff 1620 or lower cuff 1630 utilizing D-rings. However, the present disclosure is not so limited and any other suitable method of coupling may also be utilized. For example, as illustrated in FIG. 16, a first end of strap 1662 is coupled to a posterior portion of upper cuff 1620. A second end of strap 1662 is releasably coupleable to an anterior portion of upper cuff 1620. Strap 1662 is configured to extend substantially horizontally between its first and second ends around a side of the user's thigh when brace 1600 is properly worn by the user and the user is standing. Strap 1662 may be considered a proximal strap of upper cuff 1620.

A first end of strap 1672 is coupled to a posterior portion of lower cuff 1630. A second end of strap 1672 is releasably coupleable to an anterior portion of lower cuff 1630. Strap 1672 is configured to extend substantially horizontally between its first and second ends around a side of the user's lower leg when brace 1600 is properly worn by the user and the user is standing. Strap 1672 may be considered a distal strap of lower cuff 1630.

Each of straps 1663, 1664, 1673, 1674 are configured to extend diagonally between their first and second ends. A first end of strap 1664 is coupled to a posterior portion of upper cuff 1620 and a second end of strap 1664 is adjustably and/or permanently coupled to a central harness 1680 via at least a lace 1666. A first end of strap 1674 is coupled to a posterior portion of lower cuff 1630 and a second end of strap 1674 is adjustably and/or permanently coupled to central harness 1680 via at least lace 1666. A first end of strap 1663 is coupleable to an anterior portion of upper cuff 1620 and a second end of strap 1663 is adjustably and/or permanently coupled to central harness 1680 via at least lace 1666. A first end of strap 1673 is coupleable to an anterior portion of lower cuff 1630 and a second end of strap 1673 is adjustably and/or permanently coupled to central harness 1680 via at least lace 1666. Lace 1666 is configured to pass back and forth between central harness 1680 and a second end of each of straps 1664, 1663, 1674, 1673. Straps 1663,1664 may be considered distal straps of upper cuff 1620, while straps 1673,1674 may be considered proximal straps of lower cuff 1630.

In some embodiments, central harness 1680 comprises a fabric, leather, or any other suitable material. In some embodiments, central harness 1680 is configured to be disposed immediately adjacent the user's knee when brace 1600 is properly worn by the user.

Rather than utilizing tensioning mechanism 140, having quick-release buckle 141 and its related components 142-149 (as with at least brace 100 in FIG. 1), brace 1600 comprises one or more Fidlock winch mechanisms. For example, brace 1600 comprises at least ratcheting dial 160 disposed on central harness 1680. In some embodiments, ratcheting dial 160 is substantially as described in connection with any figure herein.

Ratcheting dial 160 comprises a winching mechanism coupled to lace 1666. In operation, a user may don brace 1600 by aligning upright 110 against a side of his or her leg such that hinge 116 is approximately aligned immediately adjacent the knee. The user may pull straps 1662-1664 and 1672-1674, adjustably coupled to central harness 1680, around a side of the user's leg and attach the first ends of one or both of straps 1663 and 1673 to the respective anterior portions of upper cuff 1620 and lower cuff 1630. The use may also attach the first ends of one or both of straps 1662, 1672 to the respective anterior portions of upper cuff 1620 and lower cuff 1630. To achieve a desired amount of tension, the user may twist ratcheting dial 160, which pulls on and increases a tension in lace 1666, which increases a tension in one or more of straps 1663, 1664, 1673, 1674 thereby adjusting support provided by and a fit of brace 1600. This functionality may be at least in part a result of how lace 1666 is threaded between straps 1663, 1664, 1673, 1674 and central harness 1680. As illustrated in FIG. 18, each end of lace 1666 may terminate at a respective anchor point 1885 disposed on central harness 1680. From a first end, lace 1666 extends from the leftmost anchor point 1885 to second end of strap 1674 and back to central harness 1680. Lace 1666 further extends across a neck of central harness 1680, to second end of strap 1664, back to central harness 1680, and into ratcheting dial 160. From ratcheting dial 160, lace 166 further extends to second end of strap 1663 and back to central harness 1680. Lace 1666 further extends across the neck of central harness 1680 to second end of strap 1673, back to central harness 1680 and terminates at the rightmost anchor 1885.

Ratcheting dial 160 being coupled to lace 1666, which itself is strung back and forth between each of straps 1663, 1664, 1673, 1674 as described above, greatly reduces the complexity of brace 1600 compared to other braces in a novel and inventive way at least in that a tension in each of straps 1663, 1664, 1673, 1674 may be simultaneously adjusted by twisting ratcheting dial 160.

Figure 19:
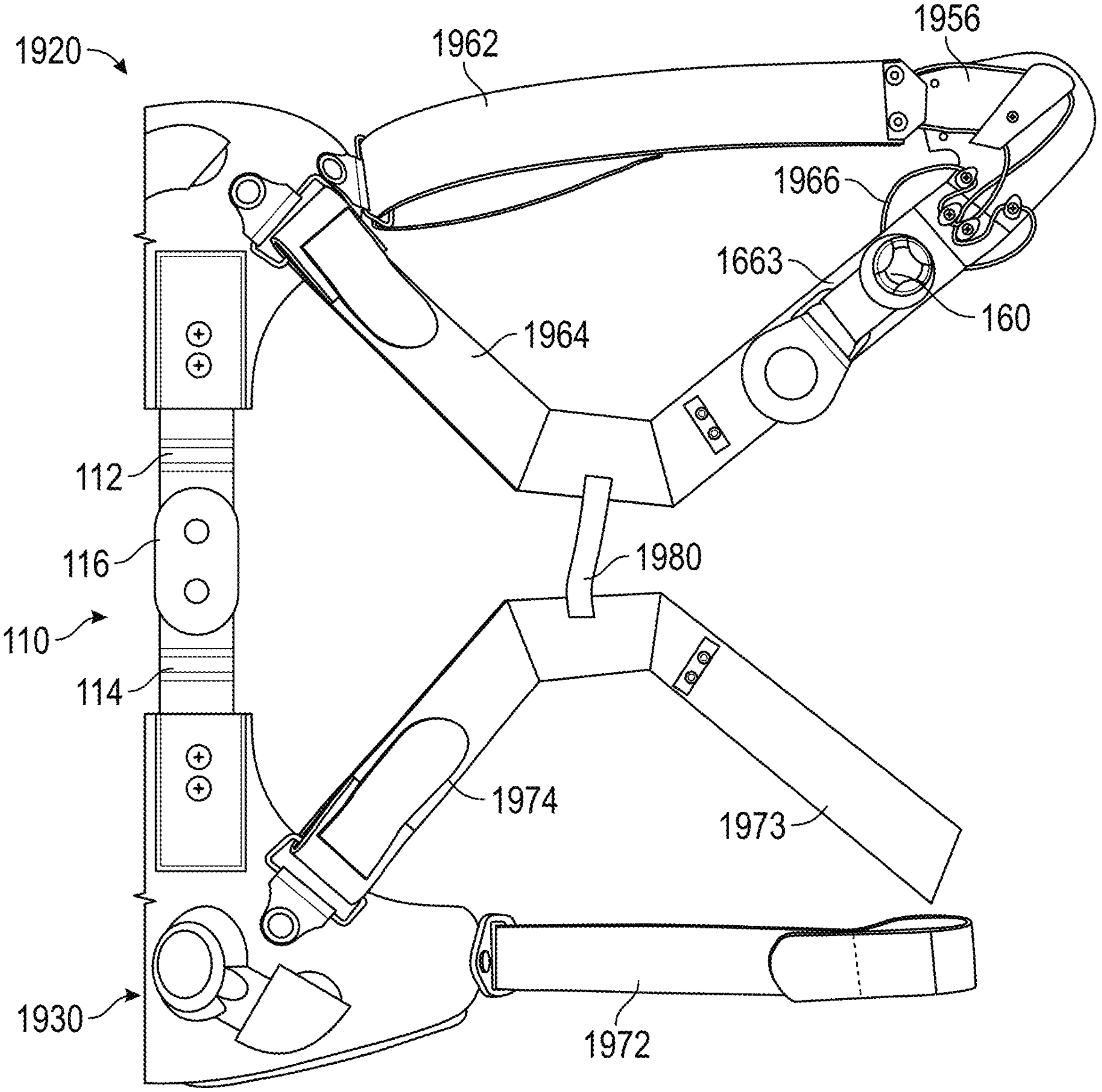
FIG. 19 illustrates a perspective view of yet another brace for use in the treatment of osteoarthritis in an unfastened orientation, in accordance with some embodiments.
Figure 20:
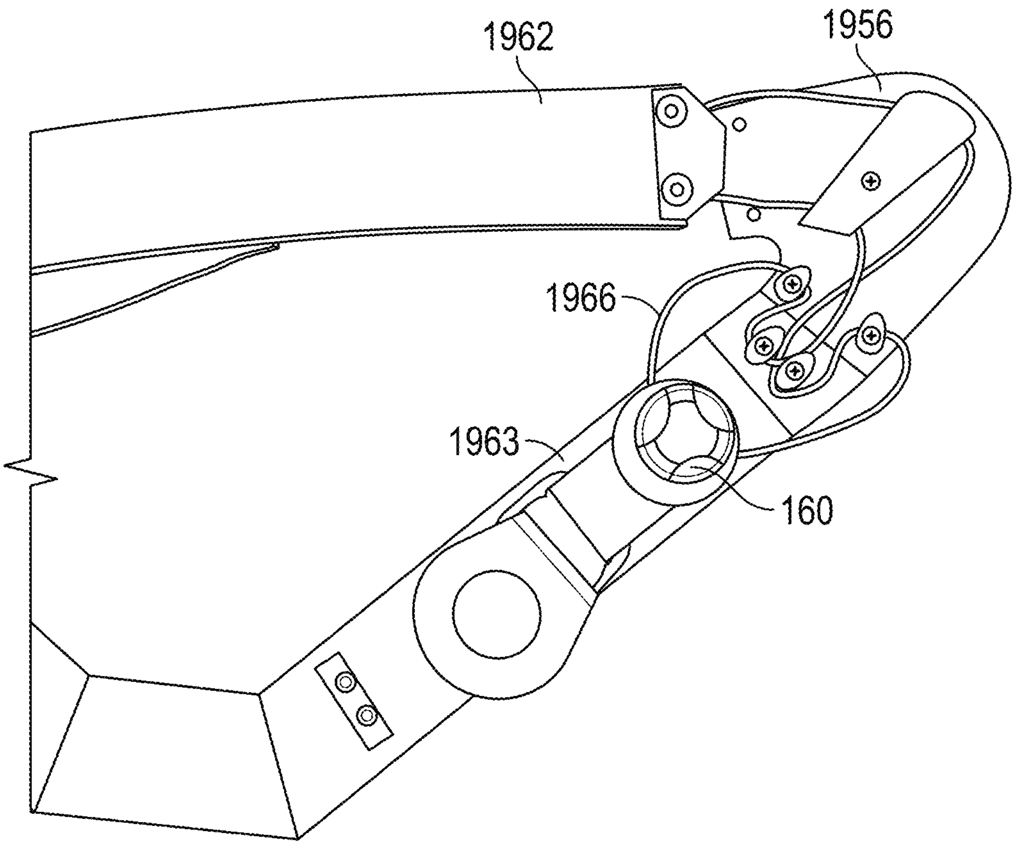
FIG. 20 illustrates a magnified view of a portion of the brace of FIG. 19, in accordance with some embodiments.
Figure 21:
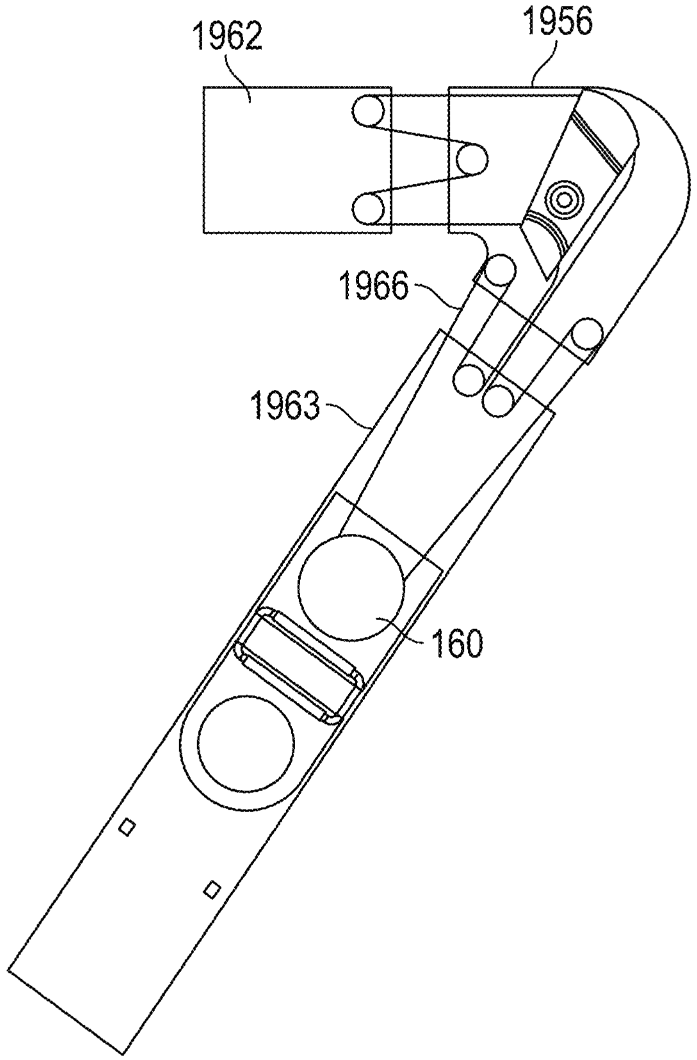
FIG. 21 illustrates a magnified view of a portion of the brace of FIG. 19, in accordance with some embodiments.

FIG. 19 illustrates a perspective view of a brace 1900, comprising one or more winch mechanisms, in accordance with some embodiments. FIG. 20 illustrates a magnified portion of brace 1900 of FIG. 19, in accordance with some embodiments. And FIG. 21 illustrates a pathway for a lace 1966 used to adjust a tension in one or more straps of brace 1900. Brace 1900 includes upright 110, comprising upper rigid support 112, lower rigid support 114, and hinge 116, which physically couples upper rigid support 112 and lower rigid support 114 as previously described in connection with at least FIG. 1.

Brace 1900 further comprises a upper cuff 1920 and a lower cuff 1930, which may be substantially similar to respective upper and lower cuffs 1620, 1630 of FIGS. 16-18, however comprising one or more of the features described below. Upper cuff 1920 is coupled to upper rigid support 112 utilizing one or more fasteners, e.g., screws or rivets secured through a pocket and the upper end of upper rigid support 112, while lower cuff 1930 is similarly coupled to lower rigid support 114 utilizing one or more fasteners, e.g., screws or rivets secured through a pocket and the lower end of lower rigid support 114, for example as previously described in connection with at least FIGS. 8 and 9.

Brace 1900 further comprises straps 1962-1664 and 1972-1674, each coupled to at least one of upper cuff 1920 and lower cuff 1930. In FIGS. 19, one or more straps are coupled and/or couplable to upper cuff 1920 or lower cuff 1930 utilizing D-rings. However, the present disclosure is not so limited and any other suitable method of coupling may also be utilized. As illustrated in FIG. 19, a first end of strap 1962 is coupled to a posterior portion of upper cuff 1920. A second end of strap 1962 is adjustably coupled to a bracket 1956 via a lace 1966 that is strung back and forth between the second end of strap 1962 and bracket 1956. Bracket 1956 is configured to be releasably and adjustably coupled to an anterior portion of upper cuff 1920. Strap 1962 is configured to extend substantially horizontally between its first and second ends around a side of the user's thigh when brace 1900 is properly worn by the user and the user is standing. Strap 1962 may be considered a proximal strap of upper cuff 1920.

A first end of strap 1972 is coupled to a posterior portion of lower cuff 1930. Though not shown in FIG. 19, in some embodiments, brace 1600 may further comprise another bracket, similar to bracket 1956, configured to similarly couple second ends of each of straps 1972 and 1973 via another lace. In some such embodiments, the bracket is configured to be releasably and adjustably coupled to an anterior portion of lower cuff 1930. In some other embodiments, a second end of strap 1972 is releasably coupleable to an anterior portion of lower cuff 1930 directly. In either embodiment, strap 1972 is configured to extend substantially horizontally between its first and second ends around a side of the user's lower leg when brace 1900 is properly worn by the user and the user is standing. Strap 1972 may be considered a distal strap of lower cuff 1930.

Each of straps 1963, 1964, 1973, 1974 are configured to extend diagonally between their first and second ends. A first end of strap 1964 is coupled to a posterior portion of upper cuff 1920 and a second end of strap 1964 is coupled directly to central harness 1980. A first end of strap 1974 is coupled to a posterior portion of lower cuff 1930 and a second end of strap 1974 is coupled directly to central harness 1980. A first end of strap 1963 is adjustably coupled to bracket 1956 via lace 1966 that is strung back and forth between the first end of strap 1963 and bracket 1956. A second end of strap 1963 is coupled directly to central harness 1980.

In embodiments where straps 1972, 1973 are coupled to one another via a bracket similar to bracket 1956, a first end of strap 1973 and a second end of strap 1972 are each adjustably coupled to the bracket via another lace, similar to lace 1966, substantially as described above for brace 1956 and straps 1962, 1963. In such embodiments, the bracket may be removably coupled to an anterior portion of lower cuff 1930. However, in embodiments not having such a second bracket, the first end of strap 1973 and the second end of strap 1972 may each be removably and adjustably coupled to respective anterior portions of lower cuff 1930.

As illustrated in more detail in FIGS. 20 and 21, lace 1966 is configured to pass back and forth between bracket 1956 and the second end of strap 1962 and back and forth between bracket 1956 and at least the first end of strap 1963. Strap 1963 further comprises ratcheting dial 160, which may be as previously described anywhere in this disclosure. Lace 1966 extends into ratcheting dial 160 and, when ratcheting dial 160 is twisted in a predetermined direction, a tension in lace 1966 and so in at least straps 1962 and 1963 may be adjusted. Straps 1963,1664 may be considered distal straps of upper cuff 1920, while straps 1973,1674 may be considered proximal straps of lower cuff 1930.

In some embodiments, central harness 1980 comprises a fabric, leather, or any other suitable material. In some embodiments, central harness 1980 is configured to be disposed immediately adjacent the user's knee when brace 1900 is properly worn by the user.

Rather than utilizing tensioning mechanism 140, having quick-release buckle 141 and its related components 142-149 (as with at least brace 100 in FIG. 1), brace 1900 comprises one or more Fidlock winch mechanisms. For example, brace 1900 comprises at least ratcheting dial 160 disposed on strap 1963. In some embodiments, ratcheting dial 160 is substantially as described in connection with any figure herein.

Ratcheting dial 160 comprises a winching mechanism coupled to lace 1966. In operation, a user may don brace 1900 by aligning upright 110 against a side of his or her leg such that hinge 116 is approximately aligned immediately adjacent the knee. The user may pull straps 1962-1664 and 1972-1674 around a side of the user's leg and attach bracket 1956, adjustably coupling the second end of strap 1962 and the first end of strap 1963, to the anterior portion of upper cuff 1920. Where a similar bracket adjustably couples the second end of strap 1972 and the first end of strap 1973, that bracket may also be coupled to the anterior portion of lower cuff 1930. To achieve a desired amount of tension, the user may twist ratcheting dial 160, which pulls on and increases a tension in lace 1966, which increases a tension in one or more of straps 1962 and 1963 thereby adjusting support provided by and a fit of brace 1900. This functionality may be at least in part a result of how lace 1966 is threaded between bracket 1956 and each of straps 1962, 1963. As illustrated in FIGS. 20 and 21, lace 1966 may extend from ratcheting dial 160, disposed on strap 1963, and pass back and forth between bracket 1956 and strap 1963 and between bracket 1956 and strap 1962.

Ratcheting dial 160 being coupled to lace 1966, which itself is strung back and forth between bracket 1956 and each of straps 1962, 1963 as described above, greatly reduces the complexity of brace 1900 compared to other braces in a novel and inventive way at least in that a tension in each of straps 1962, 1963 may be simultaneously adjusted by twisting ratcheting dial 160.

Figure 22:
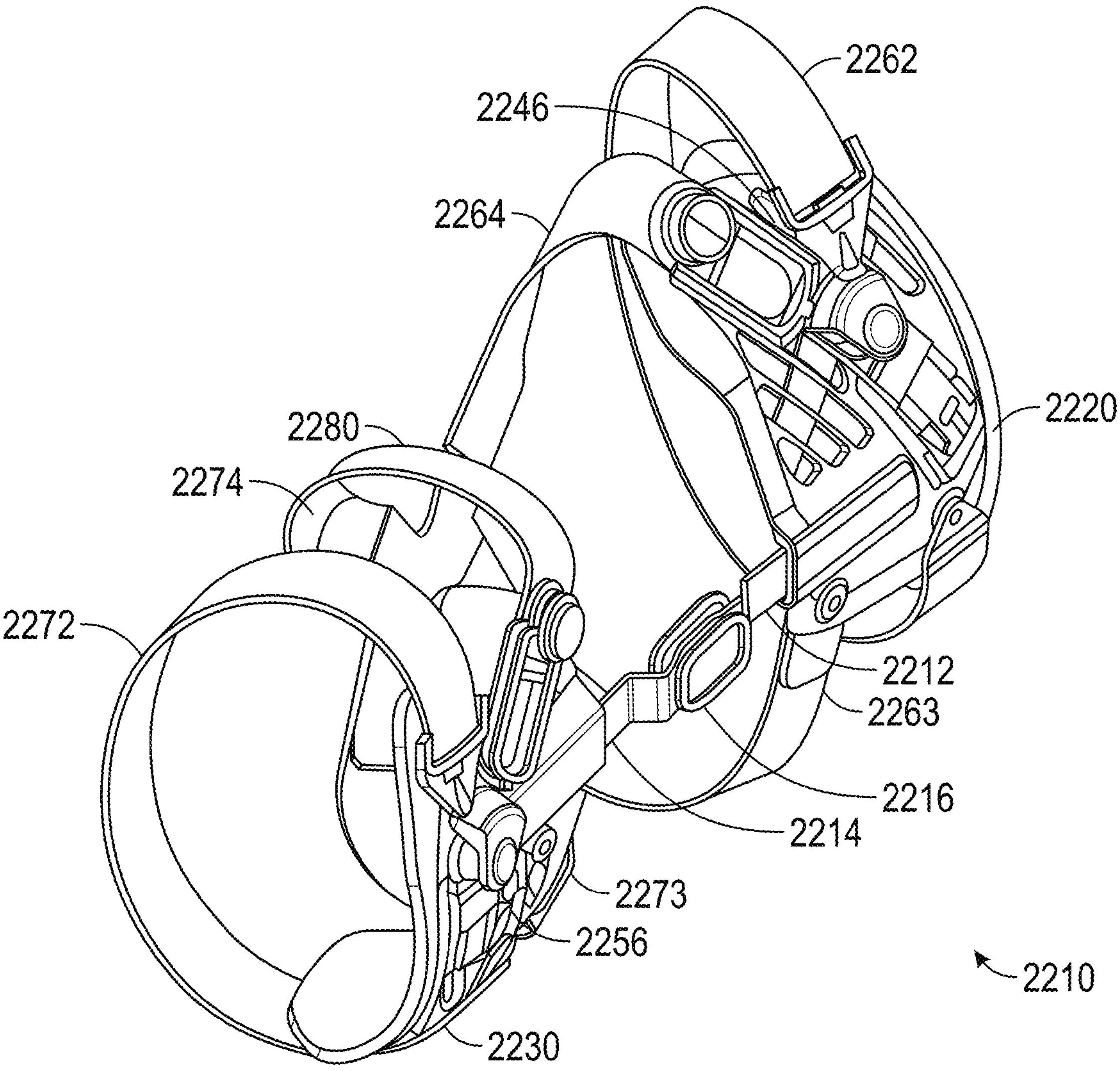
FIG. 22 illustrates a perspective view of yet another brace for use in the treatment of osteoarthritis in a fastened orientation and unattached to a wearer, in accordance with some embodiments.
Figure 23:
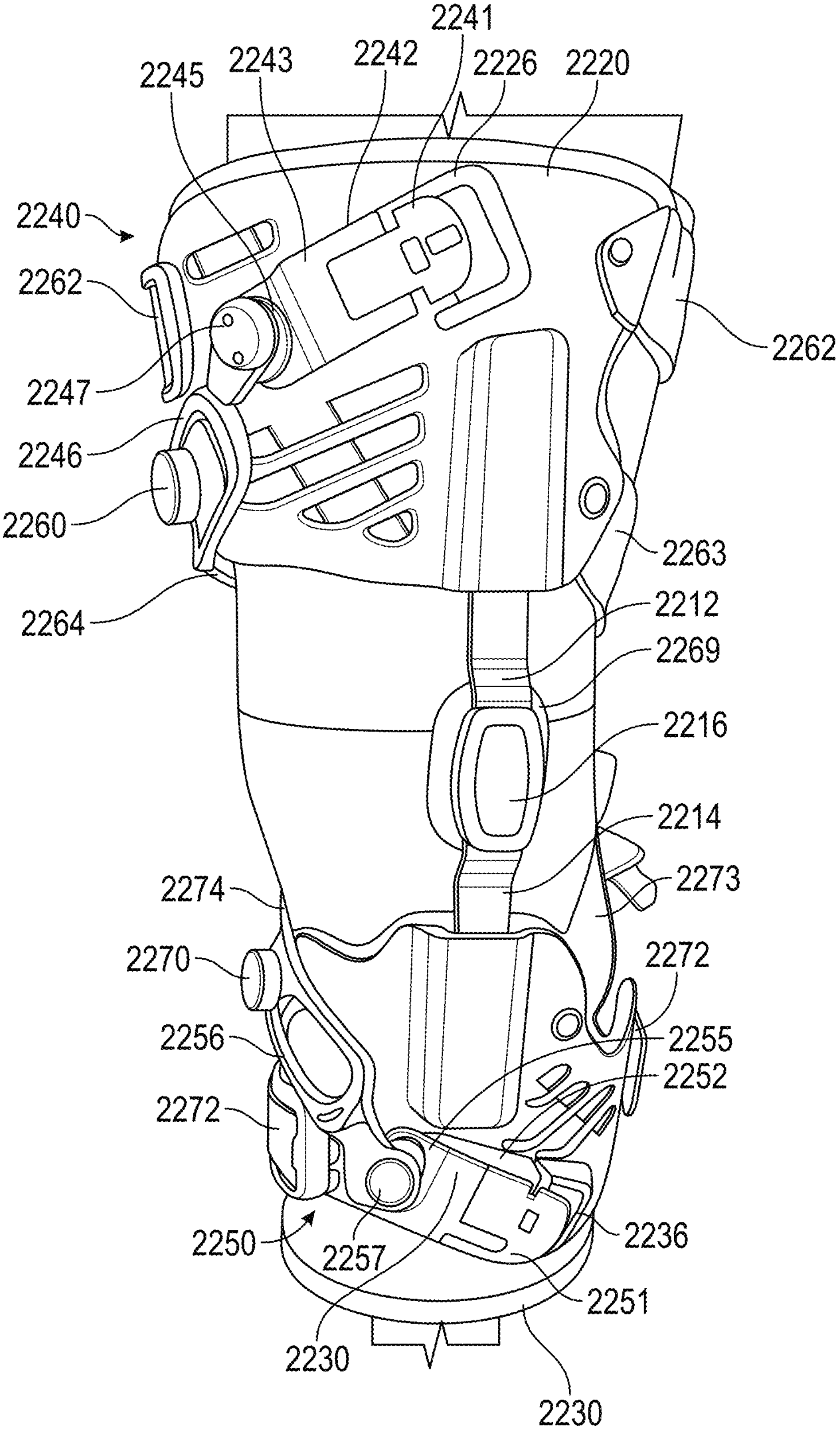
FIG. 23 illustrates a perspective view of the brace of FIG. 22 as attached to a wearer, in accordance with some embodiments.
Figure 24:
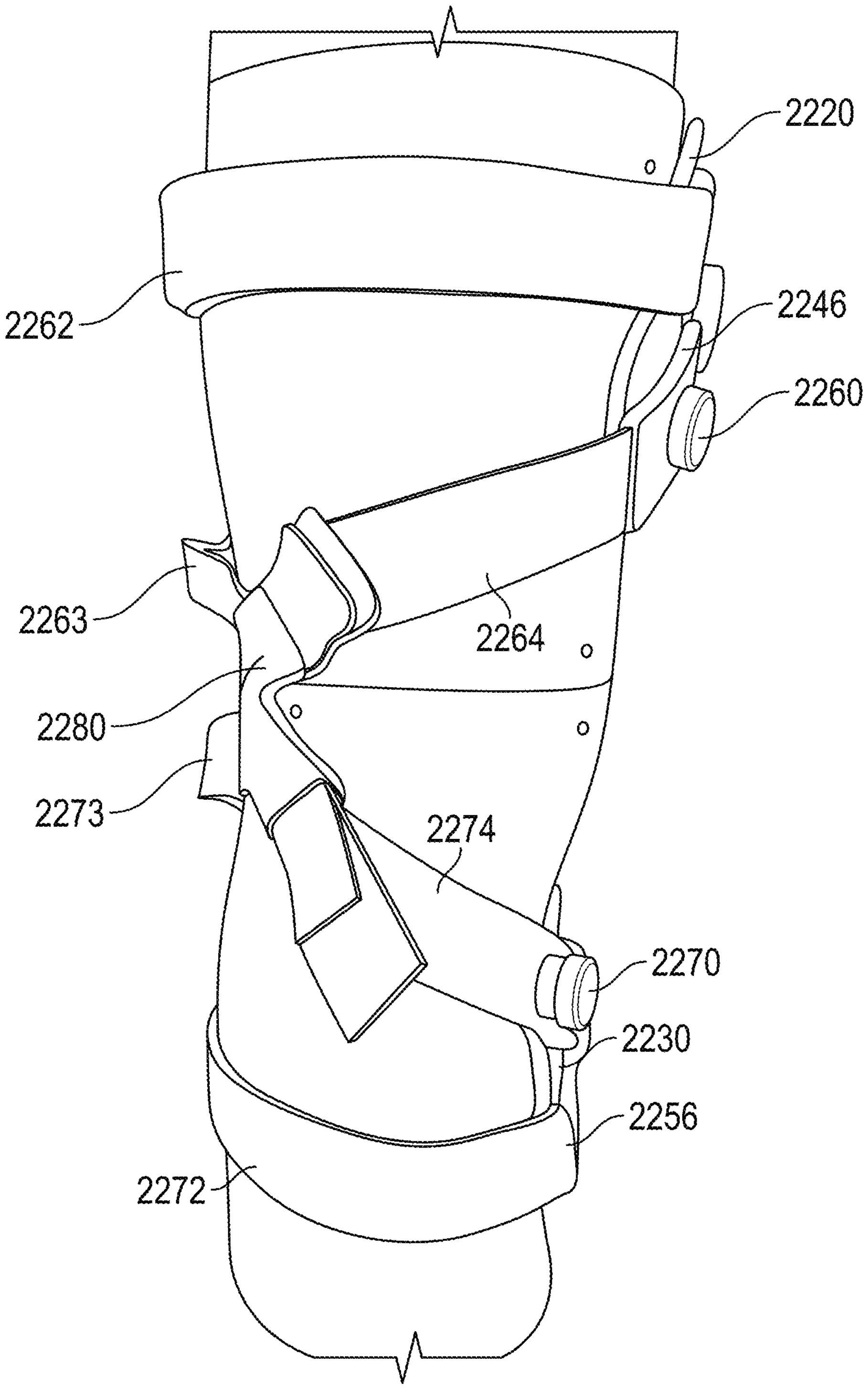
FIG. 24 illustrates a perspective view of the brace of FIG. 22 as attached to a wearer and viewed from an approximately opposite angle compared to FIG. 23, in accordance with some embodiments.

FIG. 22 illustrates a perspective view of yet another brace 2200 for use in the treatment of osteoarthritis in a fastened orientation and unattached to a wearer, in accordance with some embodiments. FIGS. 23 and 24 illustrate opposite perspective views of brace 2200 as attached to a wearer.

As will be described in more detail below, brace 2200 comprises several inventive features including but not limited to incrementally adjustable, telescoping upright supports, straps coupled to a central harness so as to prevent those straps from crossing one another, and magnetic attachments disposed on at least one of the straps and/or on a bracket to which the straps are directly coupled, and on the cuffs or quick-release buckles that are coupled to the cuffs of brace 2200.

Brace 2200 includes upright 2210, comprising upper rigid support 2212, lower rigid support 2214, and hinge 2216, which physically couples upper rigid support 2212 and lower rigid support 2214. In some embodiments, brace 2200 may further comprise a condyle pad 2269 permanently, adjustably and/or removably coupled and/or couplable to a knee-facing side of hinge 2216 and/or a case thereof.

Brace 2200 further comprises an upper cuff 2220 and a lower cuff 2230. Upper and lower cuffs 2220, 2230 may be substantially similar to respective upper and lower cuffs 120, 130. For example, and not limitation, cuff 2220 may comprise a recess 2226 and cuff 2230 may comprise a recess 2236, substantially similar to respective recesses 126, 136 of brace 100, previously described in connection with at least FIG. 1.

Upper cuff 2220 is incrementally and telescopically adjustably coupled to upper rigid support 2212 and lower cuff 2230 is incrementally and telescopically adjustably coupled to lower rigid support 2214, as will be described in more detail in connection with at least FIGS. 25-30 below.

Brace 2200 further comprises straps 2262-2264 and 2272-2274, coupled to a central harness 2280, to a respective bracket 2246, 2256, and/or to a respective one of cuffs 2220, 2230 so as to prevent those straps from crossing one another, while still providing sufficient tension and support to brace 2200 and to its wearer, as will be described in connection with at least FIGS. 24, 31-33, 37-40 and 44 below.

Brace 2200 further comprises tensioning mechanisms 2240, 2250 comprising several independent elements configured to work in concert to provide both gross and fine adjustments to the amount of tension and/or support in brace 2200 and/or provided to its wearer. Such independent elements include but are not limited to a ratcheting dial 2260, 2270 and lace 2266, 2276 system disposed on the straps or on the brackets 2246, 2256 to which the straps are directly coupled, as will be described in more detail in connection with at least FIGS. 33 and 34; and magnetic attachments and corresponding receptacles disposed on the straps 2264, 2274 and/or brackets 2246, 2256 to which those straps are directly coupled, and/or cuffs 2220, 2230 themselves, as will be described in more detail in connection with at least FIGS. 31-44 below.

Figure 25:
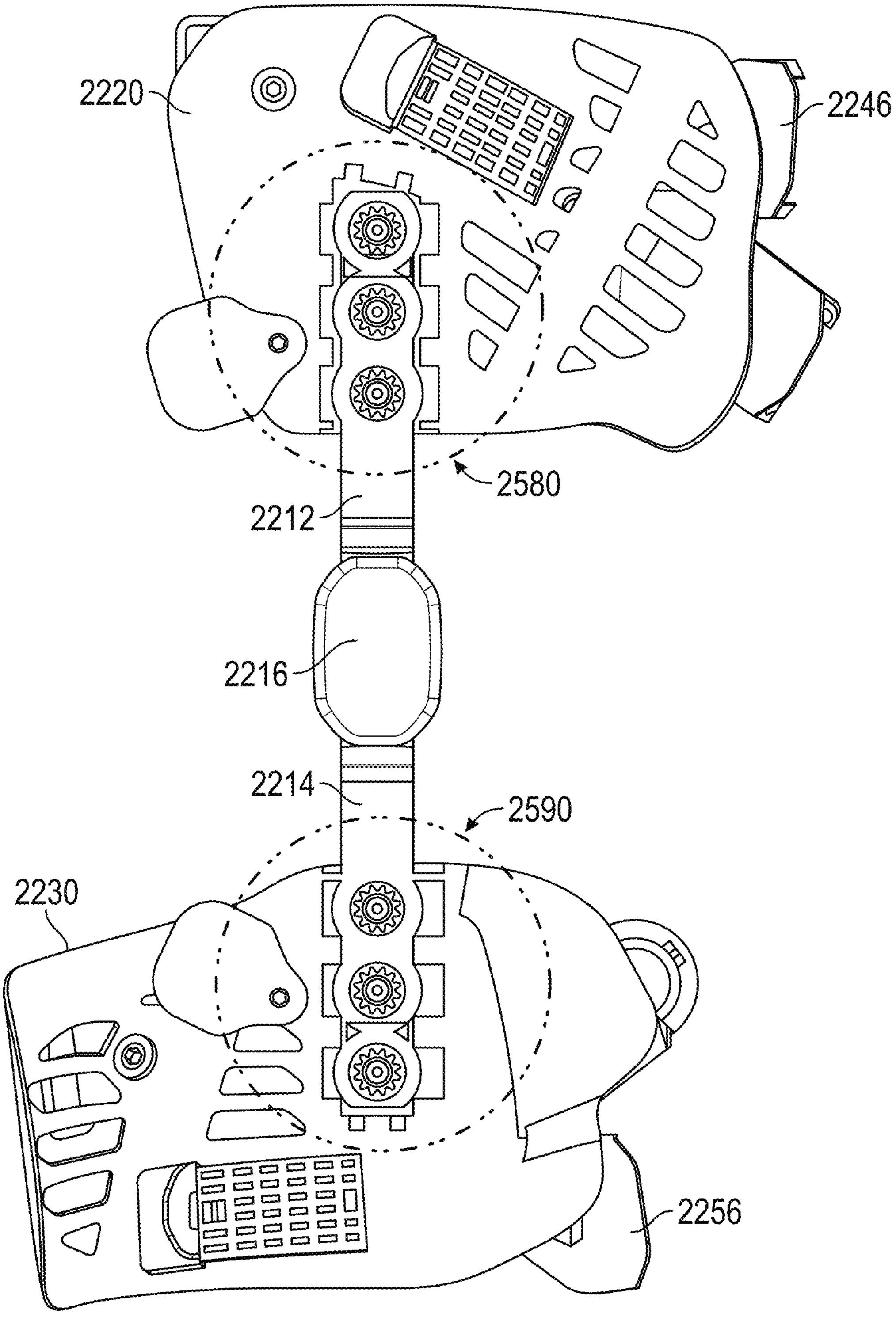
FIG. 25 illustrates a side view of the brace of FIG. 22, however, omitting one or more aspects thereof for clarity, in accordance with some embodiments.

Turning to the incremental and telescopic adjustability of brace 2200, FIG. 25 illustrates a side view of brace 2200 of FIG. 22 while FIGS. 26-30 illustrate various aspects of respective upper and lower telescoping adjustment mechanisms 2580, 2590.

Figure 26:
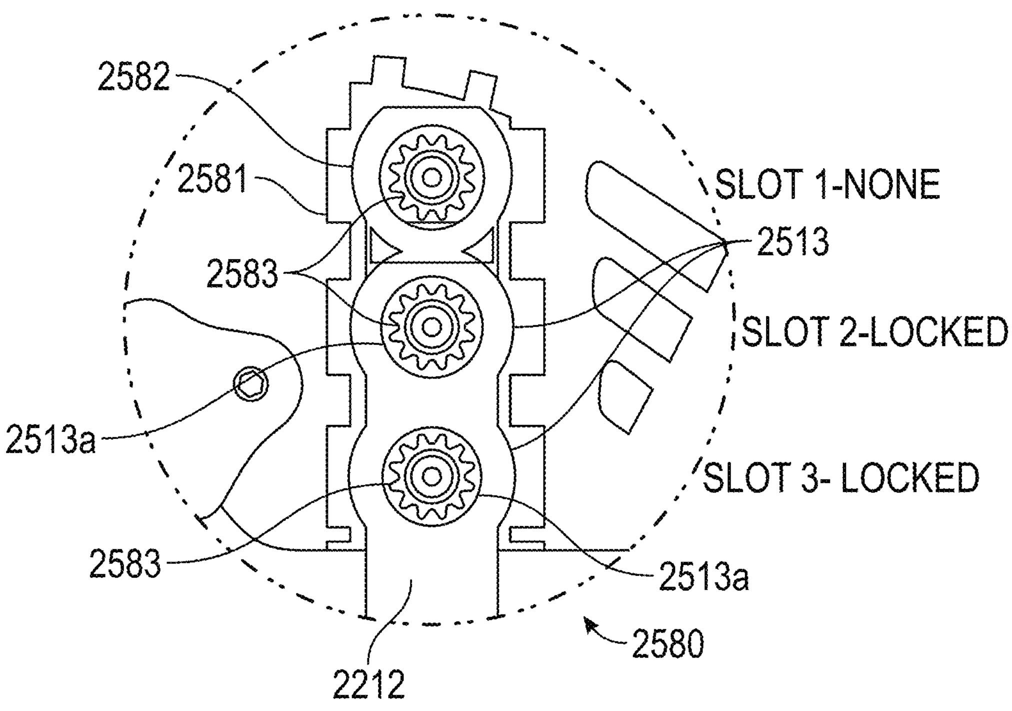
FIG. 26 illustrates a magnified portion B of telescoping upper rigid member and cuff of the brace of FIG. 22, in accordance with some embodiments.

In FIG. 26, upper telescoping adjustment mechanism 2580 is illustrated as including a proximal end of upper rigid upright 2212 and a recess 2582 in upper cuff 2220 having a complementary shape that is configured to receive the proximal end in any of a plurality of different orientations.

For example, proximal end of upper rigid upright 2212 may comprise a plurality of locating features 2513. In some embodiments, locating features 2513 comprise widened portions each having a form factor, or footprint, of a circle having a diameter that is greater than a width of upper rigid upright 2212. Accordingly, extending proximally, a width of the proximal end of upper rigid upright may widen, from the width of upper rigid upright 2212, follow the outline of a circle to a maximum diameter equal to the circle, and then narrow to the width of upper rigid upright 2212 again before successively widening and narrowing again at each successive locating feature 2513. However, the present disclosure is not so limited and locating features 2513 may have any suitable form factor, including a substantially constant width. Each locating feature 2513 further comprises a respective aperture 2513*a* therein.

Recess 2582 may have a form factor, or footprint, of a plurality of incompletely overlapping circles, each having a diameter that is greater than the width of upper rigid upright 2212. However, the present disclosure is not so limited and recess 2582 may have any form factor, or footprint, suitable for receiving at least one of locating features 2513 therein. In some embodiments, recess 2582 further has a minimum width that is slightly greater than the width of upper rigid upright 2212 so as to ensure the proximal end of upper rigid upright 2212 may be disposed and seated therein. Recess 2582 may further comprise a plurality of receptacles 2583, each disposed and centered in a corresponding one of the incompletely overlapping circles. As shown, receptacles 2583 may each have one or more features configured to couple with a locking cap 2585 (see FIGS. 28-30), for example and not limitation one or more ramping features and/or a plurality of teeth extending radially away from a central portion of receptacle 2583. In some embodiments, locking features 2513 may have a substantially circular form factor.

Figure 29:
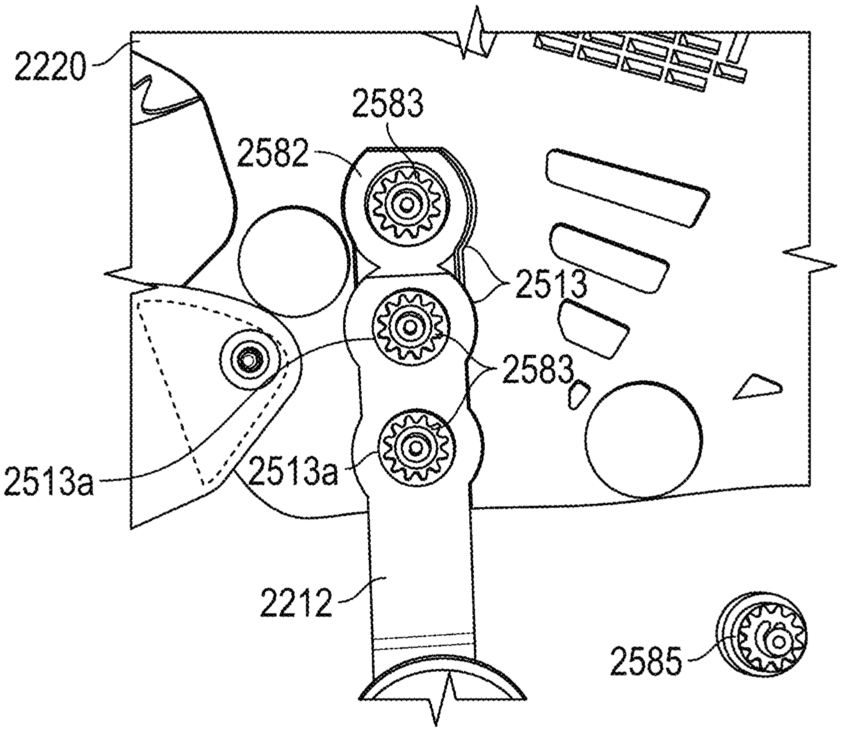
FIG. 29 illustrates a magnified portion of an alternative design for the telescoping upper rigid member and cuff for the brace of FIG. 22, in accordance with some embodiments.

In some embodiments, upper cuff 2220 comprises a slotted insert 2581 configured to interlock with upper cuff 2220, for example at least partially in or with recess 2582. For example, in FIG. 26, insert 2581 is shown to comprise a substantially longitudinal rectangular portion having a width at least as wide as a widest portion of recess 2582 and a plurality of transverse rectangles, each having a width greater than the longitudinal rectangular portion and being substantially centered about a respective one of receptacles 2583 within recess 2582. While the present disclosure is not so limited, slotted insert 2581 may comprise a portion of brace 2200 that is overmolded onto upper cuff 2220. FIG. 29 illustrates upper cuff 2220 without insert 2581.

In operation, a length of the assembled combination of upper cuff 2220 and upper rigid upright 2212 may be adjusted to one of several values, depending on how the locating features 2513 of the proximal end of upper rigid upright 2212 are seated and secured within recess 2582. For example, one orientation is illustrated in FIG. 26, where the two most proximal locating features 2513 of the proximal end of upper rigid upright 2212 are respectively disposed in the two most distal circular portions of recess 2582, such that the two most distal receptacles 2583 are aligned with the two most proximal apertures 2513*a* of the proximal end of upper rigid upright 2212. However, other orientations may also be achieved by alternatively disposing one or more of the locating features 2513 of the proximal end of upper rigid upright 2212 in different portions of recess 2582.

Figure 28:
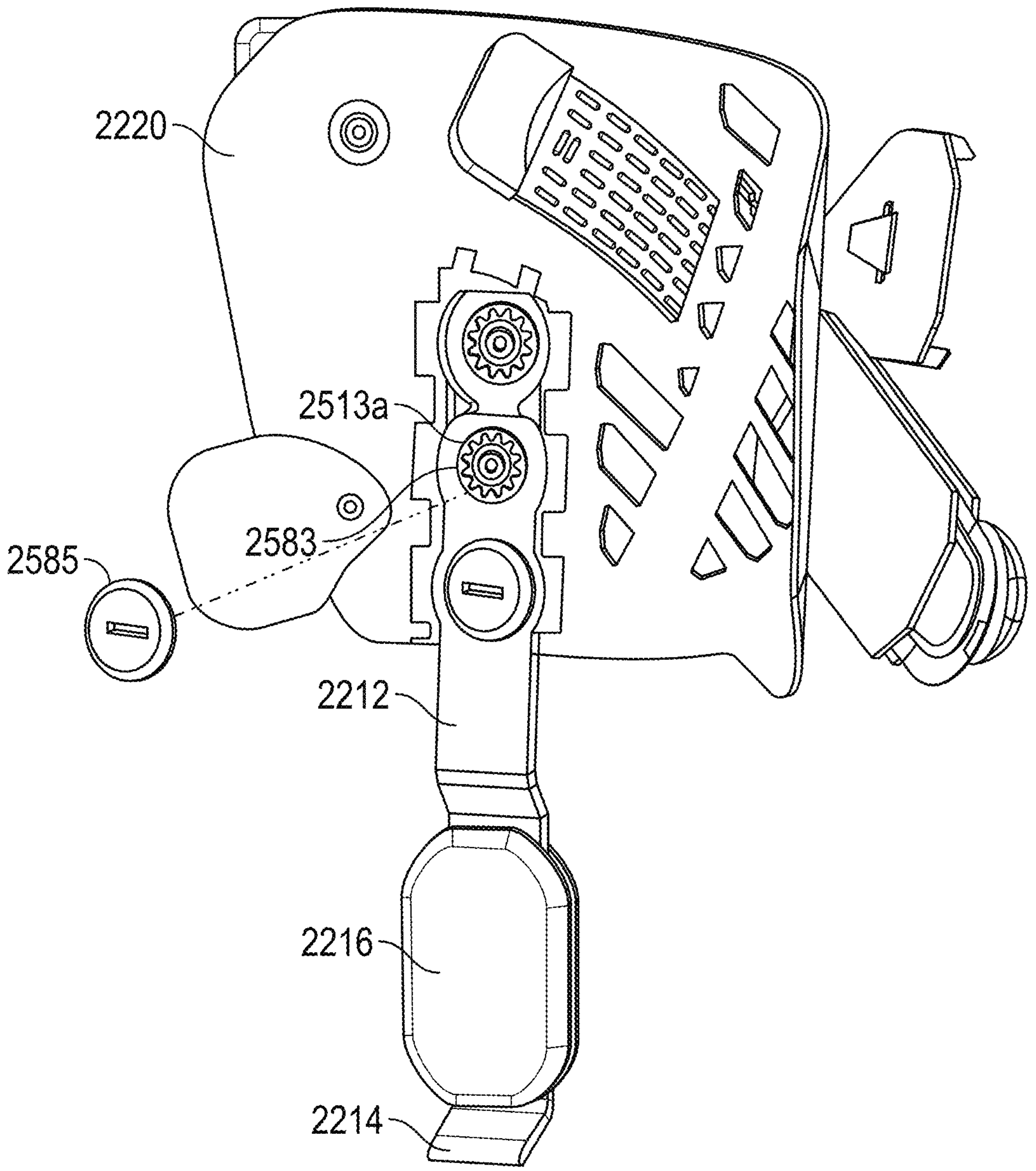
FIG. 28 illustrates a perspective view of the telescoping upper rigid member and cuff of the brace of FIG. 22 and a locking cap thereof, in accordance with some embodiments.
Figure 30:
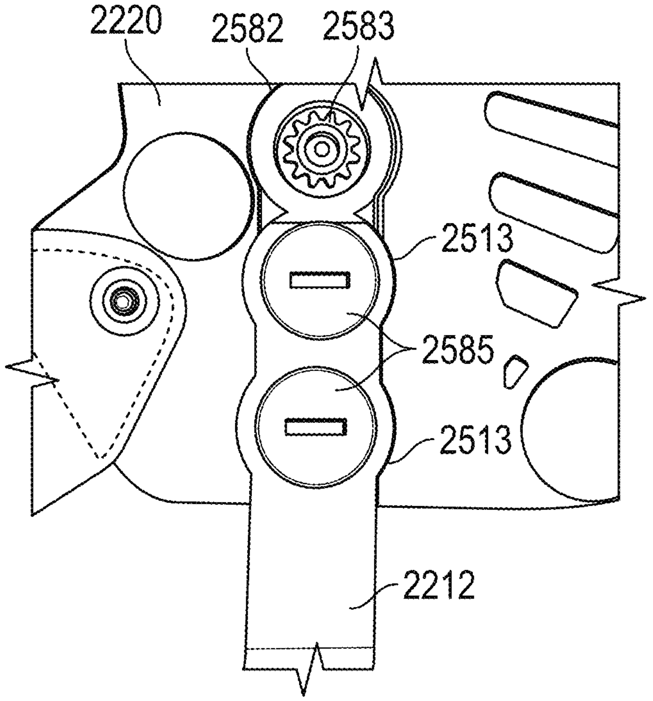
FIG. 30 illustrates a magnified portion of an alternative design for the telescoping lower rigid member and cuff of the brace of FIG. 22, in accordance with some embodiments.
Figure 31:
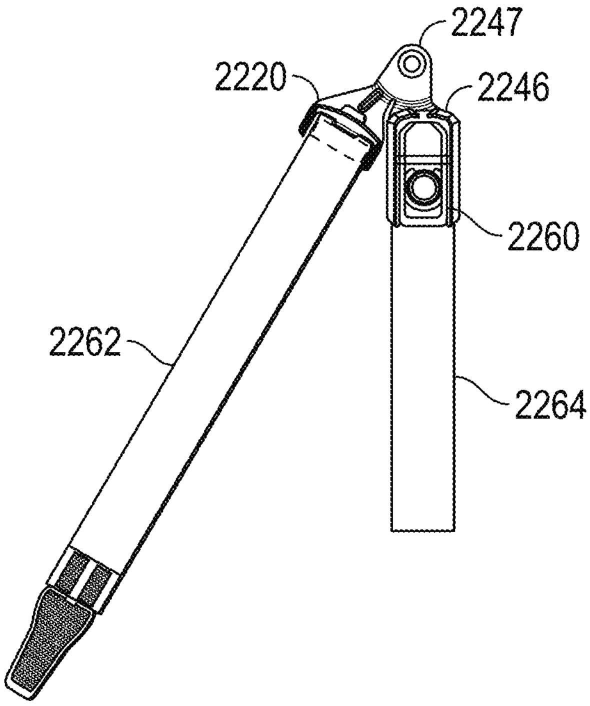
FIG. 31 illustrates an upper straps and bracket portion of the brace of FIG. 22, in accordance with some embodiments.
Figure 32:
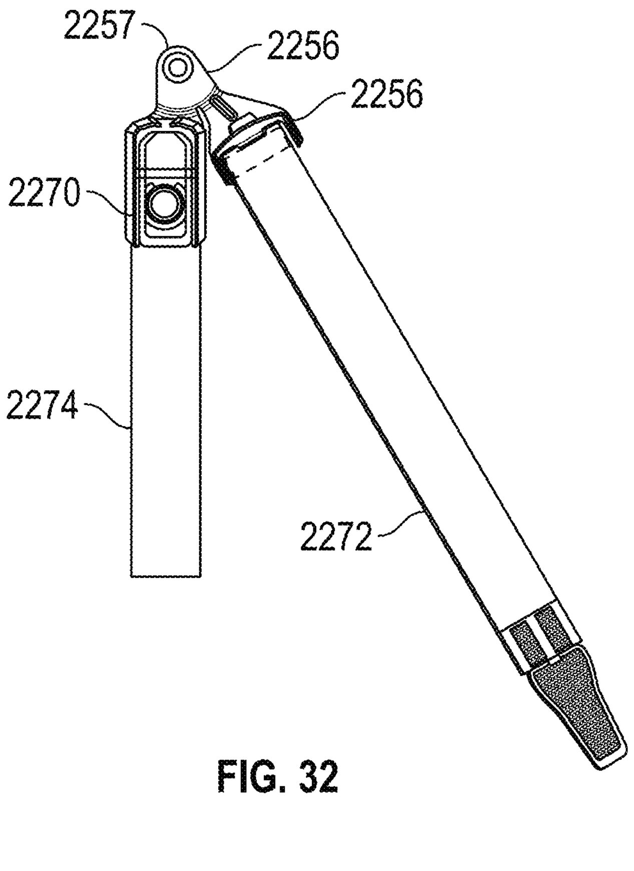
FIG. 32 illustrates a lower straps and bracket portion of the brace of FIG. 22, in accordance with some embodiments.

Once the desired assembled combination of upper cuff 2220 and upper rigid upright 2212 is achieved, locking caps 2585 may be disposed over upper rigid upright 2212, into apertures 2513*a* and locked with mating features of receptacles 2582. For example, in some embodiments, a top surface of locking cap 2585 comprises a "flat-head" or other depression allowing installation and locking utilizing a screwdriver or similar tool. For example, in some embodiments, locking cap 2585 may "click" or snap twice upon being inserted as described above and may be locked by rotating locking cap 2585 through a quarter-turn. Such fixation may be accomplished through any known method, including but not limited to, complementary threads, ramp features, and/or clasps on locking cap 2585 and/or receptacles 2583. FIGS. 28 and 30 illustrate locking caps 2585 in such example locked positions.

Figure 27:
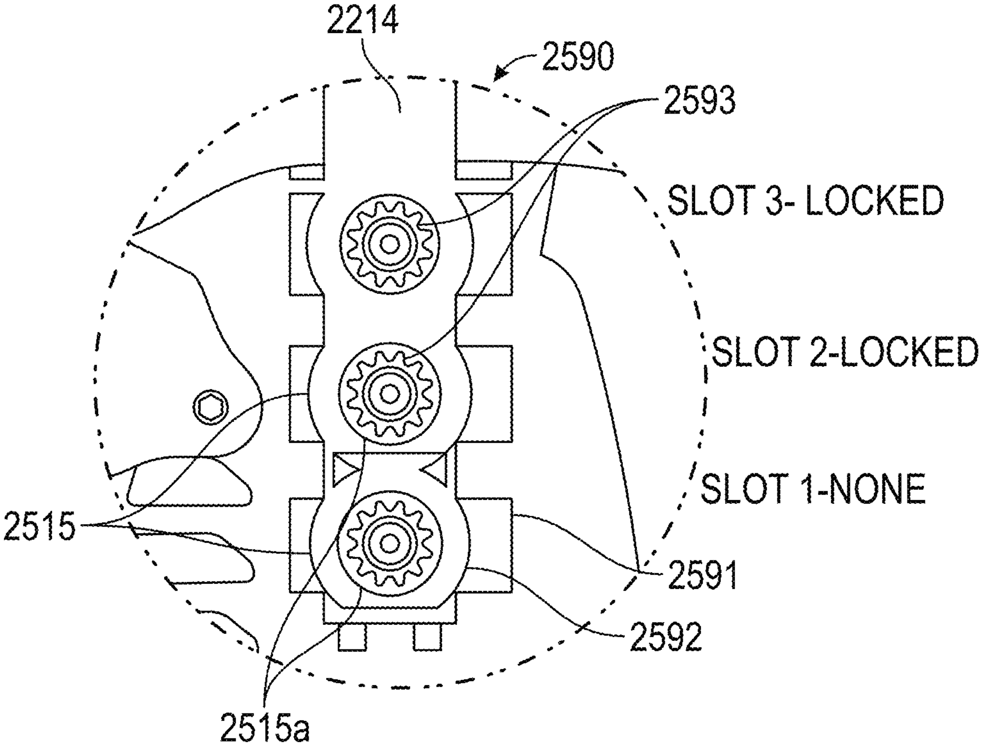
FIG. 27 illustrates a magnified portion C of telescoping lower rigid member and cuff of the brace of FIG. 22, in accordance with some embodiments.

In FIG. 27, lower telescoping adjustment mechanism 2590 is illustrated as including a distal end of lower rigid upright 2214 and a recess 2592 having a complementary shape that is configured to receive the distal end in any of a plurality of different orientations.

For example, distal end of lower rigid upright 2214 may comprise a plurality of locating features 2515. In some embodiments, locating features 2515 comprise widened portions each having a form factor, or footprint, of a circle having a diameter that is greater than a width of lower rigid upright 2214. Accordingly, extending distally, a width of the distal end of lower rigid upright 2230 may widen, from the width of lower rigid upright 2214, follow the outline of a circle to a maximum diameter equal to the circle, and then narrow to the width of lower rigid upright 2214 again before successively widening and narrowing again at each successive locating features 2515. However, the present disclosure is not so limited and locating features 2515 may each have a suitable form factor, including a substantially constant width. Each locating feature 2515 further comprises a respective aperture 2515*a* therein.

Recess 2592 may have a form factor, for footprint, of a plurality of incompletely overlapping circles, each having a diameter that is greater than the width of lower rigid upright 2214. However, the present disclosure is not so limited and recess 2592 may have any form factor, or footprint, suitable for receiving at least one of locating features 2515 therein. In some embodiments, recess 2592 further has a minimum width that is slightly greater than the width of lower rigid upright 2214 so as to ensure the distal end of lower rigid upright 2214 may be disposed and seated therein. Recess 2592 may further comprise a plurality of receptacles 2593, each disposed and centered in a corresponding one of the incompletely overlapping circles. As shown, receptacles 2593 may each have one or more features configured to couple with a locking cap 2585 (see FIGS. 28-30), for example and not limitation one or more ramping features and/or a plurality of teeth extending radially away from a central portion of receptacle 2593.

In some embodiments, lower cuff 2230 comprises a slotted insert 2591 configured to interlock with upper cuff 2220, for example at least partially in or with recess 2592. For example, in FIG. 27, insert 2591 is shown to comprise a substantially longitudinal rectangular portion having a width at least as wide as a widest portion of insert 2592 and a plurality of transverse rectangles, each having a width greater than the longitudinal rectangular portion and being substantially centered about a respective one of receptacles 2593 within recess 2592. While the present disclosure is not so limited, slotted recess 2591 may comprise a portion of brace 2200 that is overmolded onto lower cuff 2230. FIG. 30 illustrates lower cuff 2230 without recess 2591 of such an overmolded portion.

In operation, a length of the assembled combination of lower cuff 2230 and lower rigid upright 2214 may be adjusted to one of several values, depending on how the locating features 2515 of the distal end of lower rigid upright 2214 are seated and secured within recess 2592. For example, one orientation is illustrated in FIG. 27, where the two most distal locating features 2515 of the distal end of lower rigid upright 2214 are respectively disposed in the two most proximal circular portions of recess 2592, such that the two most proximal receptacles 2593 are aligned with the two most distal apertures **2515*a* of the distal end of lower rigid upright 2214. However, other orientations may also be achieved by alternatively disposing one or more of the locating features 2515 of the distal end of lower rigid upright 2214 in different portions of recess 2592**.

Once the desired assembled combination of lower cuff 2230 and lower rigid upright 2214 is achieved, locking caps 2585 may be disposed over lower rigid upright 2214, into apertures **2515*a* and locked with mating features of receptacles 2593 as previously described in connection with mechanism 2580**.

Figure 37:
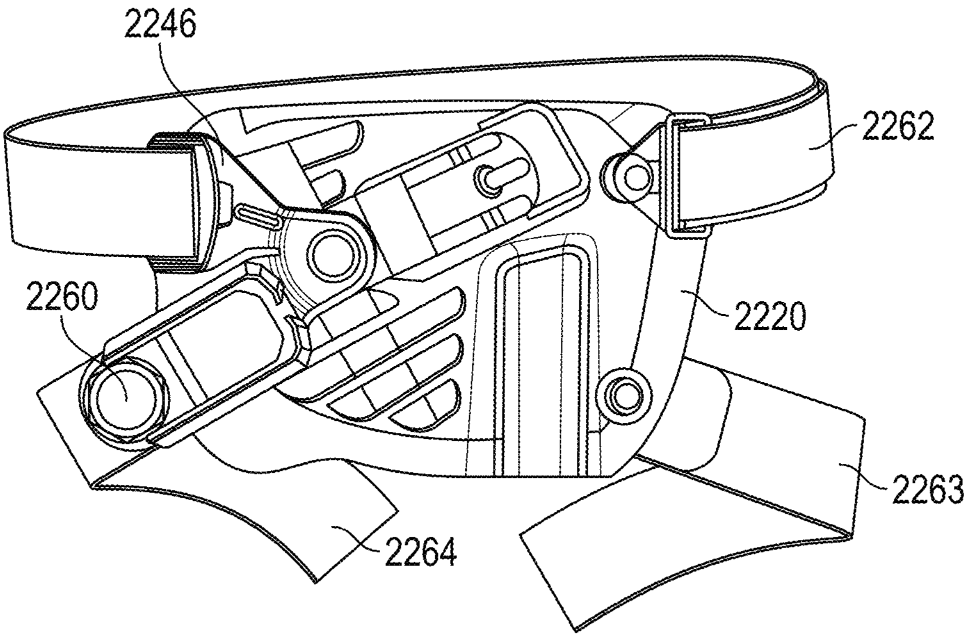
FIG. 37 illustrates a side view of the upper cuff, straps and bracket of the brace of FIG. 22 in a fastened orientation, in accordance with some embodiments.
Figure 38:
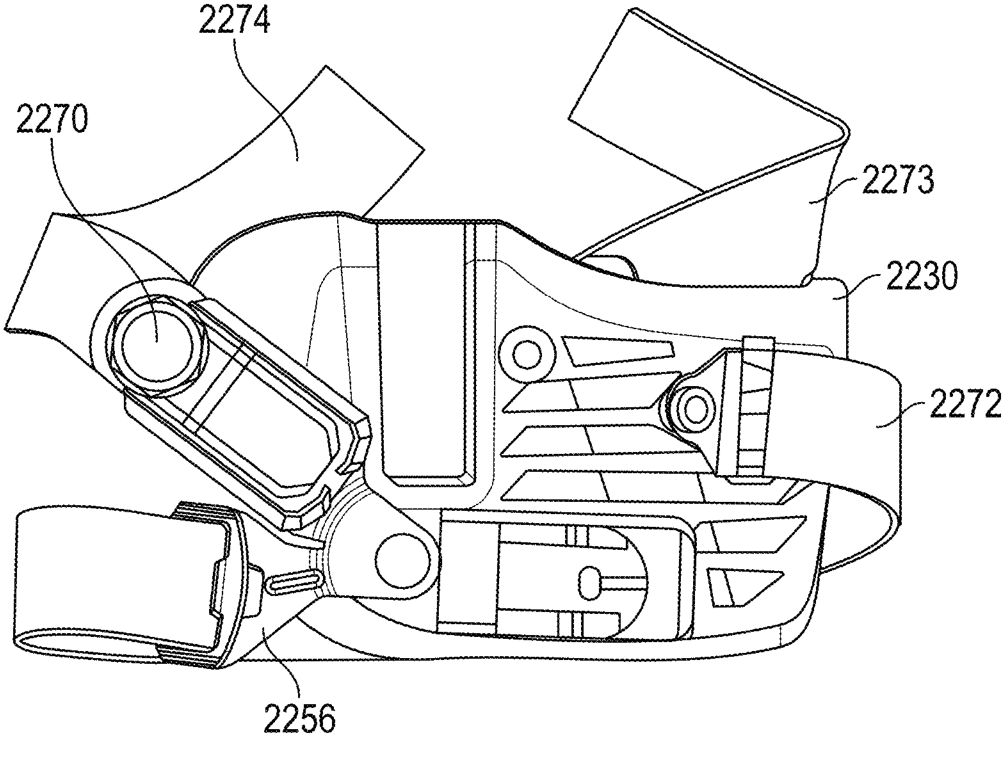
FIG. 38 illustrates a side view of the lower cuff, straps and bracket of the brace of FIG. 22 in a fastened orientation, in accordance with some embodiments.
Figure 39:
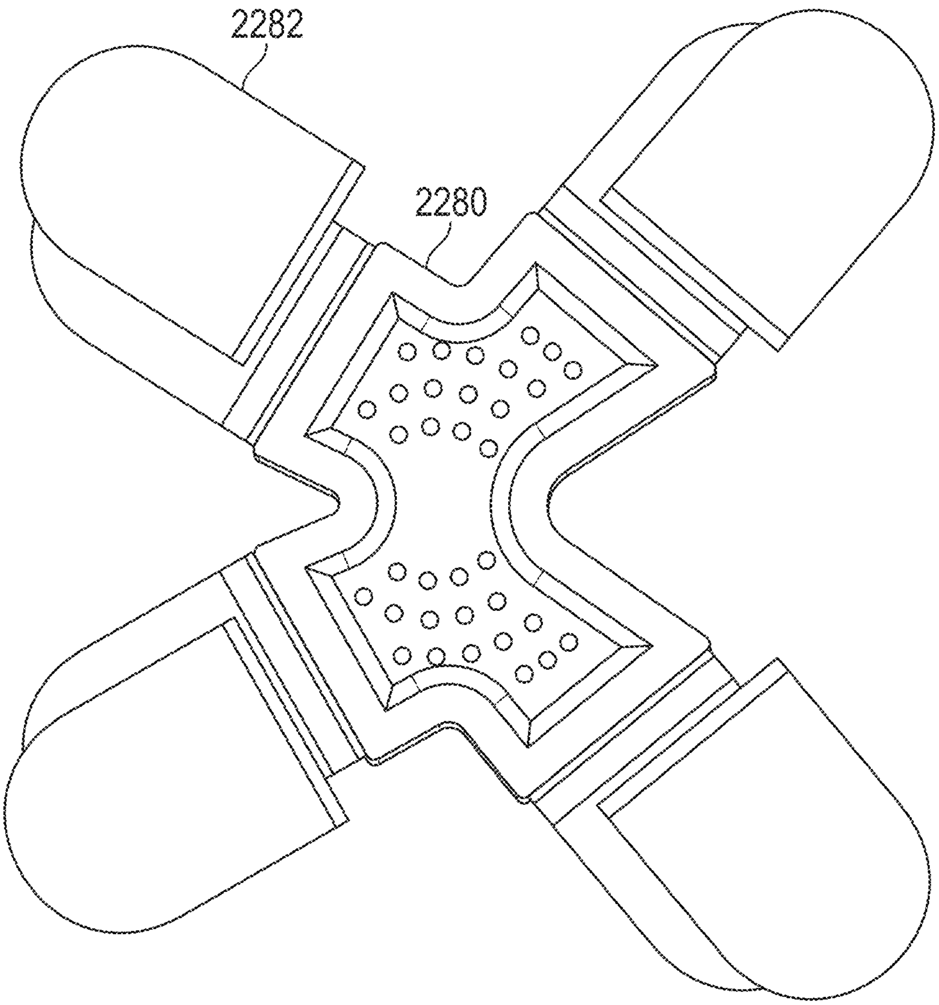
FIG. 39 illustrates a central harness for coupling non-overlapping and non-crossing straps of the brace of FIG. 22, in accordance with some embodiments.
Figure 40:
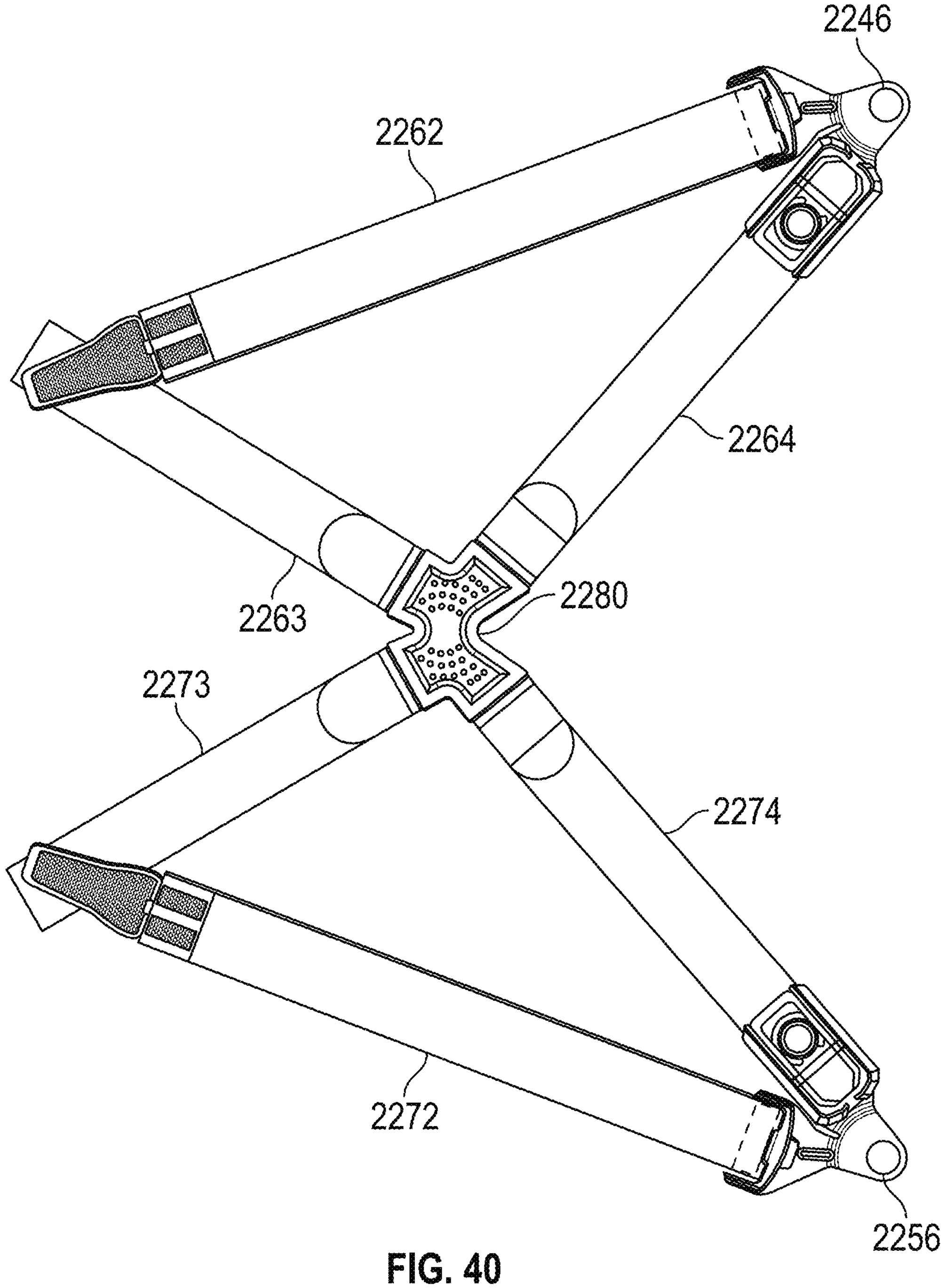
FIG. 40 illustrates the central harness of FIG. 39 coupled with non-overlapping and non-crossing straps of the brace of FIG. 22, in accordance with some embodiments

Turning to the non-crossing straps aspect of brace 2200 and at least FIGS. 24, 31-33, 37-40 and 44, brace 2200 comprises upper bracket 2246, lower bracket 2256 and central harness 2280. Central harness 2280 is shown in FIGS. 39 and 40. In some embodiments, central harness 2280 comprises a fabric, leather, or any other suitable material. In some embodiments, central harness 2280 comprises a plurality of slits, each configured to receive and adjustably and/or permanently anchor an end of a corresponding one of straps 2263, 2264, 2273, 2274. Alternatively, central harness 2280 may comprise a plurality of alligator clip-type flaps 2282 that secure straps 2263, 2264, 2273, 2274 to central harness 2280. For example, one end of each of straps 2263, 2264, 2273, 2274 may be coupled to central harness 2280 utilizing hook and loop fasteners. As a specific example, at least one end of each of at least straps 2263, 2264, 2273, 2274 may comprise one of a hook and loop fastener, while alligator clip-type flaps 2282 may each comprise the other of the hook and loop fastener such that, when properly secured, a portion of each strap is folded between and hook and loop fastened to opposing inside surfaces of a respective alligator clip-type flap 2282. In more detail, when properly secured, a first end of each such strap may be hook and loop fastened against and extend from a distal tip of a first inside surface of the respective alligator clip-type flap 2282, toward where the first inside surface of the respective alligator clip-type flap 2282 meets the opposite second inside surface of the respective alligator clip-type flap 2282, folded over itself at approximately this meeting point, and then toward a distal tip of the second inside surface of the respective alligator clip-type flap 2282. In this way, a hook and loop contact surface substantially twice the footprint of the alligator clip-type flap 2282 may be obtained with each strap fastened to central harness 2280. In some embodiments, central harness 2280 and/or alligator clip-type flaps 2282 may comprise nylon and/or a substantially elastic material. In some embodiments, central harness 2280 and/or alligator clip-type flaps 2282 are die cut. Central harness 2280 is configured to be disposed immediately adjacent the user's knee, e.g., directly against the user's skin and/or clothing, when brace 2200 is properly worn by the user.

Upper and lower brackets 2246, 2256 may each comprise or be referred to as "y-brackets" at least in part because brackets 2246, 2256 have a substantial "y-shape" in that each comprises a first portion extending in a first direction and configured to couple a strap, a second portion extending in a second direction that diverges from the first direction and configured to couple another strap, while a third portion of each bracket extends in a third direction different from the first or second directions and is configured to couple the bracket to respective cuff 2220 or 2230.

Each of straps 2262, 2263, 2264 are attached between a different two of upper bracket 2246, central harness 2280 and upper cuff 2220. And upper bracket 2246 is configured to releasably and magnetically attach to upper cuff 2220. For example, a first end of strap 2262 is coupled to bracket 2246 and a second end of strap 2262 is coupled to upper cuff 2220. Accordingly, strap 2262 is configured to extend substantially horizontally between its first and second ends around an upper leg of a wearer when brace 2200 is worn. A first end of strap 2263 is coupled to a posterior portion of upper cuff 2220 and a second end of strap 2263 is coupled to central harness 2280. Accordingly, strap 2263 is configured to extend diagonally between its first and second ends when brace 2200 is worn. A first end of strap 2264 is coupled directly to bracket 2246 and/or indirectly to bracket 2246 via a lace 2266 (see FIG. 33) and a second end of strap 2264 is coupled to central harness 2280. Accordingly, strap 2264 is configured to extend diagonally between its first and second ends when brace 2200 is worn (see, e.g., FIG. 40).

Each of straps 2272, 2273, 2274 are attached between a different two of lower bracket 2256, central harness 2280 and lower cuff 2230. And lower bracket 2256 is configured to releasably and magnetically attach to lower cuff 2230. For example, a first end of strap 2272 is coupled to bracket 2256 and a second end of strap 2272 is coupled to lower cuff 2230. Accordingly, strap 2272 is configured to extend substantially horizontally between its first and second ends around a lower leg of a wearer when brace 2200 is worn. A first end of strap 2273 is coupled to a posterior portion of lower cuff 2230 and a second end of strap 2273 is coupled to central harness 2280. Accordingly, strap 2273 is configured to extend diagonally between its first and second ends when brace 2200 is worn. A first end of strap 2274 is coupled directly to bracket 2256 and/or indirectly to bracket 2256 via a lace (similar to lace 2266 of FIG. 33) and a second end of strap 2274 is coupled to central harness 2280. Accordingly, strap 2274 is configured to extend diagonally between its first and second ends when brace 2200 is worn (see, e.g., FIG. 40). Such a configuration, especially utilizing central harness 2280, none of straps 2262-2264 or 2272-2274 overlap or cross one another, while still providing sufficient tension and support to brace 2200 and to its wearer.

Figure 33:
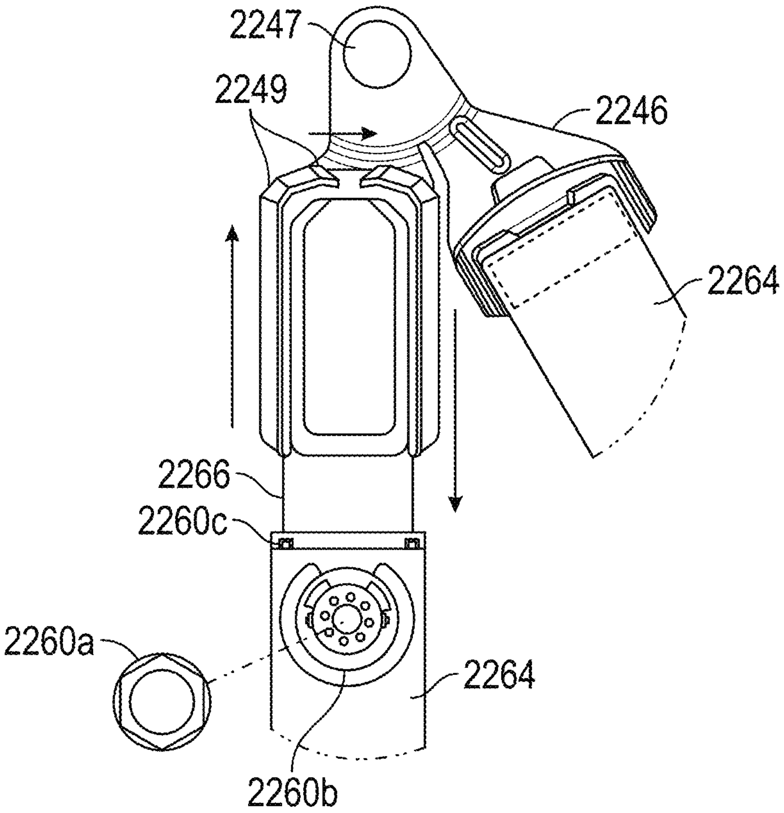
FIG. 33 illustrates a magnified view of a tensioning mechanism of the brace of FIG. 22, in accordance with some embodiments.
Figure 34:
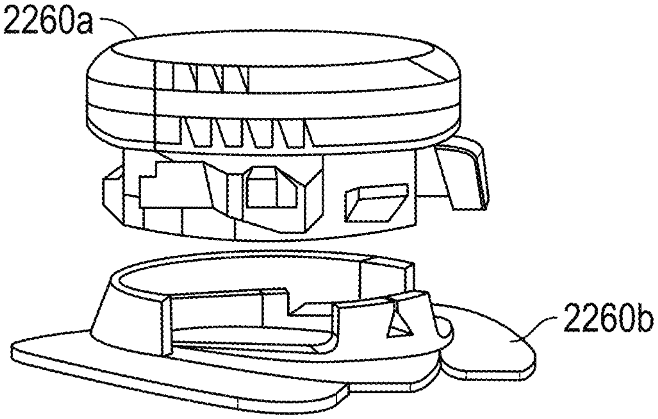
FIG. 34 illustrates a perspective view of a portion of the tensioning mechanism of FIG. 33, in accordance with some embodiments.
Figure 35:
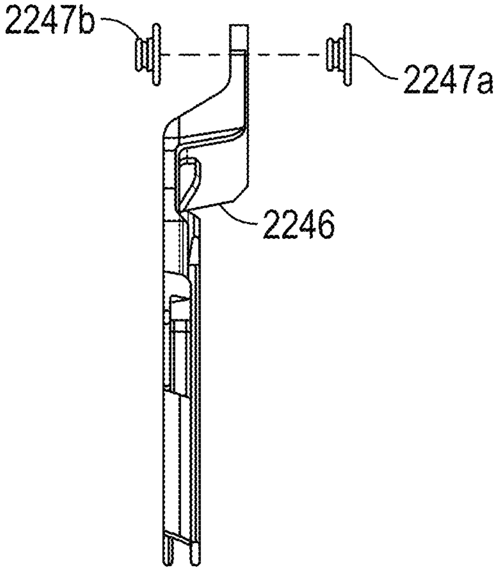
FIG. 35 illustrates a side view of the brackets of FIGS. 31 and 32, in accordance with some embodiments.
Figure 36:
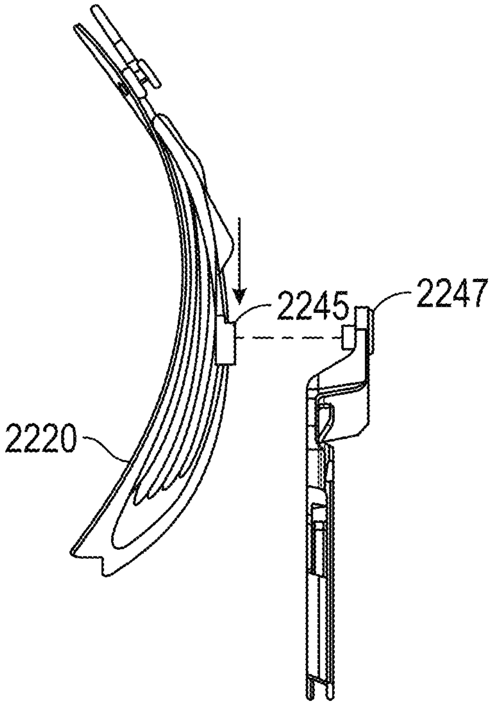
FIG. 36 illustrates a side view of the brackets of FIGS. 31 and 32 being releasably magnetically coupled a respective cuff of the brace of FIG. 22, in accordance with some embodiments.

Discussion now turns to brackets 2246, 2256 and to the reel-and-lace systems that provide micro-adjustment of tension in at least one strap coupled thereto. For example, as previously described, and as shown in FIG. 33, bracket 2246 comprises a first portion extending in a first direction and configured to couple to strap 2262, a second portion extending in a second direction that diverges from the first direction and configured to couple, directly or indirectly, to strap 2264, and a third portion that extends in a third direction different from the first and second directions and comprises a first portion 2247 of a magnetic coupler configured to magnetically couple bracket 2246, directly or indirectly, to upper cuff 2220. FIG. 35 illustrates first portion 2247 of the magnetic coupler, configured to be magnetically coupled to a second portion 2245 of the magnetic coupler (disposed directly or indirectly on upper cuff 2220). First portion 2247 is illustrated as comprising a magnetic or ferromagnetic post assembly, for example, comprising post 2247*b* and a fixing component (e.g., screw) 2247*a* configured to extend through the third portion of bracket 2246 and fix to (e.g., thread into) a backside of post 2247*b*. Post 2247*b* may be magnetic or sufficiently ferromagnetic to be held by a magnetic receptacle (see, e.g., receptacle and/or clasp 2245 in FIG. 36). In some embodiments, receptacle 2245 comprises a slot configured to magnetically and/or slidingly hold post 2247*b* therein. In such embodiments, receptacle 2245 may also be magnetic, or at least sufficiently ferromagnetic to pivotally hold magnetic post 2247*b* therein. As illustrated in at least FIG. 35, magnetic or ferromagnetic post 2247*b* may have a first diameter and a distal tip of magnetic or ferromagnetic post 2247*b* may have a second diameter greater than the first diameter, thereby preventing magnetic or ferromagnetic post 2247*b* from pulling out of the slot of magnetic or ferromagnetic receptacle 2245 in any direction other than a direction in which magnetic or ferromagnetic post 2247*b* is slidingly received into the slot of magnetic or ferromagnetic receptacle 2245. Such a direction a direction in which magnetic or ferromagnetic post 2247*b* is slidingly received into the slot of magnetic or ferromagnetic receptacle 2245 is shown by the vertically oriented arrow in FIG. 36. FIG. 37 illustrates the upper portion of brace 2200 when bracket 2246 is so magnetically secured. The present disclosure also contemplates an opposite arrangement, where post 2247*b* is disposed directly or indirectly on upper cuff 2220 and receptacle 2245 is disposed on the third portion of bracket 2246.

Turning back to FIG. 33, the reel-and-lace system may comprise a base 2260*b* disposed directly on strap 2264 and a dial 2260*a* configured to rotate with respect to base 2260*b*. Turning dial 2260*a* is configured to wind or unwind portions of a lace 2266 from a reel within base 2260*b*. Lace 2266 is coupled to such a reel, fed through one of guides 2260*c* on strap 2264, to and through one and then the other of eyelets 2249 on the second portion of bracket 2246, back to and through the other of guides 2260*c* on strap 2264, and coupled to reel. Accordingly, as dial 2260*a* is turned, and lace 2266 is wound onto or unwound from the reel, a separation between guides 2260*c* and eyelets 2249, and so between portions of strap 2264 and bracket 2246, is adjusted and a tension in at least strap 2264 can be micro-adjusted, either before or after first 2247 and second 2245 portions of the magnetic coupler are magnetically coupled to one another.

Bracket 2256 has a substantially identical construction and function to bracket 2246, having the same first, second and third portions and a first portion 2257 of a magnetic coupler for coupling to lower cuff 2230, bracket 2256, however, coupling straps 2272 and 2274. Bracket 2256 also uses a similar reel-and-lace system utilizing a dial 2270 and functioning substantially identically, except adjusting spacing between strap 2274 and bracket 2256 and, so, micro-adjusting a tension in at least strap 2274. FIG. 38 illustrates the lower portion of brace 2200 when bracket 2256 is so magnetically secured.

Discussion now turns to tensioning mechanisms 2240 and 2250, which each comprise several independent elements configured to work in concert to provide both gross and fine adjustments to the amount of tension and/or support in brace 2200 and/or provided to its wearer. A set of elements of tensioning mechanisms 2240 and 2250, responsible for micro-adjusting tensions in brace 2200, include brackets 2246, 2256 and the respective reel-and-lace systems comprising dials 2260, 2270 disposed on straps 2264, 2274, as previously described. Another set of elements of tensioning mechanisms 2240, 2250, responsible for easy coupling of brackets 2246, 2256, directly or indirectly, to their respective cuffs 2220, 2230 are the first and second portions of the magnetic couplers (e.g., 2245 and 2247 in FIG. 36), as previously described.

Figure 41:
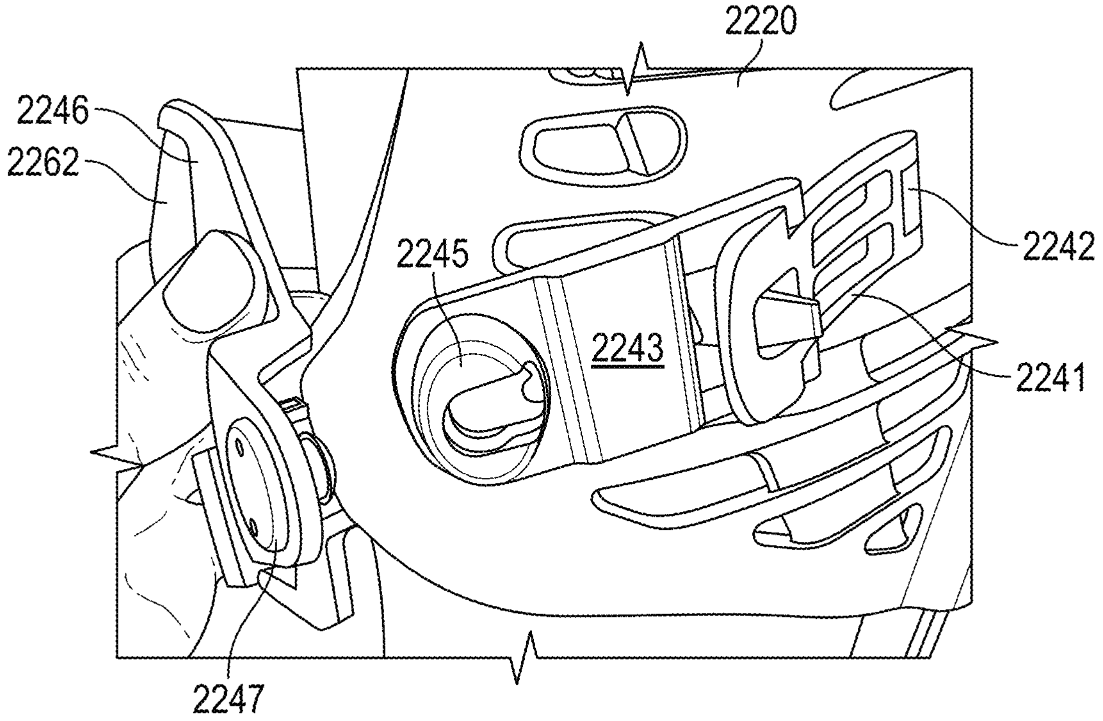
FIG. 41 illustrates a perspective view of magnetically fastening an upper bracket to an upper tensioning mechanism on the upper cuff of the brace of FIG. 22, in accordance with some embodiments.
Figure 42:
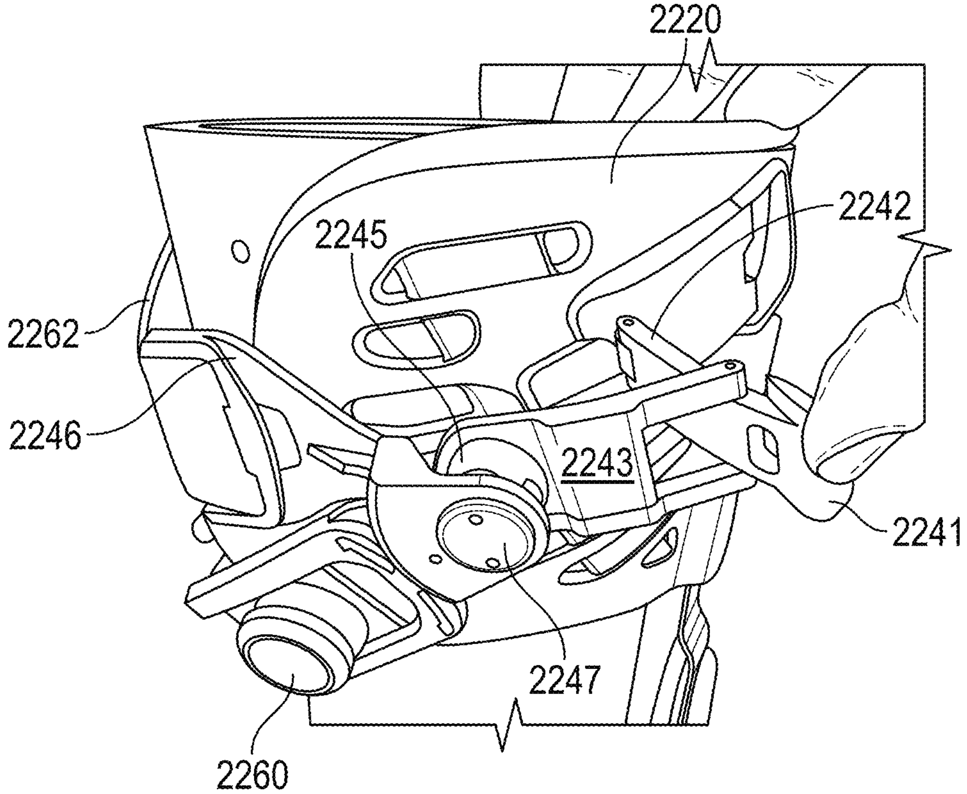
FIG. 42 illustrates a perspective view of tightening the upper tensioning mechanism on the upper cuff of the brace of FIG. 22, in accordance with some embodiments.

Another set of elements of tensioning mechanisms 2240 and 2250, responsible for gross adjustments to the amount of tension and/or support in brace 2200, are respective quick-release buckles disposed on upper 2220 and lower 2230 cuffs, for example as shown in FIGS. 23, 41 and 42. Specifically, tensioning mechanism 2240 comprises a quick-release buckle 2241 having a first end pivotally coupled to an anchor point 2242. In some embodiments, anchor point 2242 may be integrally formed as a part of upper cuff 2220. In other embodiments, anchor point 2242 may be a separate component from upper cuff 2220 that is permanently coupled to upper cuff 2220.

Quick-release buckle 2241 is configured to be disposed in a locked orientation in which a second end of quick-release buckle 2241 opposite the first end is disposed maximally to one direction, shown as within recess 2226 of upper cuff 2220 in FIG. 23. Quick-release buckle 2241 is also configured to be disposed in unlocked orientations where the second end of quick-release buckle 2241 has been lifted away from cuff 2220 and/or recess 2226 and quick-release buckle 2241 has been or is being pivoted, about anchor point 2242, away from the locked orientation.

A first end of a quick-release extension 2243 is pivotally coupled to quick-release buckle 2241 at a position between the first and second ends of quick-release buckle 2241. A second end 2245 of quick-release extension 2243, opposite the first end, is releasably coupled to bracket 2246 via second portion 2245 of the magnetic coupler, as previously described.

Likewise, tensioning mechanism 2250 comprises a quick-release buckle 2251 having a first end pivotally coupled to an anchor point 2252. In some embodiments, anchor point 2252 may be integrally formed as a part of upper cuff 2220. In other embodiments, anchor point 2252 may be a separate component from upper cuff 2220 that is permanently coupled to upper cuff 2220.

Quick-release buckle 2251 is configured to be disposed in a locked orientation in which a second end of quick-release buckle 2251 opposite the first end is disposed maximally to one direction, shown as within recess 2226 of upper cuff 2220 in FIG. 23. Quick-release buckle 2251 is also configured to be disposed in unlocked orientations where the second end of quick-release buckle 2251 has been lifted away from cuff 2230 and/or recess 2236 and quick-release buckle 2251 has been or is being pivoted, about anchor point 2252, away from the locked orientation.

A first end of a quick-release extension 2253 is pivotally coupled to quick-release buckle 2251 at a position between the first and second ends of quick-release buckle 2251. A second end 2255 of quick-release extension 2253, opposite the first end, is releasably coupled to bracket 2256 via second portion 2255 of the magnetic coupler, as previously described.

A first end of strap 2263 may be coupled to upper cuff 2220 utilizing any suitable method, for example hook-and-loop fasteners, snaps, buttons, or the like coupled to and/or through a slit, a d-ring, or any other suitable fastening means of upper cuff 2220.

Figure 43:
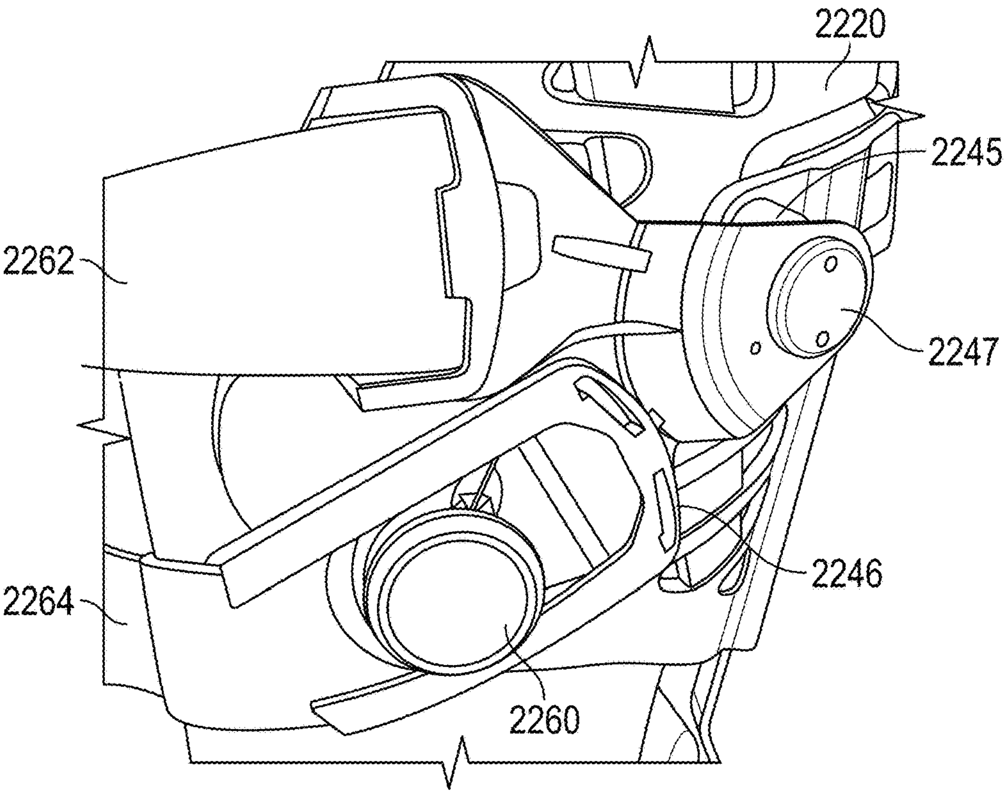
FIG. 43 illustrates a perspective view of an upper portion of the brace of FIG. 22 in a fixed and tightened orientation, in accordance with some embodiments.
Figure 44:
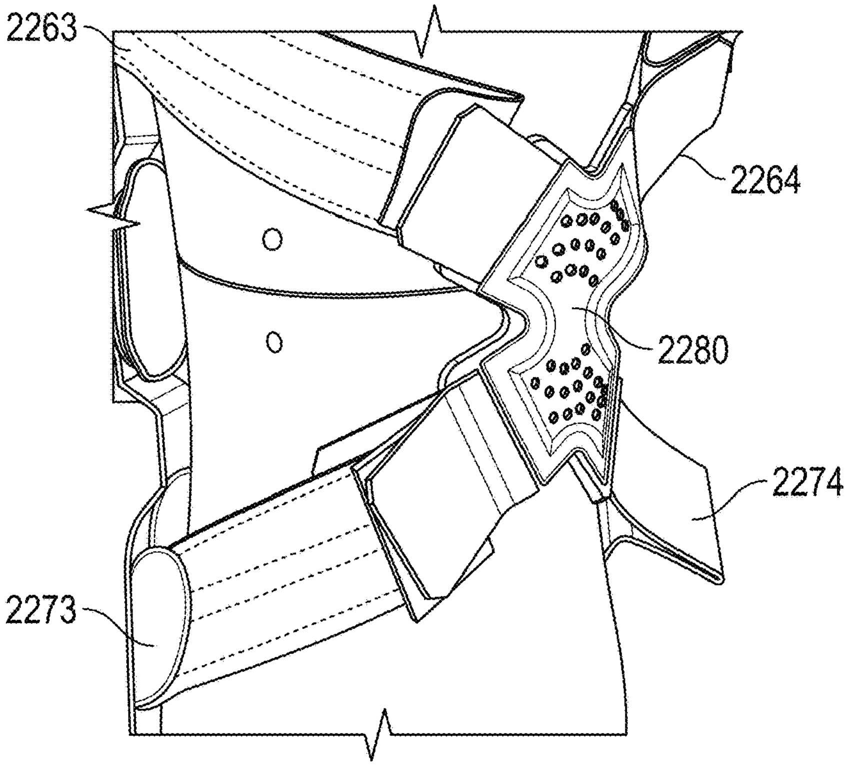
FIG. 44 illustrates a perspective view of an upper portion of the brace of FIG. 22 as viewed from an approximately opposite angle compared to FIG. 42, in accordance with some embodiments.

In operation, a user may don brace 2200 by aligning upright 2210 against a side of his or her leg such that hinge 2216 is approximately aligned immediately adjacent the knee. The user may grasp bracket 2246 and pull it, straps 2262-2264, and central harness 2280 around a side of the user's leg and attach first portion 2247 of magnetic coupler to second portion of magnetic coupler 2245, which is itself coupled to quick release extension 2243. When first portion 2247 is brought sufficiently near to second portion 2245, they will automatically align and snap together by virtue of the alignment between their mutual magnetic and/or ferromagnetic portions. Then, quick release buckle 2241 may be pivoted from an unlocked position to the locked position, achieving a first, gross adjustment to the tension in the straps 2262-2264. To micro-adjust a desired amount of tension in the straps, the user may twist dial 2260, which pulls on and increases a tension in lace 2266, which increases a tension in one or more of straps 2262-2264, thereby adjusting support provided by and a fit of upper cuff 2220. FIG. 43 illustrates such a condition for upper cuff 2220, while FIG. 44 shows a position of central harness 2280 when upper cuff 2220 is in the condition shown in FIG. 43.

The user may also grasp bracket 2256 and pull it, straps 2272-2274, and central harness 2280 around a side of the user's leg and attach first portion 2257 of magnetic coupler to second portion of magnetic coupler 2255, which is itself coupled to quick release extension 2253. When first portion 2257 is brought sufficiently near to second portion 2255, they will automatically align and snap together by virtue of the alignment between their mutual magnetic and/or ferromagnetic portions. Then, quick release buckle 2251 may be pivoted from an unlocked position to the locked position, achieving a first, gross adjustment to the tension in the straps 2272-2274. To micro-adjust a desired amount of tension in the straps, the user may twist dial 2270, which pulls on and increases a tension in its lace, which increases a tension in one or more of straps 2272-2274, thereby adjusting support provided by and a fit of lower cuff 2230.

Figure 45:
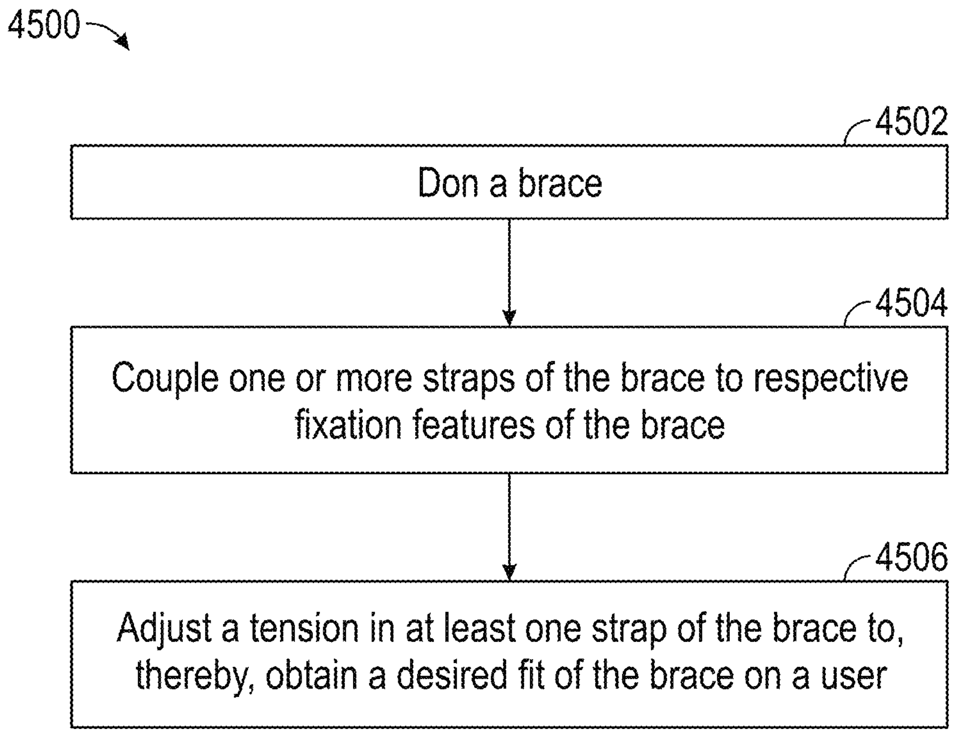
FIG. 45 illustrates a flowchart of a method of utilizing a brace in the treatment of osteoarthritis, in accordance with some embodiments.

Discussion now turns to one or more methods of using any brace described in this disclosure. FIG. 45 illustrates a flowchart 4500 of a method of utilizing a brace configured for attachment to a joint of a subject, in accordance with some embodiments. Flowchart 4500 may apply to the utilization of any brace described in this disclosure.

Block 4502 includes donning the brace. For example, a user or practitioner may place any brace as described herein on a user's leg.

Block 4504 includes coupling one or more straps of the brace to respective fixation features of the brace. For example, a user or practitioner may couple one or more strap(s) and/or a bracket coupled to such strap(s) of any the brace as described herein to respective elements of the brace that are configured for fixing and/or adjustably fixing at least a portion of the strap(s) to the brace.

Block 4506 includes adjusting a tension in at least one strap of the brace to, thereby, obtain a desired fit of the brace on a user. For example, a user or practitioner may adjust one or more gross and/or fine adjustment features of the brace as described anywhere herein to, thereby, obtain a desired fit of the brace on the user.

Although the present disclosure has been described in terms of certain preferred features, other features of the disclosure including variations in dimensions, configuration and materials will be apparent to those of skill in the art in view of the disclosure herein. In addition, all features detailed in connection with any embodiment herein can be readily adapted for use in any other embodiment herein. The use of different terms or reference numerals for similar features in different embodiments does not imply differences other than those which may be expressly set forth. Accordingly, the present disclosure is intended to be described solely by reference to the appended claims, and not limited to the preferred embodiments disclosed herein.

What is claimed is:

1. A brace configured for attachment to a joint of a subject, the brace comprising:
- a single upright assembly comprising:
  - an upper rigid support;
  - a lower rigid support;
  - a hinge coupling the upper rigid support to the lower rigid support;
  - an upper cuff coupled to the upper rigid support; and
  - a lower cuff coupled to the lower rigid support;
- a plurality of upper straps configured for coupling to the upper cuff such that the plurality of upper straps do not cross when the brace is properly attached to the subject;
- a plurality of lower straps configured for coupling to the lower cuff such that the plurality of lower straps do not cross when the brace is properly attached to the subject; and
- a tensioning mechanism configured to adjust a tension in at least one of the plurality of upper and lower straps,
- wherein at least one of the upper rigid support and the lower rigid support comprises a telescoping adjustment mechanism, comprising:
  - an end of the upper rigid support or of the lower rigid support, comprising:
    - a plurality of widened portions, and
    - a plurality of apertures, each disposed in a respective one of the widened portions;
  - a recess disposed in the upper cuff or in the lower cuff configured to receive at least a subset of the plurality of widened portions in any of a plurality of incrementally overlapped orientations, thereby disposing the upper cuff or the lower cuff in a corresponding one of a plurality of telescopically adjustable configurations with respect to the upper rigid support or the lower rigid support; and
- a plurality of locking features, each configured to be inserted into one of the plurality of apertures and, thereby, secure the cuff in the corresponding telescopically adjustable configuration with respect to the rigid support.

2. The brace of claim 1, wherein:
- the plurality of upper straps comprises an upper stability strap, a first upper force strap and a second upper force strap; and
- the plurality of lower straps comprises a lower stability strap, a first lower force strap and a second lower force strap.

3. The brace of claim 2, wherein the tensioning mechanism comprises:
- a first y-bracket coupled to a second end of the upper stability strap and to a second end of the first upper force strap; and
- a second y-bracket coupled to a second end of the lower stability strap and to a second end of the first lower force strap.

4. The brace of claim 3, wherein the tensioning mechanism comprises:

a quick-release buckle having a first end pivotally coupled to an anchor point on one of the upper cuff and the lower cuff, and a second end positionable in each of a locked orientation and at least one unlocked orientation;

an extension having a first end pivotally coupled to the quick-release buckle at a position between the first and second ends of the quick-release buckle, wherein:

the locked orientation corresponds to the second end of the quick- release buckle pivoted maximally to one direction and the extension shifted maximally to the one direction, and the at least one unlocked orientation corresponds to the second end of the quick-release buckle pivoted away from the locked orientation and the extension shifted less than maximally to the one direction.

5. The brace of claim 4, wherein the tensioning mechanism comprises:

a first magnetic portion of a magnetic coupler fixed to a second end of the extension; and a second portion of the magnetic coupler fixed to one of the first y-bracket or the second y-bracket and configured to cause automatic magnetic alignment between the second portion and the first portion when brought in sufficiently close physical proximity to one another.

6. The brace of claim 5, wherein the tensioning mechanism further comprises:

a ratcheting dial coupled to the first upper or lower force strap; and a lace wound around the ratcheting dial and threaded between the first upper or lower force strap and a corresponding one of the first y-bracket or the second y-bracket, wherein the ratcheting dial, the lace, the first portion of the magnetic coupler and the second portion of the magnetic coupler form a winching mechanism whereby twisting the first ratcheting dial adjusts respective tensions in the lace and in at least the first upper or lower force strap when the brace is worn by the subject.

7. The brace of claim 2, comprising a central harness configured to directly couple to a first end of each of the first upper force strap and the second upper force strap and a first end of each of the first lower force strap and the second lower force strap.

8. The brace of claim 2, wherein a second end of the second upper force strap is directly coupled to the upper cuff, and a second end of the second lower force strap is directly coupled to the lower cuff.

9. The brace of claim 1, wherein the plurality of widened portions of the end of the upper rigid support or of the lower rigid support each have a form factor of a circle having a diameter that is greater than a width of the upper rigid support or of the lower rigid support.

10. The brace of claim 1, wherein the recess disposed in the upper cuff or in the lower cuff has a form factor of a plurality of incompletely overlapping circles.

11. The brace of claim 1, wherein the recess disposed in the upper cuff or in the lower cuff comprises a plurality of receptacles, each receptacle configured to receive and couple with a respective one of the locking featurescaps through one of the apertures of the upper or lower rigid support and to couple with a respective one of the locking features.

12. The brace of claim 1, wherein no portion of the upper cuff or of the lower cuff extends over the hinge.

13. A brace configured for attachment to a joint of a subject, the brace comprising:

a single upright assembly comprising a plurality of rigid supports and a plurality of cuffs, each coupled to one of the plurality of rigid supports;

a plurality of straps, each fixedly coupled, directly or indirectly, to at least one of the cuffs, the plurality of straps comprising a stability strap and a force strap;

a y-bracket coupled to the stability strap and coupled to the force strap, a magnetic coupler configured to magnetically couple the stability strap and the force strap to one of the cuffs, the magnetic coupler comprising:

a magnetic or ferromagnetic post assembly disposed on the y-bracket, the post assembly comprising:

a magnetic or ferromagnetic post, and a fixing component configured to extend through a portion of the y-bracket and fix to the post; and a magnetic or ferromagnetic receptacle disposed on the one of the plurality of cuffs.

14. The brace of claim 13, wherein the stability strap is fixedly coupled to the y-bracket and the force strap is adjustably coupled to the y-bracket.

15. The brace of claim 13, wherein the magnetic or ferromagnetic receptacle comprises a slot configured to slidingly receive and magnetically hold the magnetic or ferromagnetic post therein.

16. The brace of claim 15, wherein the magnetic or ferromagnetic post has a first diameter and a distal tip of the magnetic or ferromagnetic post has a second diameter greater than the first diameter, thereby preventing the magnetic or ferromagnetic post from pulling out of the slot of the magnetic or ferromagnetic receptacle in any direction other than a direction in which the magnetic or ferromagnetic post is slidingly received into the slot of the magnetic or ferromagnetic receptacle.

17. A brace configured for attachment to a joint of a subject, the brace comprising:

a telescopically adjustable upright assembly comprising:

a rigid support having an end comprising:

a plurality of locating features configured to interact with a cuff of the brace, and a plurality of apertures, each disposed in a respective one of the locating features;

the cuff comprising:

a recess configured to receive at least a subset of the plurality of locating features of the rigid support in any of a plurality of incrementally overlapped orientations, thereby disposing the cuff in a corresponding one of a plurality of telescopically adjustable configurations with respect to the rigid support; and a plurality of locking featurescaps, each configured to be inserted into one of the plurality of apertures and, thereby, secure the cuff in the corresponding telescopically adjustable configuration.

18. The brace of claim 17, wherein each of the plurality of locating features comprises a widened portion having a form factor of a circle having a diameter that is greater than a width of the rigid support.

19. The brace of claim 17, wherein the recess in the cuff comprises a plurality of receptacles, each receptacle configured to receive and couple with a respective one of the locking features through one of the apertures of the rigid support.

20. The brace of claim 17, wherein each locking feature comprises a slot configured to receive a screwdriver for turning the locking feature between an unlocked orientation and a locked orientation.

21. The brace of claim 17, wherein each locking feature is configured to transition between an unlocked orientation and a locked orientation by turning the locking feature through a substantially quarter-turn.

22. The brace of claim 17, wherein each locking feature is configured to click two times upon insertion into any of the apertures.

23. The brace of claim 17, wherein each locking feature and each aperture comprise complementary threads.

24. The brace of claim 17, further comprising:

a plurality of straps configured for coupling to the cuff; and a central harness configured to directly couple to a first end of at least two of the plurality of straps, thereby ensuring the plurality of straps do not cross when the brace is properly attached to the subject.

25. The brace of claim 24, wherein the central harness comprises a substantially elastic material.

26. The brace of claim 24, wherein central harness comprises a fabric layer configured to be directly disposed against the skin of the subject.

27. The brace of claim 24, wherein the first end of the at least two of the plurality of straps comprise hook and loop fasteners configured to couple to the central harness.

28. The brace of claim 27, wherein the central harness comprises a plurality of alligator clip-type flaps, each flap comprising hook and loop fasteners on opposing inside surfaces thereof such that, when properly secured, the first end of each of the at least two of the plurality of straps is folded between and hook and loop fastened to the opposing inside surfaces of a respective one of the plurality of alligator clip-type flaps.

* * * * *